United States Patent
Kapur et al.

(10) Patent No.: US 11,261,492 B2
(45) Date of Patent: *Mar. 1, 2022

(54) METHODS FOR THE DIAGNOSIS OF FETAL ABNORMALITIES

(71) Applicants: The General Hospital Corporation, Boston, MA (US); GPB Scientific, LLC, Richmond, VA (US); Verinata Health, Inc., Redwood City, CA (US)

(72) Inventors: Ravi Kapur, Sharon, MA (US); Mehmet Toner, Charlestown, MA (US); Zihua Wang, Newton, MA (US); Martin Fuchs, Uxbridge, MA (US)

(73) Assignees: The General Hospital Corporation, Boston, MA (US); Verinata Health, Inc., Redwood City, CA (US); GPB Scientific, LLC, Richmond, VA (US)

(*) Notice: Subject to any disclaimer, the term of this patent is extended or adjusted under 35 U.S.C. 154(b) by 182 days.

This patent is subject to a terminal disclaimer.

(21) Appl. No.: 16/594,505

(22) Filed: Oct. 7, 2019

(65) Prior Publication Data

US 2020/0140949 A1 May 7, 2020

Related U.S. Application Data

(60) Continuation of application No. 16/046,047, filed on Jul. 26, 2018, now Pat. No. 10,435,751, which is a division of application No. 14/705,239, filed on May 6, 2015, now Pat. No. 10,041,119, which is a continuation of application No. 13/831,342, filed on Mar. 14, 2013, now abandoned, which is a continuation of application No. 13/306,520, filed on Nov. 29, 2011, now abandoned, which is a continuation of application No. 11/763,245, filed on Jun. 14, 2007, now Pat. No. 8,137,912.

(60) Provisional application No. 60/804,817, filed on Jun. 14, 2006, provisional application No. 60/804,819, filed on Jun. 14, 2006, provisional application No. 60/820,778, filed on Jul. 28, 2006.

(51) Int. Cl.
*C12Q 1/6883* (2018.01)
*G01N 1/30* (2006.01)
*G01N 33/68* (2006.01)

(52) U.S. Cl.
CPC ............ *C12Q 1/6883* (2013.01); *G01N 1/30* (2013.01); *G01N 33/6893* (2013.01); *C12Q 2600/156* (2013.01); *C12Q 2600/158* (2013.01); *C12Q 2600/16* (2013.01); *G01N 2800/385* (2013.01)

(58) Field of Classification Search
CPC ............ C12Q 1/6883; C12Q 2600/156; C12Q 2600/158; C12Q 2600/16; G01N 1/30; G01N 33/6893; G01N 2800/385; G01N 2800/387
See application file for complete search history.

(56) References Cited

U.S. PATENT DOCUMENTS

| | | |
|---|---|---|
| 4,683,202 A | 7/1987 | Mullis |
| 5,302,509 A | 4/1994 | Cheeseman |
| 5,641,628 A | 6/1997 | Bianchi |
| 5,670,325 A | 9/1997 | Lapidus et al. |
| 5,676,849 A | 10/1997 | Sammons et al. |
| 5,879,883 A | 3/1999 | Benson et al. |
| 5,962,234 A | 10/1999 | Golbus |
| 6,210,891 B1 | 4/2001 | Nyren et al. |
| 6,399,364 B1 | 6/2002 | Reeve et al. |
| 6,566,101 B1 | 5/2003 | Shuber et al. |
| 6,632,655 B1 | 10/2003 | Mehta et al. |
| 6,664,056 B2 | 12/2003 | Lo et al. |
| 7,171,975 B2 | 2/2007 | Moon et al. |
| 7,332,277 B2 | 2/2008 | Dhallan |
| 7,476,363 B2 | 1/2009 | Unger et al. |
| 7,645,576 B2 | 1/2010 | Lo et al. |
| 7,655,399 B2 | 2/2010 | Cantor et al. |
| 7,888,017 B2 | 2/2011 | Quake et al. |
| 8,008,018 B2 | 8/2011 | Quake et al. |
| 10,041,119 B2 | 8/2018 | Kapur et al. |
| 10,435,751 B2 * | 10/2019 | Kapur .............. C12Q 1/6883 |
| 2001/0051341 A1 | 12/2001 | Lo et al. |
| 2002/0012930 A1 | 1/2002 | Rothberg et al. |
| 2002/0119469 A1 | 8/2002 | Shuber et al. |
| 2002/0164816 A1 | 11/2002 | Quake |
| 2003/0013101 A1 | 1/2003 | Balasubramanian |
| 2003/0044388 A1 | 3/2003 | Dennis et al. |

(Continued)

FOREIGN PATENT DOCUMENTS

| | | |
|---|---|---|
| EP | 1262776 A3 | 1/2004 |
| EP | 1754788 A3 | 4/2007 |

(Continued)

OTHER PUBLICATIONS

Allard, et al. Tumor cells circulate in the peripheral blood of all major carcinomas but not in healthy subjects or patients with nonmalignant diseases. Clin Cancer Res. Oct. 15, 2004; 10(20):6897-6904.

Bustamante-Aragones et al.: "Detection of a Paternally Inherited Fetal Mutation in Maternal Plasma by the Use of Automated Sequencing", Ann. N.Y. Acad. Sci. 1075: 108-117 (2006), pp. 108-117, XP-002652985.

Chan, et al. Size distributions of maternal and fetal DNA in maternal plasma. Clin Chem. Jan. 2004;50(1):88-92.

(Continued)

*Primary Examiner* — David C Thomas
(74) *Attorney, Agent, or Firm* — Fish & Richardson P.C.

(57) ABSTRACT

The present invention relates to methods for detecting, enriching, and analyzing rare cells that are present in the blood, e.g. fetal cells. The invention further features methods of analyzing rare cell(s) to determine the presence of an abnormality, disease or condition in a subject, e.g. a fetus by analyzing a cellular sample from the subject.

30 Claims, 41 Drawing Sheets

Specification includes a Sequence Listing.

(56) References Cited

U.S. PATENT DOCUMENTS

| | | |
|---|---|---|
| 2003/0082566 A1 | 5/2003 | Sylvan |
| 2003/0165852 A1 | 9/2003 | Schueler et al. |
| 2003/0186255 A1 | 10/2003 | Williams et al. |
| 2003/0231791 A1 | 12/2003 | Torre-Bueno et al. |
| 2004/0137470 A1 | 7/2004 | Dhallan |
| 2005/0019792 A1 | 1/2005 | McBride et al. |
| 2005/0049793 A1 | 3/2005 | Paterlini-Brechot |
| 2005/0061962 A1 | 3/2005 | Mueth et al. |
| 2005/0129581 A1 | 6/2005 | McBride et al. |
| 2005/0145496 A1 | 7/2005 | Goodsaid et al. |
| 2005/0196785 A1 | 9/2005 | Quake et al. |
| 2005/0252773 A1 | 11/2005 | McBride et al. |
| 2005/0287611 A1 | 12/2005 | Nugent et al. |
| 2006/0060767 A1 | 3/2006 | Wang et al. |
| 2006/0073125 A1 | 4/2006 | Clarke et al. |
| 2006/0121452 A1 | 6/2006 | Dhallan |
| 2007/0134658 A1 | 6/2007 | Bohmer et al. |
| 2007/0202536 A1 | 8/2007 | Yamanishi et al. |
| 2007/0212689 A1 | 9/2007 | Bianchi et al. |
| 2007/0238105 A1 | 10/2007 | Barrett et al. |
| 2007/0275402 A1 | 11/2007 | Lo et al. |
| 2008/0090239 A1 | 4/2008 | Shoemaker et al. |
| 2008/0096216 A1 | 4/2008 | Quake |
| 2008/0193927 A1 | 8/2008 | Mann et al. |
| 2008/0213775 A1 | 9/2008 | Brody et al. |
| 2008/0299562 A1 | 12/2008 | Oeth et al. |
| 2009/0018024 A1* | 1/2009 | Church ............... C12Q 1/6874 506/2 |
| 2009/0029377 A1 | 1/2009 | Lo et al. |
| 2009/0087847 A1 | 4/2009 | Lo et al. |
| 2009/0170113 A1 | 7/2009 | Quake et al. |
| 2009/0170114 A1 | 7/2009 | Quake et al. |
| 2009/0215633 A1 | 8/2009 | Van Eijk et al. |
| 2009/0280492 A1 | 11/2009 | Stoughton et al. |
| 2009/0291443 A1 | 11/2009 | Stoughton et al. |
| 2010/0112575 A1 | 5/2010 | Fan et al. |
| 2010/0216151 A1 | 8/2010 | Lapidus et al. |
| 2010/0216153 A1 | 8/2010 | Lapidus et al. |

FOREIGN PATENT DOCUMENTS

| | | |
|---|---|---|
| EP | 1757694 A3 | 2/2008 |
| EP | 2161347 A2 | 3/2010 |
| EP | 2161347 A3 | 6/2010 |
| WO | WO99/22868 A1 | 5/1999 |
| WO | WO00/06770 A1 | 2/2000 |
| WO | WO00/40750 A1 | 7/2000 |
| WO | WO001/35071 A3 | 2/2002 |
| WO | WO003/020974 A2 | 3/2003 |
| WO | WO03/020986 A1 | 3/2003 |
| WO | WO03/044217 A2 | 5/2003 |
| WO | WO03/048295 A1 | 6/2003 |
| WO | WO003/018757 A3 | 9/2003 |
| WO | WO003/020974 A3 | 9/2003 |
| WO | WO02/073204 A3 | 10/2003 |
| WO | WO03/044217 A3 | 10/2003 |
| WO | WO03/031938 A3 | 11/2003 |
| WO | WO03/023057 A3 | 12/2003 |
| WO | WO03/069421 A3 | 12/2003 |
| WO | WO03/035895 A3 | 1/2004 |
| WO | WO03/035894 A3 | 3/2004 |
| WO | WO003/019141 A3 | 4/2004 |
| WO | WO04/029221 | 4/2004 |
| WO | WO04/065629 A1 | 8/2004 |
| WO | WO03/093795 A3 | 10/2004 |
| WO | WO04/037374 A3 | 10/2004 |
| WO | WO04/025251 A3 | 11/2004 |
| WO | WO04/101762 A3 | 2/2005 |
| WO | WO05/047532 A1 | 5/2005 |
| WO | WO05/049168 A3 | 9/2005 |
| WO | WO05/028663 A3 | 12/2005 |
| WO | WO05/098046 A3 | 12/2005 |
| WO | WO05/118852 A2 | 12/2005 |
| WO | WO05/085861 A3 | 2/2006 |
| WO | WO06/010610 A2 | 2/2006 |
| WO | WO05/118852 A3 | 3/2006 |
| WO | WO05/121362 A3 | 4/2006 |
| WO | WO06/043181 A2 | 4/2006 |
| WO | WO005/109238 A3 | 6/2006 |
| WO | WO06/010610 A3 | 6/2006 |
| WO | WO06/043181 A3 | 6/2006 |
| WO | WO05/043121 A3 | 8/2006 |
| WO | WO06/078470 A3 | 9/2006 |
| WO | WO06/097049 A1 | 9/2006 |
| WO | WO05/042713 A3 | 11/2006 |
| WO | WO06/023563 A3 | 11/2006 |
| WO | WO05/084380 A3 | 12/2006 |
| WO | WO05/116264 A3 | 2/2007 |
| WO | WO04/076643 A3 | 3/2007 |
| WO | WO07/024264 A3 | 4/2007 |
| WO | WO07/044091 A2 | 4/2007 |
| WO | WO07/030949 A3 | 5/2007 |
| WO | WO07/034221 A3 | 5/2007 |
| WO | WO05/058937 A3 | 6/2007 |
| WO | WO07/048076 A3 | 7/2007 |
| WO | WO07/053648 A3 | 7/2007 |
| WO | WO07/075836 A2 | 7/2007 |
| WO | WO07/080583 A2 | 7/2007 |
| WO | WO07/050495 A3 | 8/2007 |
| WO | WO07/075879 A3 | 8/2007 |
| WO | WO07/092473 A2 | 8/2007 |
| WO | WO06/100366 A3 | 9/2007 |
| WO | WO07/033167 A3 | 10/2007 |
| WO | WO07/038264 A3 | 10/2007 |
| WO | WO07/044690 A3 | 10/2007 |
| WO | WO07/053785 A3 | 10/2007 |
| WO | WO07/059430 A3 | 10/2007 |
| WO | WO05/084374 A3 | 11/2007 |
| WO | WO07/035414 A3 | 11/2007 |
| WO | WO07/044091 A3 | 11/2007 |
| WO | WO07/089880 A3 | 11/2007 |
| WO | WO07/126938 A2 | 11/2007 |
| WO | WO07/132166 A2 | 11/2007 |
| WO | WO07/132167 A2 | 11/2007 |
| WO | WO07/082379 A3 | 12/2007 |
| WO | WO07/098484 A3 | 12/2007 |
| WO | WO07/062222 A3 | 1/2008 |
| WO | WO07/100684 A3 | 1/2008 |
| WO | WO07/075836 A3 | 2/2008 |
| WO | WO07/132166 A3 | 2/2008 |
| WO | WO08/017871 A1 | 2/2008 |
| WO | WO07/089911 A3 | 5/2008 |
| WO | WO07/132167 A3 | 5/2008 |
| WO | WO07/028146 A3 | 6/2008 |
| WO | WO07/067734 A3 | 8/2008 |
| WO | WO07/126938 A3 | 10/2008 |
| WO | WO07/082154 A3 | 11/2008 |
| WO | WO07/087612 A3 | 11/2008 |
| WO | WO07/092473 A3 | 11/2008 |
| WO | WO07/082144 A3 | 12/2008 |
| WO | WO07/092713 A3 | 12/2008 |
| WO | WO07/079229 A3 | 1/2009 |
| WO | WO07/080583 A3 | 2/2009 |
| WO | WO07/079250 A3 | 3/2009 |
| WO | WO07/041610 A3 | 4/2009 |
| WO | WO09/019455 A3 | 4/2009 |

OTHER PUBLICATIONS

Chern & Chen, et al. Molecular prenatal diagnosis of thalassemia in Taiwan, International Journal of Gynecology & Obstetrics, May 2000, 69(2):103-105.

Chiu, et al. Noninvasive prenatal diagnosis of fetal chromosomal aneuploidy by massively parallel genomic sequencing of DNA in maternal plasma. Proc Natl Acad Sci U S A. Dec. 23, 2008; 105(51):20458-63.

Cristofanilli, et al., Circulating Tumor Cells Revisited, JAMA, vol. 303, No. 11 (2010).

Deng, et al. Enumeration and microfluidic chip separation of circulating fetal cells early in pregnancy from maternal blood. American Journal of Obstetrics & Gynecology. Dec. 2008 (vol. 199, Issue 6, p. S134).

(56) References Cited

OTHER PUBLICATIONS

Dinaro, et al. Prenatal diagnosis of beta-thalassaemia using fetal erythroblasts enriched from maternal blood by a novel gradient. Mol Hum Reprod. 2000; 6(6):571-4.
Dohm, et al. Substantial biases in ultra-short read data sets from high-throughput DNA sequencing. Nucleic Acids Research. 2008. 36: e105 doi: 10.1093\nark\gkn425.
Dragovich, et al., Anti-EGFR-Targeted Therapy for Esophageal and Gastric Cancers: An Evolving Concept, Journal of Oncology, vol. 2009, Article ID 804108, 8 pages (2009).
EP Office Action in European Appln. No. 18167847.5, dated Jan. 2, 2020, 7 pages.
European Search Opinion dated Jul. 31, 2009 for EP07763674.4.
European search report dated Nov. 9, 2009 for Application No. 7784442.1.
European search report dated Dec. 21, 2009 for Application No. 07798579.4.
European Search Report dated Dec. 21, 2010 for EP07763674.4.
European search report dated Dec. 22, 2009 for Application No. 07798580.2.
European search report dated Dec. 22, 2009 for Application No. 0778444.7.
European Search Report dated Jul. 31, 2009 for EP07763674.4.
Examination report dated Aug. 27, 2010 from corresponding U.S. Appl. No. 11/762,747.
Examination Report for EP Application No. 1115937.1 dated Dec. 18, 2012, 8 pages.
Examination Report for EP Application No. 1115937.1 dated Jun. 26, 2012, 7 pages.
Examination Report for EP Application No. EP07763674.4 dated Mar. 3, 2009.
Examination Report for EP Application No. EP07763674.4 dated Sep. 23, 2009.
Extended European Search Report for Application No. 1115937.1 dated Aug. 10, 2011, 10 pages.
Extended European Search Report for EP Application No. 12175907.0 dated Jan. 2, 2013, 11 pages.
Extended European Search Report in Application No. 18167847.5, dated Sep. 19, 2018, 12 pages.
Fan et al. Highly parallel SNP genotyping. Cold Spring Harbor Symp. Quant. Biol. (2003) vol. LXVIII, p. 69-78.
Fan, et al. Detection of aneuploidy with digital polymerase chain reaction. Anal Chem. Oct. 1, 2007; 79(19):7576-9.
Fan, et al. Microfluidic digital PCR enables rapid prenatal diagnosis of fetal aneuploidy. Am J Obstet Gynecol. May 2009; 200(5):543. e1-7.
Fan, et al. Noninvasive diagnosis of fetal aneuploidy by shotgun sequencing DNA from maternal blood. Proc Natl Acad Sci U S A. Oct. 21, 2008; 105(42):16266-71 . . . .
Fan, et al. Single cell degenerate oligonucleotide primer-PCR and comparative genomic hybridization with modified control reference. Journal of Ahejian University—Science A. 2001; 2(3):318-321.
Fullwood, et al. Next Generation DNA sequencing of paired-end tags (PET) for transcriptome and genome analyses. Genome Research. 2009. 19:521-532.
Furdui, et al. Immunomagnetic T cell capture from blood for PCR analysis using microfluidic systems. Lab Chip. Dec. 2004; 4(6):614-8.
Ghia, et al. Ordering of human bone marrow B lymphocyte precursors by single-cell polymerase chain reaction analyses of the rearrangement status of the immunoglobulin H and L chain gene loci. J Exp Med. Dec. 1, 1996; 184(6):2217-29.
Hamabe, et al. Molecular study of the Prader-Willi syndrome: deletion, RFLP, and phenotype analyses of 50 patients. Am J Med Genet. Oct. 1, 1991; 41(1):54-63.
Hosono, et al. Unbiased whole-genome amplification directly from clinical samples. Genome Res. May 2003; 13(5):954-64.
Hviid, T. In-cell polymerase chain reaction: strategy and diagnostic applications. Methods Mol Biol. 2006, 336:45-58.

International preliminary report on patentability dated Oct. 29, 2008 for PCT/US2007/003209.
International search report and written opinion dated Mar. 16, 2010 for PCT Application No. US2009/57136.
International search report dated Jan. 16, 2008 for PCT Application No. US2007/71247.
International search report dated Jan. 25, 2008 for PCT Application No. US2007/71250.
International search report dated Nov. 15, 2007 for PCT Application No. US2007/71149.
International search report dated Nov. 26, 2007 for PCT Application No. US2007/71256.
International search report dated Feb. 25, 2008 for PCT Application No. US2007/071148.
International search report dated Feb. 25, 2008 for PCT Application No. US2007/071248.
Kartalov et al.: "Microfluidic device reads up to four consecutive base pairs in DNA sequencing-by-synthesis.", Nucleic Acids Research, 2004, vol. 32, No. 9, 2004, pp. 2873-2879, XP-002652987.
Kobayashi, et al., 'EGFR Mutation and Resistance of Non-Small-Cell Lung Cancer to Gefitinib,' The New England Journal of Medicine, vol. 352, pp. 786-792 (2005).
Korenberg, et al. Down syndrome phenotypes: the consequences of chromosomal imbalance. PNAS 1994; 91:4997-5001.
Kurg et al. Genetic Testing. Arrayed Primer Extension: Solid-Phase Four-Color DNA Resequencing and Mutation Detection Technology. 2000. 4:1-7.
Leutwyler, K. Mapping Chromosome 21. Available at http://www.scientificamerican.com/article.cfm?id=mapping-chromosome-21. Accessed Feb. 3, 2010.
Li, et al. Mapping short DNA sequencing reads and calling variants using mapping quality scores. Genome Research. Genome Res. Nov. 2008; 18(11):1851-8.
Li, et al. Size separation of circulatory DNA in maternal plasma permits ready detection of fetal DNA polymorphisms. Clin Chem. Jun. 2004; 50(6):1002-11.
Marks, et al. Epidermal growth factor receptor (EGFR) expression in prostatic adenocarcinoma after hormonal therapy: a fluorescence in situ hybridization and immunohistochemical analysis. The Prostate. 2008; 68:919-923.
McCarley, et al. Patterning of surface-capture architectures in polymer-based microanalytical devices. In Kuther, et al. Eds. Royal Society of Chemistry Special Publication. 2005; 130-132. (Abstract only).
Meng et al.: "Design and Synthesis of a Photocleavable Fluorescent Nucleotide 3'-0-Allyl-dGTP-PC-Bodipy-FL-510 as a Reversible Terminator for DNA Sequencing by Synthesis", J. Org. Chem. 2006, 71, pp. 2873-2879, XP-002652986.
Murakami, et al. A novel single cell PCR assay: detection of human T lymphotropic virus type I DNA in lymphocytes of patients with adult T cell leukemia. Leukemia. Oct. 1998; 12(10):1645-50.
Office Action issued in U.S. Appl. No. 11/067,102 dated Apr. 4, 2008.
Office Action issued in U.S. Appl. No. 11/067,102 dated Apr. 13, 2009.
Office Action issued in U.S. Appl. No. 11/067,102 dated Aug. 1, 2008.
Office Action issued in U.S. Appl. No. 11/067,102 dated Feb. 4, 2010.
Office Action issued in U.S. Appl. No. 11/067,102 dated Jun. 15, 2007.
Office Action issued in U.S. Appl. No. 11/067,102 dated Sep. 17, 2010.
Office Action issued in U.S. Appl. No. 11/228,454 dated Mar. 4, 2009.
Office Action issued in U.S. Appl. No. 11/701,686 dated Jan. 28, 2009.
Office Action issued in U.S. Appl. No. 11/701,686 dated Jan. 27, 2010.
Office Action issued in U.S. Appl. No. 11/701,686 dated Sep. 11, 2009.
Office Action issued in U.S. Appl. No. 11/701,686 dated Sep. 8, 2010.

(56) References Cited

OTHER PUBLICATIONS

Office Action issued in U.S. Appl. No. 11/763,133 dated Jan. 12, 2009.
Office Action issued in U.S. Appl. No. 11/763,133 dated Nov. 3, 2009.
Office Action issued in U.S. Appl. No. 11/763,245 dated Jul. 26, 2011.
Office Action issued in U.S. Appl. No. 11/763,245 dated Mar. 11, 2010.
Office Action issued in U.S. Appl. No. 11/763,245 dated Mar. 29, 2011.
Office Action issued in U.S. Appl. No. 11/763,421 dated Dec. 31, 2009.
Office Action issued in U.S. Appl. No. 11/763,421 dated Jul. 10, 2009.
Office Action issued in U.S. Appl. No. 11/763,426 dated Dec. 3, 2008.
Office Action issued in U.S. Appl. No. 11/763,426 dated Feb. 15, 2011.
Office Action issued in U.S. Appl. No. 11/763,426 dated Dec. 1, 2009.
Office Action issued in U.S. Appl. No. 11/763,426 dated Jun. 14, 2010.
Office Action issued in U.S. Appl. No. 11/763,431 dated May 4, 2009.
Office Action issued in U.S. Appl. No. 12/393,803 dated Apr. 25, 2011.
Office Action issued in U.S. Appl. No. 13/306,520 dated Apr. 9, 2013.
Office Action issued in U.S. Appl. No. 13/831,342 dated Nov. 7, 2014.
Peixoto, et al. Quantification of multiple gene expression in individual cells. Genome Res. Oct. 2004; 14(10A):1938-47.
Pfaffl, et al. Relative expression software tool (REST) for group-wise comparison and statistical analysis of relative expression results in real-time PCR. Nucleic Acids Res. May 1, 2002; 30(9):e36.
Pohl et al. Principle and applications of digital PCR. Expert Rev Mol Diagn. Jan. 2004; 4(1):41-7.
Shendure, et al. Next-generation DNA sequencing. Nature. 2008; 26(10):1135-1145.
Summons to Attend Oral Proceedings in European Application No. 12175907, dated Jul. 21, 2017, 7 pages.
Tettelin, et al. The nucleotide sequence of *Saccharomyces cerevisiae* chromosome VII. Nature. May 29, 1997; 387(6632 Suppl):81-4.
Tufan et al., Analysis of Cell-Free Fetal DNA from Maternal Plasma and Serum Using a Conventional Multiplex PCR: Factors Influencing Success. 2005. Turk. J. Med. Sci. 35:85-92.
Voldborg, et al., 'Epidermal growth factor receptor (EGFR) and EGFR mutations, function and possible role in clinical trials,' Annals of Oncology, vol. 8, pp. 1197-1206 (1997).
Von Eggeling, et al. Determination of the origin of single nucleated cells in maternal circulation by means of random PCR and a set of length polymorphisms. Hum Genet. Feb. 1997;99(2):266-70.
Vrettou, et al. Real-time PCR for single-cell genotyping in sickle cell and thalassemia syndromes as a rapid, accurate, reliable, and widely applicable protocol for preimplantation genetic diagnosis. Human Mutation. 2004; 23(5):513-21.
Warren, et al. Transcription factor profiling in individual hematopoietic progenitors by digital RT-PCR. PNAS. Nov. 21, 2006; 103(47):17807-17812.
White, et al. Digital PCR provides sensitive and absolute calibration for high throughput sequencing. BMC Genomics. Mar. 19, 2009;10:116.
Zavala, et al. Genomic GC content prediction in prokaryotes from a sample of genes. Gene. Sep. 12, 2005;357(2):137-43.
Zimmerman, et al. Novel real-time quantitative PCR test for trisomy 21. Jan. 1, 2002. Clinical Chemistry, American Association for Clinical Chemistry. 48:(2) 362-363.

\* cited by examiner

Microposts and cells

Antibody coated posts

| | | |
|---|---|---|
| 2AR | ATP-BINDING CASSETTE SUBFAMILY C MEMBER (ABCC1) | BREAST CANCER TYPE 1 (BRCA1) |
| A DISINTEGRIN | | BREAST CANCER TYPE 2 (BRCA2) |
| ACTIVATOR OF THYROID AND RETINOIC ACID RECEPTOR (ACTR) | BAG-1 | |
| | BASIGIN (BSG) | BREAST CARCINOMA AMPLIFIED SEQUENCE 2 (BCAS2) |
| ADAM 11 | BCEI | |
| ADIPOGENESIS INHIBITORY FACTOR (ADIF) | B-CELL DIFFERENTIATION FACTOR (BCDF) | CADHERIN |
| | B-CELL LEUKEMIA 2 (BCL-2) | EPITHELIAL CADHERIN-11 |
| ALPHA 6 INTEGRIN SUBUNIT | | CADHERIN-ASSOCIATED PROTEIN |
| | B-CELL STIMULATORY FACTOR-2 (BSF-2) | |
| ALPHA V INTEGRIN SUBUNIT | | CALCITONIN RECEPTOR (CTR) |
| | BCL-1 | |
| ALPHA-CATENIN | BCL-2-ASSOCIATED X PROTEIN (BAX) | CALCIUM PLACENTAL PROTEIN (CAPL) |
| AMPLIFIED IN BREAST CANCER 1 (AIB1) | | |
| | BCRP | CALCYCLIN |
| AMPLIFIED IN BREAST CANCER 3 (AIB3) | BETA 1 INTEGRIN SUBUNIT | CALLA |
| | BETA 3 INTEGRIN SUBUNIT | CAM5 |
| AMPLIFIED IN BREAST CANCER 4 (AIB4) | BETA 5 INTEGRIN SUBUNIT | CAPL |
| | BETA-2 INTERFERON | CARCINOEMBRYONIC ANTIGEN (CEA) |
| AMYLOID PRECURSOR PROTEIN SECRETASE (APPS) | BETA-CATENIN | |
| | BETA-CATENIN | CATENIN |
| | BONE SIALOPROTEIN (BSP) | ALPHA 1 |
| AP-2 GAMMA | BREAST CANCER ESTROGEN-INDUCIBLE SEQUENCE (BCEI) | CATHEPSIN B |
| APPS | | CATHEPSIN D |
| ATP-BINDING CASSETTE TRANSPORTER (ABCT) | | CATHEPSIN K |
| | | CATHEPSIN L2 |
| PLACENTA-SPECIFIC (ABCP) | BREAST CANCER RESISTANCE PROTEIN (BCRP) | CATHEPSIN O |
| | | CATHEPSIN O1 |
| | | CATHEPSIN V |

FIG. 5

| | | |
|---|---|---|
| CD10 | COMMON ACUTE LYMPHOCYTIC LEUKEMIA ANTIGEN (CALLA) | ENDOTHELIAL CELL GROWTH FACTOR (ECGR) |
| CD146 | | PLATELET-DERIVED (PD-ECGF) |
| CD147 | CONNEXIN 26 (Cx26) | |
| CD24 | CONNEXIN 43 (Cx43) | ENKEPHALINASE |
| CD29 | CORTACTIN | EPIDERMAL GROWTH FACTOR RECEPTOR (EGFR) |
| CD44 | COX-2 | |
| CD51 | CTLA-8 | EPISIALIN |
| CD54 | CTR | EPITHELIAL MEMBRANE ANTIGEN (EMA) |
| CD61 | CTSD | |
| CD66e | CYCLIN D1 | ER-ALPHA |
| CD82 | CYCLOOXYGENASE-2 | ERBB2 |
| CD87 | CYTOKERATIN 18 | ERBB4 |
| CD9 | CYTOKERATIN 19 | ER-BETA |
| CEA | CYTOKERATIN 8 | ERF-1 |
| CELLULAR RETINOL-BINDING PROTEIN 1 (CRBP1) | CYTOTOXIC T-LYMPHOCYTE-ASSOCIATED SERINE ESTERASE 8 (CTLA-8) | ERYTHROID-POTENTIATING ACTIVITY (EPA) |
| c-ERBB-2 | | ESR1 |
| CK7 | DIFFERENTIATION-INHIBITING ACTIVITY (DIA) | ESTROGEN RECEPTOR-ALPHA |
| CK8 | | |
| CK18 | DNA AMPLIFIED IN MAMMARY CARCINOMA 1 (DAM1) | ESTROGEN RECEPTOR-BETA |
| CK19 | | |
| CK20 | | ETS-1 |
| CLAUDIN-7 | DNA TOPOISOMERASE II ALPHA | EXTRACELLULAR MATRIX METALLOPROTEINASE INDUCER (EMMPRIN) |
| c-MET | DR-NM23 | |
| COLLAGENASE FIBROBLAST | E-CADHERIN | FIBRONECTIN RECEPTOR BETA POLYPEPTIDE (FNRB) |
| COLLAGENASE INTERSTITIAL | EMMPRIN | |
| COLLAGENASE-3 | EMS1 | FIBRONECTIN RECEPTOR BETA SUBUNIT (FNRB) |

FIG. 5
(continued)

| | | |
|---|---|---|
| FLK-1 | GROWTH FACTOR RECEPTOR BOUND-7 (GRB-7) | INTERLEUKIN-1 ALPHA (IL-1A) |
| GA15.3 | | INTERLEUKIN-1 BETA (IL-1B) |
| GA733.2 | GSTp | |
| GALECTIN-3 | HAP | INTERLEUKIN-11 (IL-11) |
| GAMMA-CATENIN | HEAT-SHOCK COGNATE PROTEIN 70 (HSC70) | INTERLEUKIN-17 (IL-17) |
| GAP JUNCTION PROTEIN (26 kDa) | | INTERLEUKIN-18 (IL-18) |
| | HEAT-STABLE ANTIGEN | INTERLEUKIN-6 (IL-6) |
| GAP JUNCTION PROTEIN (43 kDa) | HEPATOCYTE GROWTH FACTOR (HGF) | INTERLEUKIN-8 (IL-8) |
| GAP JUNCTION PROTEIN ALPHA-1 (GJA1) | HEPATOCYTE GROWTH FACTOR RECEPTOR (HGFR) | INVERSELY CORRELATED WITH ESTROGEN RECEPTOR EXPRESSION-1 (ICERE-1) |
| GAP JUNCTION PROTEIN BETA-2 (GJB2) | HEPATOCYTE-STIMULATING FACTOR III (HSF III) | |
| GCP1 | | KAI1 |
| GELATINASE A | HER-2 | KDR |
| GELATINASE B | HER2/NEU | KERATIN 8 |
| GELATINASE (72 kDa) | HERMES ANTIGEN | KERATIN 18 |
| GELATINASE (92 kDa) | HET | KERATIN 19 |
| GLIOSTATIN | HHM | KISS-1 |
| GLUCOCORTICOID RECEPTOR INTERACTING PROTEIN 1 (GRIP1) | HUMORAL HYPERCALCEMIA OF MALIGNANCY (HHM) | LEUKEMIA INHIBITORY FACTOR (LIF) |
| | | LIF |
| GLUTATHIONE S-TRANSFERASE p | ICERE-1 | LOST IN INFLAMMATORY BREAST CANCER (LIBC) |
| | INT-1 | |
| GM-CSF | INTERCELLULAR ADHESION MOLECULE-1 (ICAM-1) | LOT ("LOST ON TRANSFORMATION") |
| GRANULOCYTE CHEMOTACTIC PROTEIN 1 (GCP1) | | LYMPHOCYTE HOMING RECEPTOR |
| | INTERFERON-GAMMA-INDUCING FACTOR (IGIF) | MACROPHAGE-COLONY STIMULATING FACTOR |
| GRANULOCYTE-MACROPHAGE-COLONY STIMULATING FACTOR | | MAGE-3 |

FIG. 5
(continued)

| | | |
|---|---|---|
| MAMMAGLOBIN | MOESIN | NME2 |
| MASPIN | MONOCYTE ARGININE-SERPIN | NUCLEAR RECEPTOR COACTIVATOR-1 (NCoA-1) |
| MC56 | | |
| M-CSF | MONOCYTE-DERIVED NEUTROPHIL CHEMOTACTIC FACTOR | NUCLEAR RECEPTOR COACTIVATOR-2 (NCoA-2) |
| MDC | | |
| MDNCF | | NUCLEAR RECEPTOR COACTIVATOR-3 (NCoA-3) |
| MDR | MONOCYTE-DERIVED PLASMINOGEN ACTIVATOR INHIBITOR | |
| MELANOMA CELL ADHESION MOLECULE (MCAM) | | NUCLEOSIDE DIPHOSPHATE KINASE A (NDPKA) |
| | MTS-1 | |
| | MUC-1 | NUCLEOSIDE DIPHOSPHATE KINASE B (NDPKB) |
| MEMBRANE METALLOENDOPEPTIDASE (MME) | MUC18 | |
| | MUCIN LIKE CANCER ASSOCIATED ANTIGEN (MCA) | ONCOSTATIN M (OSM) |
| MEMBRANE-ASSOCIATED NEUTRAL ENDOPEPTIDASE (NEP) | | ORNITHINE DECARBOXYLASE (ODC) |
| | MUCIN | |
| | MUC-1 | OSTEOCLAST DIFFERENTIATION FACTOR (ODF) |
| CYSTEINE-RICH PROTEIN (MDC) | MULTIDRUG RESISTANCE PROTEIN 1 (MDR, MDR1) | |
| METASTASIN (MTS-1) | | OSTEOCLAST DIFFERENTIATION FACTOR RECEPTOR (ODFR) |
| MLN64 | MULTIDRUG RESISTANCE RELATED PROTEIN-1 (MRP, MRP-1) | |
| MMP1 | | |
| MMP2 | | OSTEONECTIN (OSN, ON) |
| MMP3 | N-CADHERIN | OSTEOPONTIN (OPN) |
| MMP7 | NEP | OXYTOCIN RECEPTOR (OXTR) |
| MMP9 | NEU | |
| MMP11 | NEUTRAL ENDOPEPTIDASE | |
| MMP13 | NEUTROPHIL-ACTIVATING PEPTIDE 1 (NAP1) | p27/kip1 |
| MMP14 | | p300/CBP COINTEGRATOR ASSOCIATE PROTEIN (p/CIP) |
| MMP15 | NM23-H1 | |
| MMP16 | NM23-H2 | |
| MMP17 | NME1 | p53 |

FIG. 5
(continued)

| | | |
|---|---|---|
| p9Ka | PLATELET GLYCOPROTEIN IIIa (GP3A) | REPRESSOR OF ESTROGEN RECEPTOR ACTIVITY (REA) |
| PAI-1 | PLAU | S100A4 |
| PAI-2 | PLEOMORPHIC ADENOMA GENE-LIKE 1 (PLAGL1) | S100A6 |
| PARATHYROID ADENOMATOSIS 1 (PRAD1) | POLYMORPHIC EPITHELIAL MUCIN (PEM) | S100A7 |
| PARATHYROID HORMONE-LIKE HORMONE (PTHLH) | PRAD1 | S6K |
| PARATHYROID HORMONE-RELATED PEPTIDE (PTHrP) | PROGESTERONE RECEPTOR (PgR) | SART-1 |
| P-CADHERIN | PROGESTERONE RESISTANCE | SCAFFOLD ATTACHMENT FACTOR B (SAF-B) |
| PD-ECGF | PROSTAGLANDIN ENDOPEROXIDE SYNTHASE-2 | SCATTER FACTOR (SF) |
| PDGF-□ | | SECRETED PHOSPHOPROTEIN-1 (SPP-1) |
| PEANUT-REACTIVE URINARY MUCIN (PUM) | | SECRETED PROTEIN ACIDIC AND RICH IN CYSTEINE (SPARC) |
| P-GLYCOPROTEIN (P-GP) | PROSTAGLANDIN G/H SYNTHASE-2 | STANNICALCIN |
| PGP-1 | PROSTAGLANDIN H SYNTHASE-2 | STEROID RECEPTOR COACTIVATOR-1 (SRC-1) |
| PHGS-2 | | STEROID RECEPTOR COACTIVATOR-2 (SRC-2) |
| PHS-2 | pS2 | |
| PIP | PS6K | STEROID RECEPTOR COACTIVATOR-3 (SRC-3) |
| PLAKOGLOBIN | PSORIASIN | |
| PLASMINOGEN ACTIVATOR INHIBITOR (TYPE 1) | PTHLH | STEROID RECEPTOR RNA ACTIVATOR (SRA) |
| | PTHrP | STROMELYSIN-1 |
| PLASMINOGEN ACTIVATOR INHIBITOR (TYPE 2) | RAD51 | STROMELYSIN-3 |
| | RAD52 | TENASCIN-C (TN-C) |
| | RAD54 | TESTES-SPECIFIC PROTEASE 50 |
| PLASMINOGEN ACTIVATOR (TISSUE-TYPE) | RAP46 | |
| | RECEPTOR-ASSOCIATED COACTIVATOR 3 (RAC3) | THROMBOSPONDIN I |
| PLASMINOGEN ACTIVATOR (UROKINASE-TYPE) | | THROMBOSPONDIN II |

FIG. 5
(continued)

| | | |
|---|---|---|
| THYMIDINE PHOSPHORYLASE (TP) | TSP-2 | VASCULAR ENDOTHELIAL GROWTH FACTOR-A |
| THYROID HORMONE RECEPTOR ACTIVATOR MOLECULE 1 (TRAM-1) | TSP2 | |
| | TSP50 | VASCULAR PERMEABILITY FACTOR |
| TIGHT JUNCTION PROTEIN 1 (TJP1) | TUMOR CELL COLLAGENASE STIMULATING FACTOR (TCSF) | VEGFR2 |
| | | VERY LATE T-CELL ANTIGEN BETA (VLA-BETA) |
| TIMP1 | TUMOR-ASSOCIATED EPITHELIAL MUCIN | |
| TIMP2 | | VIMENTIN |
| TIMP3 | uPA | VITRONECTIN RECEPTOR ALPHA POLYPEPTIDE (VNRA) |
| TIMP4 | uPAR | |
| TISSUE-TYPE PLASMINOGEN ACTIVATOR | UROKINASE | |
| | UROKINASE-TYPE PLASMINOGEN ACTIVATOR | VITRONECTIN RECEPTOR |
| | | VON WILLEBRAND FACTOR |
| TN-C | | |
| TP53 | UROKINASE-TYPE PLASMINOGEN ACTIVATOR RECEPTOR (uPAR) | VPF |
| tPA | | VWF |
| TRANSCRIPTIONAL INTERMEDIARY FACTOR 2 (TIF2) | | WNT-1 |
| | | ZAC |
| | UVOMORULIN | ZO-1 |
| TREFOIL FACTOR 1 (TFF1) | VASCULAR ENDOTHELIAL GROWTH FACTOR | ZONULA OCCLUDENS-1 |
| TSG101 | | |
| TSP-1 | VASCULAR ENDOTHELIAL GROWTH FACTOR RECEPTOR-2 (VEGFR2) | |
| TSP1 | | |

FIG. 5
(continued)

chip

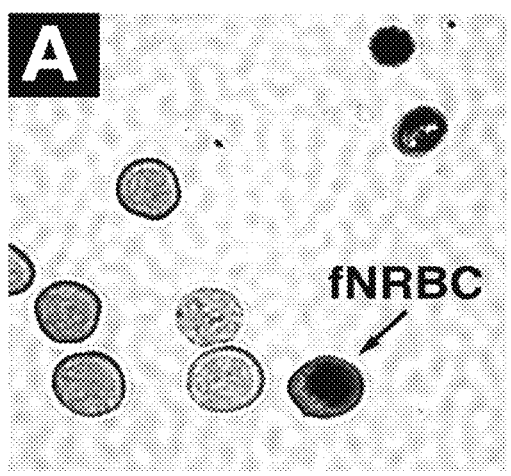
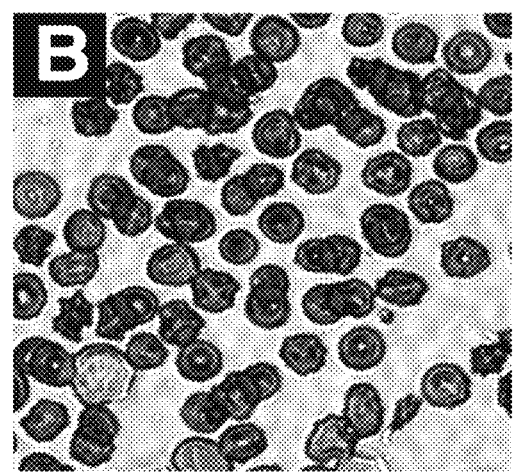
FIG. 15A
FIG. 15B (Blue = nucleus, Red = X chromosome, Green = Y chromosome)

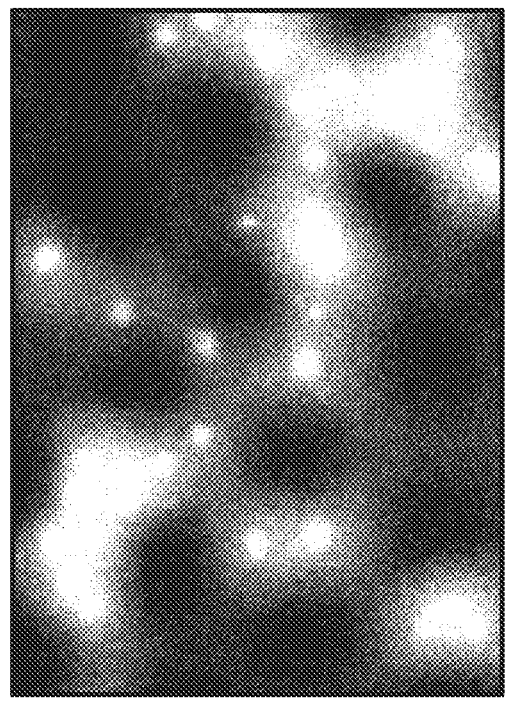
FIG. 21

METHODS FOR THE DIAGNOSIS OF FETAL ABNORMALITIES

CROSS-REFERENCE

This application claims the benefit of U.S. Provisional Application No. 60/804,817, filed Jun. 14, 2006, which application is incorporated herein by reference.

BACKGROUND OF THE INVENTION

Analysis of specific cells can give insight into a variety of diseases. These analyses can provide non-invasive tests for detection, diagnosis and prognosis of diseases, thereby eliminating the risk of invasive diagnosis. For instance, social developments have resulted in an increased number of prenatal tests. However, the available methods today, amniocentesis and chorionic villus sampling (CVS) are potentially harmful to the mother and to the fetus. The rate of miscarriage for pregnant women undergoing amniocentesis is increased by 0.5-1% e, and that figure is slightly higher for CVS. Because of the inherent risks posed by amniocentesis and CVS, these procedures are offered primarily to older women, i.e., those over 35 years of age, who have a statistically greater probability of bearing children with congenital defects. As a result, a pregnant woman at the age of 35 has to balance an average risk of 0.5-1% to induce an abortion by amniocentesis against an age related probability for trisomy 21 of less than 0.3%. To eliminate the risks associated with invasive prenatal screening procedures, non-invasive tests for detection, diagnosis and prognosis of diseases, have been utilized. For example, maternal serum alpha-fetoprotein, and levels of unconjugated estriol and human chorionic gonadotropin are used to identify a proportion of fetuses with Down's syndrome, however, these tests are not one hundred percent accurate. Similarly, ultrasonography is used to determine congenital defects involving neural tube defects and limb abnormalities, but is useful only after fifteen weeks' gestation Moreover, despite decades of advances in cancer diagnosis and therapy, many cancers continue to go undetected until late in their development. As one example, most early-stage lung cancers are asymptomatic and are not detected in time for curative treatment, resulting in an overall five-year survival rate for patients with lung cancer of less than 15%. However, in those instances in which lung cancer is detected and treated at an early stage, the prognosis is much more favorable.

The presence of fetal cells in the maternal circulation and cancer cells in patients' circulation offers an opportunity to develop prenatal diagnostics that obviates the risks associated with invasive diagnostic procedure, and cancer diagnostics that allow for detecting cancer at earlier stages in the development of the disease. However, fetal cells and cancer cells are rare as compared to the presence of other cells in the blood. Therefore, any proposed analysis of fetal cells or cancer cells to diagnose fetal abnormalities or cancers, respectively, requires enrichment of fetal cells and cancer cells. Enriching fetal cells from maternal peripheral blood and cancer cells from patient's blood is challenging, time intensive and any analysis derived there from is prone to error. The present invention addresses these challenges.

SUMMARY OF THE INVENTION

The methods of the present invention allow for enrichment of rare cell populations, particularly fetal cells or cancer cells, from peripheral blood samples which enrichment yields cell populations sufficient for reliable and accurate clinical diagnosis. The methods of the present invention also provide analysis of said enriched rare cell populations whereby said methods allow for detection, diagnosis and prognosis of conditions or diseases, in particular fetal abnormalities or cancer.

The present invention relates to methods for determining a condition in a patient or a fetus by analyzing nucleic acids from cells of samples obtained from patient or maternal samples, respectively. The methods include enriching the sample for cells that are normally present in vivo at a concentration of less than 1 in 100,000, obtaining the nuclei from the enriched sample cells and detecting substantially in real time one or more nucleic acids molecules. The sample can be enriched for a variety of cells including fetal cells, epithelial cells, endothelial cells or progenitor cells, and the sample can be obtained from a variety of sources including whole blood, sweat, tears, ear flow, sputum, lymph, bone marrow suspension, lymph, urine, saliva, semen, vaginal flow, cerebrospinal fluid, brain fluid, ascites, milk, secretions of the respiratory, intestinal or genitourinary tracts fluid. Preferably, the sample is a blood sample.

In some embodiments, samples are enriched in fetal cells, and the condition that can be determined by the methods of the invention can be a genetic or pathologic condition. In some embodiments, genetic conditions that can be determined in one or more fetal cells include trisomy 13, trisomy 18, trisomy 21, Klinefelter Syndrome, dup(17)(p11.2p11.2) syndrome, Down syndrome, Pre-eclampsia, Pro-term labor, Edometriosis, Pelizaeus-Merzbacher disease, dup(22)(q11.2q11.2) syndrome, Cat eye syndrome, Cri-du-chat syndrome, Wolf-Hirschhorn syndrome, Williams-Beuren syndrome, Charcot-Marie-Tooth disease, neuropathy with liability to pressure palsies, Smith-Magenis syndrome, neurofibromatosis, Alagille syndrome, Velocardiofacial syndrome, DiGeorge syndrome, steroid sulfatase deficiency, Kallmann syndrome, microphthalmia with linear skin defects, Adrenal hypoplasia, Glycerol kinase deficiency, Pelizaeus-Merzbacher disease, testis-determining factor on Y, Azospermia (factor a), Azospermia (factor b), Azospermia (factor c), or 1p36 deletion. In other embodiments, the P conditions that can be determined in one or more fetal cells include acute lymphoblastic leukemia, acute or chronic lymphocyctic or granulocytic tumor, acute myeloid leukemia, acute promyelocytic leukemia, adenocarcinoma, adenoma, adrenal cancer, basal cell carcinoma, bone cancer, brain cancer, breast cancer, bronchi cancer, cervical dysplasia, chronic myelogenous leukemia, colon cancer, epidermoid carcinoma, Ewing's sarcoma, gallbladder cancer, gallstone tumor, giant cell tumor, glioblastoma multiforma, hairy-cell tumor, head cancer, hyperplasia, hyperplastic corneal nerve tumor, in situ carcinoma, intestinal ganglioneuroma, islet cell tumor, Kaposi's sarcoma, kidney cancer, larynx cancer, leiomyomater tumor, liver cancer, lung cancer, lymphomas, malignant carcinoid, malignant hypercalcemia, malignant melanomas, marfanoid habitus tumor, medullary carcinoma, metastatic skin carcinoma, mucosal neuromas, mycosis fungoide, myelodysplastic syndrome, myeloma, neck cancer, neural tissue cancer, neuroblastoma, osteogenic sarcoma, osteosarcoma, ovarian tumor, pancreas cancer, parathyroid cancer, pheochromocytoma, polycythemia vera, primary brain tumor, prostate cancer, rectum cancer, renal cell tumor, retinoblastoma, rhabdomyosarcoma, seminoma, skin cancer, small-cell lung tumor, soft tissue sarcoma, squamous cell carcinoma, stomach cancer, thyroid cancer, topical skin lesion, veticulum cell sarcoma, or Wilm's tumor.

In some embodiments, the step of enriching a sample for a cell type includes flowing a sample or a fraction of a sample through an array of obstacles that separate the cells according to size by selectively directing cells of a predetermined size into a first outlet and directing cells of another predetermined size to a second outlet, and flowing the sample or sample fraction through one or more magnetic fields that retain paramagnetic components. The method further comprises ejecting the nuclei from the cells in the sample by applying hyperbaric or hypobaric pressure to the sample, and flowing the sample or a sample fraction through an array of obstacles that are coated with binding moieties that bind one or more cell populations in the sample. The binding moieties of this and other disclosed methods can be any known in the art and may be selected from the group consisting of antibodies, receptors, ligands, proteins, nucleic acids, sugars, carbohydrates and combinations thereof.

In some embodiments, the methods of the invention can be used to determine a fetal abnormality from amniotic fluid obtained from a pregnant female. In these embodiments, an amniotic fluid sample is obtained from the pregnant female and is enriched for fetal cells. Subsequently, one or more nucleic acid molecules are obtained from the enriched cells, and are amplified on a bead. Up to 100 bases of the nucleic acid are obtained, and in some embodiments up to one million copies of the nucleic acid are amplified. The amplified nucleic acids can also be sequenced. Preferably, the nucleic acid is genomic DNA.

In some embodiments, the fetal abnormality can be determined from a sample that is obtained from a pregnant female and enriched for fetal cells by subjecting the sample to the enrichment procedure that includes separating cells according size, and flowing it through a magnetic field. The size-based separation involves flowing the sample through an array of obstacles that directs cells of a size smaller than a predetermined size to a first outlet, and cells that are larger than a predetermined size to a second outlet. The enriched sample is also subjected to one or more magnetic fields and hyperbaric or hypobaric pressure, and in some embodiments it is used for genetic analyses including SNP detection, RNA expression detection and sequence detection. In some embodiments, one or more nucleic acid fragments can be obtained from the sample that has been subjected to the hyperbaric or hypobaric pressure, and the nucleic acid fragments can be amplified by methods including multiple displacement amplification (MDA), degenerate oligonucleotide primed PCR (DOP), primer extension pre-amplification (PEP) or improved-PEP (I-PEP).

In some embodiments, the method for determining a fetal abnormality can be performed using a blood sample obtained form a pregnant female. The sample can be enriched for fetal cells by flowing the sample through an array of obstacles that directs cells of a size smaller than a predetermined size to a first outlet, and cells that are larger than a predetermined size to a second outlet, and performing a genetic analysis e.g. SNP detection, RNA expression detection and sequence detection, on the enriched sample. The enriched sample can comprise one or more fetal cells and one or more nonfetal cells.

In some embodiments the invention includes kits providing the devices and reagents for performing one or all of the steps for determining the fetal abnormalities. These kits may include any of the devices or reagents disclosed singly or in combination.

In some embodiments, the genetic analysis of SNP detection or RNA expression can be performed using microarrays. SNP detection can also be accomplished using molecular inverted probes(s), and in some embodiments, SNP detection involves highly parallel detection of at least 100,000 SNPs. RNA expression detection can also involve highly parallel analysis of at least 10,000 transcripts. In some embodiments, sequence detection can involve determining the sequence of at least 50,000 bases per hour, and sequencing can be done in substantially real time or real time and can comprise adding a plurality of labeled nucleotides or nucleotide analogs to a sequence that is complementary to that of the enriched nucleic acid molecules, and detecting the incorporation. A variety of labels can be used in the sequence detection step and include chromophores, fluorescent moieties, enzymes, antigens, heavy metal, magnetic probes, dyes, phosphorescent groups, radioactive materials, chemiluminescent moieties, scattering or fluorescent nanoparticles, Raman signal generating moieties, and electrochemical detection moieties. Methods that include sequence detection can be accomplished using sequence by synthesis and they may include amplifying the nucleic acid on a bead. In some embodiments, the methods can include amplifying target nucleic acids from the enriched sample(s) by any method known in the art but preferably by multiple displacement amplification (MDA), degenerate oligonucleotide primed PCR (DOP), primer extension pre-amplification (PEP) or improved-PEP (I-PEP).

The genetic analyses can be performed on DNA of chromosomes X, Y, 13, 18 or 21 or on the RNA transcribed therefrom. In some embodiments, the genetic analyses can also be performed on a control sample or reference sample, and in some instances, the control sample can be a maternal sample.

SUMMARY OF THE DRAWINGS

FIG. 5 illustrates exemplary genes that can be analyzed from enriched cells, such as epithelial cells, endothelial cells, circulating tumor cells, progenitor cells, etc.

FIGS. 15A-15B illustrate cell smears of first and second outlet (e.g., product and waste) fractions.

FIG. 21 illustrates epithelial cells bound to obstacles and floor in a separation/enrichment module.

INCORPORATION BY REFERENCE

Figure 1A:
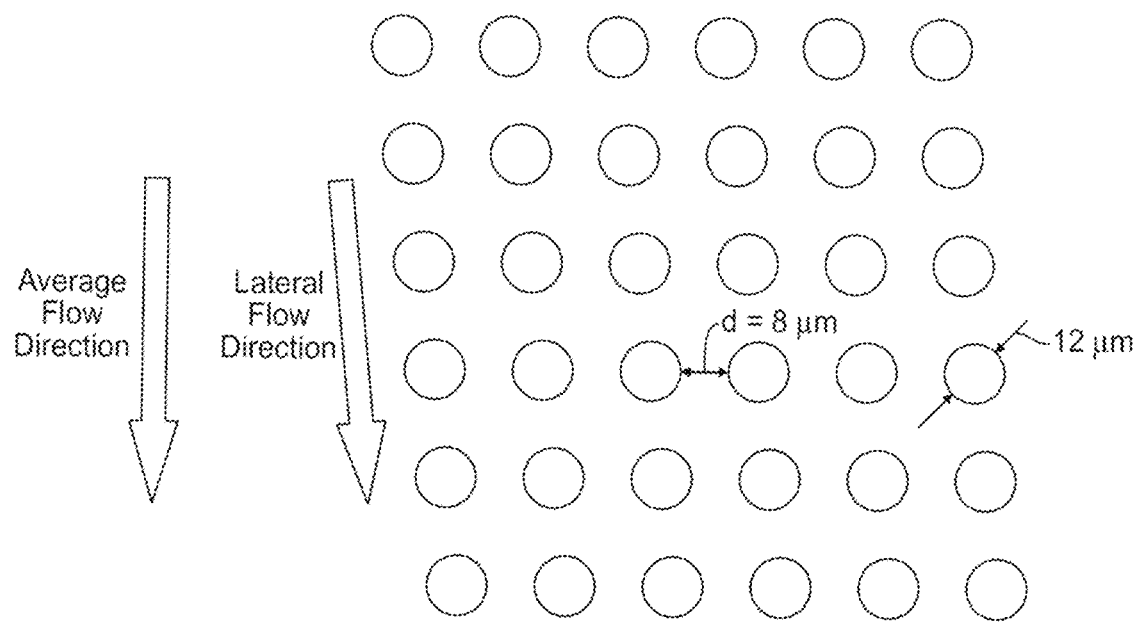
FIGS. 1A-1D illustrate embodiments of a size-based separation module.

All publications and patent applications mentioned in this specification are herein incorporated by reference to the same extent as if each individual publication or patent application was specifically and individually indicated to be incorporated by reference.

DETAILED DESCRIPTION OF THE INVENTION

The present invention provides systems, apparatus, and methods to detect the presence of or abnormalities of rare analytes or cells, such as hematapoeitic bone marrow pre-genetor cells, endothelial cells, fetal cells circulating in maternal peripheral blood, epithelial cells, or circulating tumor cells in a sample of a mixed analyte or cell population (e.g., maternal peripheral blood samples).

1. Sample Collection/Preparation

Samples containing rare cells can be obtained from any animal in need of a diagnosis or prognosis or from an animal pregnant with a fetus in need of a diagnosis or prognosis. In one example, a sample can be obtained from animal suspected of being pregnant, pregnant, or that has been pregnant to detect the presence of a fetus or fetal abnormality. In another example, a sample is obtained from an animal suspected of having, having, or an animal that had a disease or condition (e.g. cancer). Such condition can be diagnosed, prognosed, monitored and therapy can be determined based on the methods and systems herein. Animal of the present invention can be a human or a domesticated animal such as a cow, chicken, pig, horse, rabbit, dogs, cat, or goat. Samples derived from an animal or human can include, e.g., whole blood, sweat, tears, ear flow, sputum, lymph, bone marrow suspension, lymph, urine, saliva, semen, vaginal flow, cerebrospinal fluid, brain fluid, ascites, milk, secretions of the respiratory, intestinal or genitourinary tracts fluid.

To obtain a blood sample, any technique known in the art may be used, e.g. a syringe or other vacuum suction device. A blood sample can be optionally pre-treated or processed prior to enrichment. Examples of pre-treatment steps include the addition of a reagent such as a stabilizer, a preservative, a fixant, a lysing reagent, a diluent, an anti-apoptotic reagent, an anti-coagulation reagent, an anti-thrombotic reagent, magnetic property regulating reagent, a buffering reagent, an osmolality regulating reagent, a pH regulating reagent, and/or a cross-linking reagent.

When a blood sample is obtained, a preservative such an anti-coagulation agent and/or a stabilizer is often added to the sample prior to enrichment. This allows for extended time for analysis/detection. Thus, a sample, such as a blood sample, can be enriched and/or analyzed under any of the methods and systems herein within 1 week, 6 days, 5 days, 4 days, 3 days, 2 days, 1 day, 12 hrs, 6 hrs, 3 hrs, 2 hrs, or 1 hr from the time the sample is obtained.

In some embodiments, a blood sample can be combined with an agent that selectively lyses one or more cells or components in a blood sample. For example, fetal cells can be selectively lysed releasing their nuclei when a blood sample including fetal cells is combined with deionized water. Such selective lysis allows for the subsequent enrichment of fetal nuclei using, e.g., size or affinity based separation. In another example platelets and/or enucleated red blood cells are selectively lysed to generate a sample enriched in nucleated cells, such as fetal nucleated red blood cells (fnRBC's), maternal nucleated blood cells (mnBC), epithelial cells and circulating tumor cells. fnRBC's can be subsequently separated from mnBC's using, e.g., antigen-i affinity or differences in hemoglobin When obtaining a sample from an animal (e.g., blood sample), the amount can vary depending upon animal size, its gestation period, and the condition being screened. In some embodiments, up to 50, 40, 30, 20, 10, 9, 8, 7, 6, 5, 4, 3, 2, or 1 mL of a sample is obtained. In some embodiments, 1-50, 2-40, 3-30, or 4-20 mL of sample is obtained. In some embodiments, more than 5, 10, 15, 20, 25, 30, 35, 40, 45, 50, 55, 60, 65, 70, 75, 80, 85, 90, 95 or 100 mL of a sample is obtained.

To detect fetal abnormality, a blood sample can be obtained from a pregnant animal or human within 36, 24, 22, 20, 18, 16, 14, 12, 10, 8, 6 or 4 weeks of gestation or even after a pregnancy has terminated.

II. Enrichment

A sample (e.g. blood sample) can be enriched for rare analytes or rare cells (e.g. fetal cells, epithelial cells or circulating tumor cells) using one or more any methods known in the art (e.g. Guetta, E M et al. Stem Cells Dev, 13(1):93-9 (2004)) or described herein. The enrichment increases the concentration of rare cells or ratio of rare cells to non-rare cells in the sample. For example, enrichment can increase concentration of an analyte of interest such as a fetal cell or epithelial cell or circulating tumor cell (CTC) by a factor of at least 2, 4, 6, 8, 10, 20, 50, 100, 200, 500, 1,000, 2,000, 5,000, 10,000, 20,000, 50,000, 100,000, 200,000, 500,000, 1,000,000, 2,000,000, 5,000,000, 10,000,000, 20,000,000, 50,000,000, 100,000,000, 200,000,000, 500,000,000, 1,000,000,000, 2,000,000,000, or 5,000,000,000 fold over its concentration in the original sample. In particular, when enriching fetal cells from a maternal peripheral venous blood sample, the initial concentration of the fetal cells may be about 1:50,000,000 and it may be increased to at least 1:5,000 or 1:500. Enrichment can also increase concentration of rare cells in volume of rare cells/total volume of sample (removal of fluid). A fluid sample (e.g., a blood sample) of greater than 10, 15, 20, 50, or 100 mL total volume comprising rare components of interest, and it can be concentrated such that the rare component of interest into a concentrated solution of less than 0.5, 1, 2, 3, 5, or 10 mL total volume.

Enrichment can occur using one or more types of separation modules. Several different modules are described herein, all of which can be fluidly coupled with one another in the series for enhanced performance.

In some embodiments, enrichment occurs by selective lysis as described above.

In one embodiment, enrichment of rare cells occurs using one or more size-based separation modules. Examples of size-based separation modules include filtration modules, sieves, matrixes, etc. Examples of size-based separation modules contemplated by the present invention include those disclosed in International Publication No. WO 2004/113877. Other size based separation modules are disclosed in International Publication No. WO 2004/0144651.

In some embodiments, a size-based separation module comprises one or more arrays of obstacles forming a network of gaps. The obstacles are configured to direct particles as they flow through the array/network of gaps into different directions or outlets based on the particle's hydrodynamic size. For example, as a blood sample flows through an array of obstacles, nucleated cells or cells having a hydrodynamic size larger than a predetermined size, e.g., 8 microns, are directed to a first outlet located on the opposite side of the array of obstacles from the fluid flow inlet, while the enucleated cells or cells having a hydrodynamic size smaller than a predetermined size, e.g., 8 microns, are directed to a second outlet also located on the opposite side of the array of obstacles from the fluid flow inlet.

An array can be configured to separate cells smaller or larger than a predetermined size by adjusting the size of the gaps, obstacles, and offset in the period between each successive row of obstacles. For example, in some embodiments, obstacles or gaps between obstacles can be up to 10, 20, 50, 70, 100, 120, 150, 170, or 200 microns in length or about 2, 4, 6, 8 or 10 microns in length. In some embodiments, an array for size-based separation includes more than 100, 500, 1,000, 5,000, 10,000, 50,000 or 100,000 obstacles that are arranged into more than 10, 20, 50, 100, 200, 500, or 1000 rows. Preferably, obstacles in a first row of obstacles are offset from a previous (upstream) row of obstacles by up to 50% the period of the previous row of obstacles. In some embodiments, obstacles in a first row of obstacles are offset from a previous row of obstacles by up to 45, 40, 35, 30, 25, 20, 15 or 10% the period of the previous row of obstacles. Furthermore, the distance between a first row of obstacles and a second row of obstacles can be up to 10, 20, 50, 70, 100, 120, 150, 170 or 200 microns. A particular offset can be continuous (repeating for multiple rows) or non-continuous. In some embodiments, a separation module includes multiple discrete arrays of obstacles fluidly coupled such that they are in series with one another. Each array of obstacles has a continuous offset. But each subsequent (downstream) array of obstacles has an offset that is different from the previous (upstream) offset. Preferably, each subsequent array of obstacles has a smaller offset that the previous array of obstacles. This allows for a refinement in the separation process as cells migrate through the array of obstacles. Thus, a plurality of arrays can be fluidly coupled in series or in parallel, (e.g., more than 2, 4, 6, 8, 10, 20, 30, 40, 50). Fluidly coupling separation modules (e.g., arrays) in parallel allows for high-throughput analysis of the sample, such that at least 1, 2, 5, 10, 20, 50, 100, 200, or 500 mL per hour flows through the enrichment modules or at least 1, 5, 10, or 50 million cells per hour are sorted or flow through the device.

FIG. 1A illustrates an example of a size-based separation module. Obstacles (which may be of any shape) are coupled to a flat substrate to form an array of gaps. A transparent cover or lid may be used to cover the array. The obstacles form a two-dimensional array with each successive row shifted horizontally with respect to the previous row of obstacles, where the array of obstacles directs component having a hydrodynamic size smaller than a predetermined size in a first direction and component having a hydrodynamic size larger that a predetermined size in a second direction. For enriching epithelial or circulating tumor cells from enucleated, the predetermined size of an array of obstacles can be get at 6-12 µm or 6-8 µm. For enriching fetal cells from a mixed sample (e.g. maternal blood sample) the predetermined size of an array of obstacles can be get at between 4-10 pun or 6-8 µm. The flow of sample into the array of obstacles can be aligned at a small angle (flow angle) with respect to a line-of-sight of the array. Optionally, the array is coupled to an infusion pump to perfuse the sample through the obstacles. The flow conditions of the size-based separation module described herein are such that cells are sorted by the array with minimal damage. This allows for downstream analysis of intact cells and intact nuclei to be more efficient and reliable.

Figure 1B:
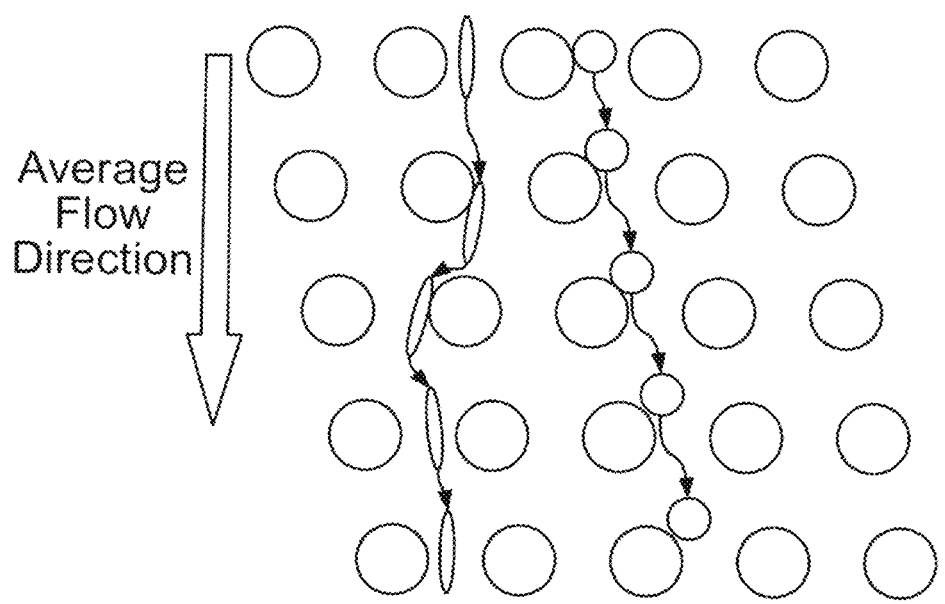
Figure 1C:
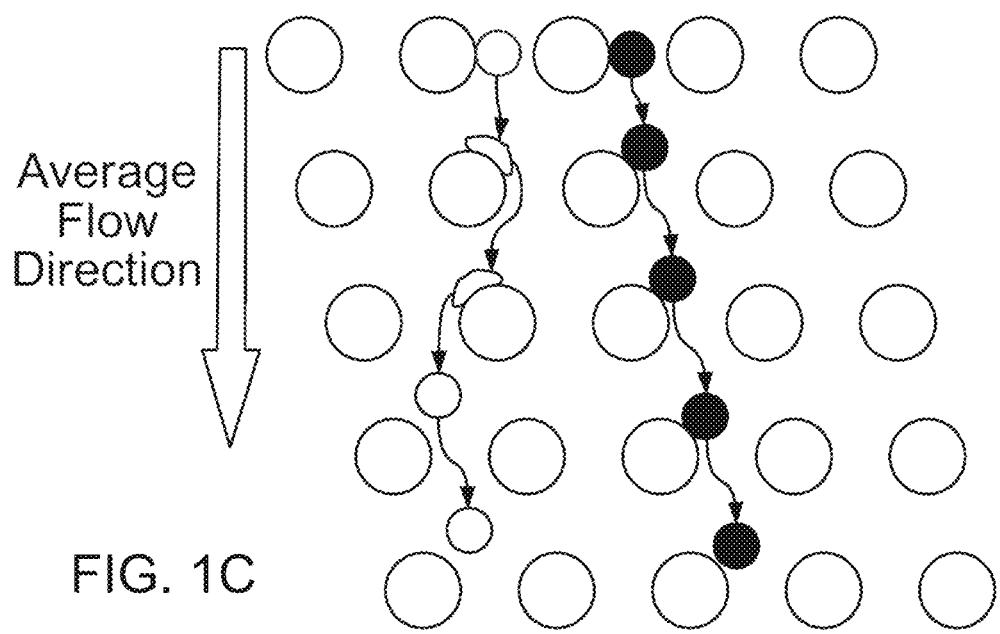
Figure 1D:
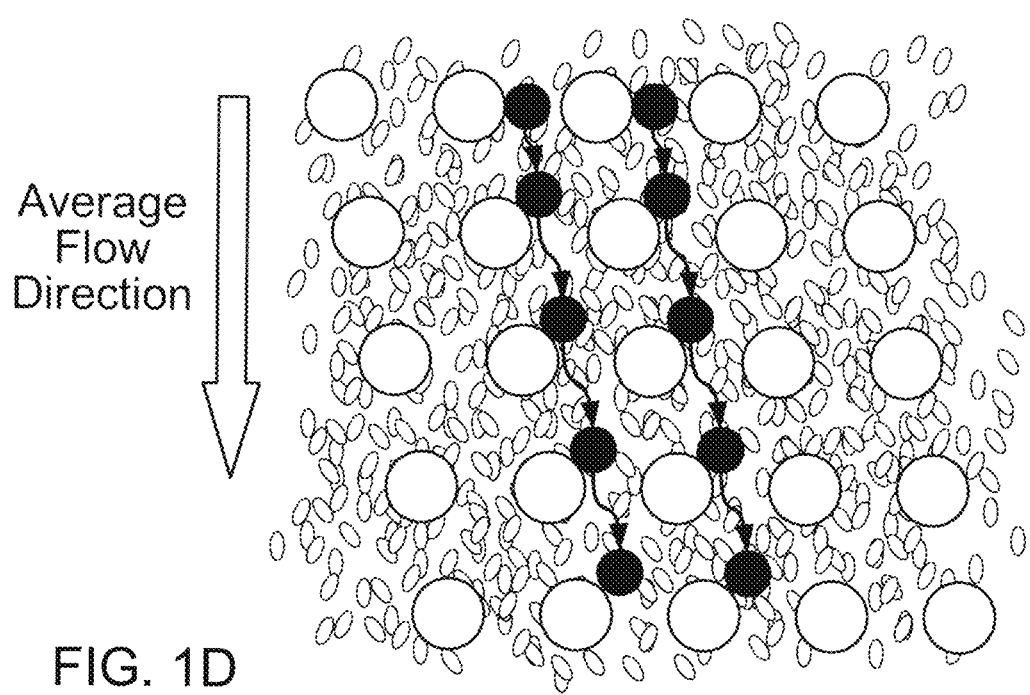

In some embodiments, a size-based separation module comprises an array of obstacles configured to direct cells larger than a predetermined size to migrate along a line-of-sight within the array (e.g. towards a first outlet or bypass channel leading to a first outlet), while directing cells and analytes smaller than a predetermined size to migrate through the array of obstacles in a different direction than the larger cells (e.g. towards a second outlet). Such embodiments are illustrated in part in FIGS. 1B-ID.

A variety of enrichment protocols may be utilized although gentle handling of the cells is preferred to reduce any mechanical damage to the cells or their DNA. This gentle handling may serve to preserve the small number of fetal cells in the sample. Integrity of the nucleic acid being evaluated is an important feature to permit the distinction between the genomic material from the fetal cells and other cells in the sample. In particular, the enrichment and separation of the fetal cells using the arrays of obstacles produces gentle treatment which minimizes cellular damage and maximizes nucleic acid integrity permitting exceptional levels of separation and the ability to subsequently utilize various formats to very accurately analyze the genome of the cells which are present in the sample in extremely low numbers.

In some embodiments, enrichment of rare cells (e.g. fetal cells, epithelial cells or circulating tumor cells) occurs using one or more capture modules that selectively inhibit the mobility of one or more cells of interest. Preferably, a capture module is fluidly coupled downstream to a size-based separation module. Capture modules can include a substrate having multiple obstacles that restrict the movement of cells or analytes greater than a predetermined size. Examples of capture modules that inhibit the migration of cells based on size are disclosed in U.S. Pat. Nos. 5,837,115 and 6,692,952.

In some embodiments, a capture module includes a two dimensional array of obstacles that selectively filters or captures cells or analytes having a hydrodynamic size greater than a particular gap size (predetermined size), International Publication No. WO 2004/113877.

In some cases a capture module captures analytes (e.g., cells of interest or not of interest) based on their affinity. For example, an affinity-based separation module that can capture cells or analytes can include an array of obstacles adapted for permitting sample flow through, but for the fact that the obstacles are covered with binding moieties that selectively bind one or more analytes (e.g., cell populations) of interest (e.g., red blood cells, fetal cells, epithelial cells or nucleated cells) or analytes not-of-interest (e.g., white blood cells). Arrays of obstacles adapted for separation by capture can include obstacles having one or more shapes and can be arranged in a uniform or non-uniform order. In some embodiments, a two-dimensional array of obstacles is staggered such that each subsequent row of obstacles is offset from the previous row of obstacles to increase the number of interactions between the analytes being sorted (separated) and the obstacles.

Binding moieties coupled to the obstacles can include e.g., proteins (e.g., ligands/receptors), nucleic acids having complementary counterparts in retained analytes, antibodies, etc. In some embodiments, an affinity-based separation module comprises a two-dimensional array of obstacles covered with one or more antibodies selected from the group consisting of: anti-CD71, anti-CD235a, anti-CD36, anti-carbohydrates, anti-selectin, anti-CD45, anti-GPA, anti-antigen-i, anti-EpCAM, anti-E-cadherin, and anti-Muc-1.

Figure 2A:
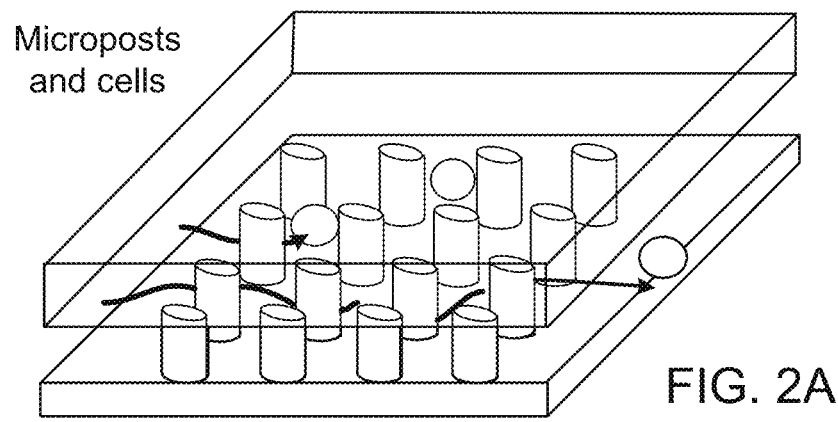
FIGS. 2A-2C illustrate one embodiment of an affinity separation module.
Figure 2B:
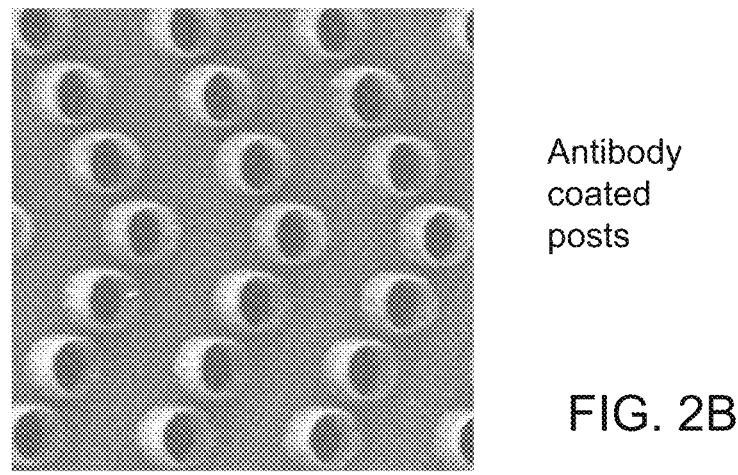
Figure 2C:
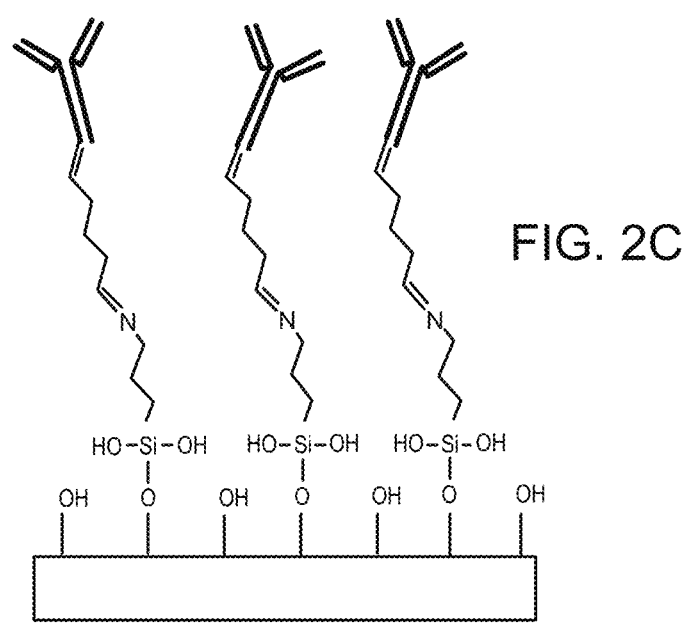

FIG. 2A illustrates a path of a first analyte through an array of posts wherein an analyte that does not specifically bind to a post continues to migrate through the array, while an analyte that does bind a post is captured by the array. FIG. 2B is a picture of antibody coated posts. FIG. 2C illustrates coupling of antibodies to a substrate (e.g., obstacles, side walls, etc.) as contemplated by the present invention. Examples of such affinity-based separation modules are described in International Publication No. WO 2004/029221.

In some embodiments, a capture module utilizes a magnetic field to separate and/or enrich one or more analytes (cells) based on a magnetic property or magnetic potential in such analyte of interest or an analyte not of interest. For example, red blood cells which are slightly diamagnetic (repelled by magnetic field) in physiological conditions can be made paramagnetic (attributed by magnetic field) by deoxygenation of the hemoglobin into methemoglobin. This magnetic property can be achieved through physical or chemical treatment of the red blood cells. Thus, a sample containing one or more red blood cells and one or more white blood cells can be enriched for the red blood cells by first inducing a magnetic property in the red blood cells and then separating the red blood cells from the white blood cells by flowing the sample through a magnetic field (uniform or non-uniform).

For example, a maternal blood sample can flow first through a size-based separation module to remove enucleated cells and cellular components (e.g., analytes having a hydrodynamic size less than 6 µms) based on size. Subsequently, the enriched nucleated cells (e.g., analytes having a hydrodynamic size greater than 6 µms) white blood cells and nucleated red blood cells are treated with a reagent, such as $CO_2$, $N_2$, or $NaNO_2$, that changes the magnetic property of the red blood cells' hemoglobin. The treated sample then flows through a magnetic field (e.g., a column coupled to an external magnet), such that the paramagnetic analytes (e.g., red blood cells) will be captured by the magnetic field while the white blood cells and any other non-red blood cells will flow through the device to result in a sample enriched in nucleated red blood cells (including fetal nucleated red blood cells or fnRBC's). Additional examples of magnetic separation modules are described in U.S. application Ser. No. 11/323,971, filed Dec. 29, 2005 entitled "Devices and Methods for Magnetic Enrichment of Cells and Other Particles" and U.S. application Ser. No. 11/227,904, filed Sep. 15, 2005, entitled "Devices and Methods for Enrichment and Alteration of Cells and Other Particles".

Subsequent enrichment steps can be used to separate the rare cells (e.g. fnRBC's) from the non-rare cells maternal nucleated red blood cells. In some embodiments, a sample enriched by size-based separation followed by affinity/ magnetic separation is further enriched for rare cells using fluorescence activated cell sorting (FACS) or selective lysis of a subset of the cells.

In some embodiments, enrichment involves detection and/or isolation of rare cells or rare DNA (e.g. fetal cells or fetal DNA) by selectively initiating apoptosis in the rare cells. This can be accomplished, for example, by subjecting a sample that includes rare cells (e.g. a mixed sample) to hyperbaric pressure (increased levels of $CO_2$; e.g. 4% $CO_2$). This will selectively initiate condensation and/or apoptosis in the rare or fragile cells in the sample (e.g. fetal cells). Once the rare cells (e.g. fetal cells) begin apoptosis, their nuclei will condense and optionally be ejected from the rare cells. At that point, the rare cells or nuclei can be detected using any technique known in the art to detect condensed nuclei, including DNA gel electropheresis, in situ labeling fluorescence labeling, and in situ labeling of DNA nicks using terminal deoxynucleotidyl transferase (TdT)-mediated dUTP in situ nick labeling (TUNEL) (Gavrieli, Y., et al. J. Cell Biol. 119:493-501 (1992)), and ligation of DNA strand breaks having one or two-base 3' overhangs (Taq polymerase-based in situ ligation). (Didenko V., et al. J. Cell Biol. 135:1369-76 (1996)).

In some embodiments ejected nuclei can further be detected using a size based separation module adapted to selectively enrich nuclei and other analytes smaller than a predetermined size (e.g. 6 microns) and isolate them from cells and analytes having a hydrodynamic diameter larger than 6 microns. Thus, in one embodiment, the present invention contemplated detecting fetal cells/fetal DNA and optionally using such fetal DNA to diagnose or prognose a condition in a fetus. Such detection and diagnosis can occur by obtaining a blood sample from the female pregnant with the fetus, enriching the sample for cells and analytes larger than 8 microns using, for example, an array of obstacles adapted for size-base separation where the predetermined size of the separation is 8 microns (e.g. the gap between obstacles is up to 8 microns). Then, the enriched product is further enriched for red blood cells (RBC's) by oxidizing the sample to make the hemaglobin paramagnetic and flowing the sample through one or more magnetic regions. This selectively captures the RBC's and removes other cells (e.g. white blood cells) from the sample. Subsequently, the fnRBC's can be enriched from mnRBC's in the second enriched product by subjecting the second enriched product to hyperbaric or hypobaric pressure or other stimulus that selectively causes the fetal cells to begin apoptosis and condense/eject their nuclei. Such condensed nuclei are then identified/isolated using e.g. laser capture microdissection or a size based separation module that separates components smaller than 3, 4, 5 or 6 microns from a sample. Such fetal nuclei can then by analyzed using any method known in the art or described herein.

In some embodiments, when the analyte desired to be separated (e.g., red blood cells or white blood cells) is not ferromagnetic or does not have a potential magnetic property, a magnetic particle (e.g., a bead) or compound (e.g., $Fe^{3+}$) can be coupled to the analyte to give it a magnetic property. In some embodiments, a bead coupled to an antibody that selectively binds to an analyte of interest can be decorated with an antibody elected from the group of anti CD71 or CD75. In some embodiments a magnetic compound, such as $Fe^{3+}$, can be couple to an antibody such as those described above. The magnetic particles or magnetic antibodies herein may be coupled to any one or more of the devices herein prior to contact with a sample or may be mixed with the sample prior to delivery of the sample to the device(s). Magnetic particles can also be used to decorate one or more analytes (cells of interest or not of interest) to increase the size prior to performing size-based separation.

Magnetic field used to separate analytes/cells in any of the embodiments herein can uniform or non-uniform as well as external or internal to the device(s) herein. An external magnetic field is one whose source is outside a device herein (e.g., container, channel, obstacles). An internal magnetic field is one whose source is within a device contemplated herein. An example of an internal magnetic field is one where magnetic particles may be attached to obstacles present in the device (or manipulated to create obstacles) to increase surface area for analytes to interact with to increase the likelihood of binding. Analytes captured by a magnetic field can be released by demagnetizing the magnetic regions retaining the magnetic particles. For selective release of analytes from regions, the demagnetization can be limited to selected obstacles or regions. For example, the magnetic field can be designed to be electromagnetic, enabling turn-on and turn-off off the magnetic fields for each individual region or obstacle at will.

Figure 3:
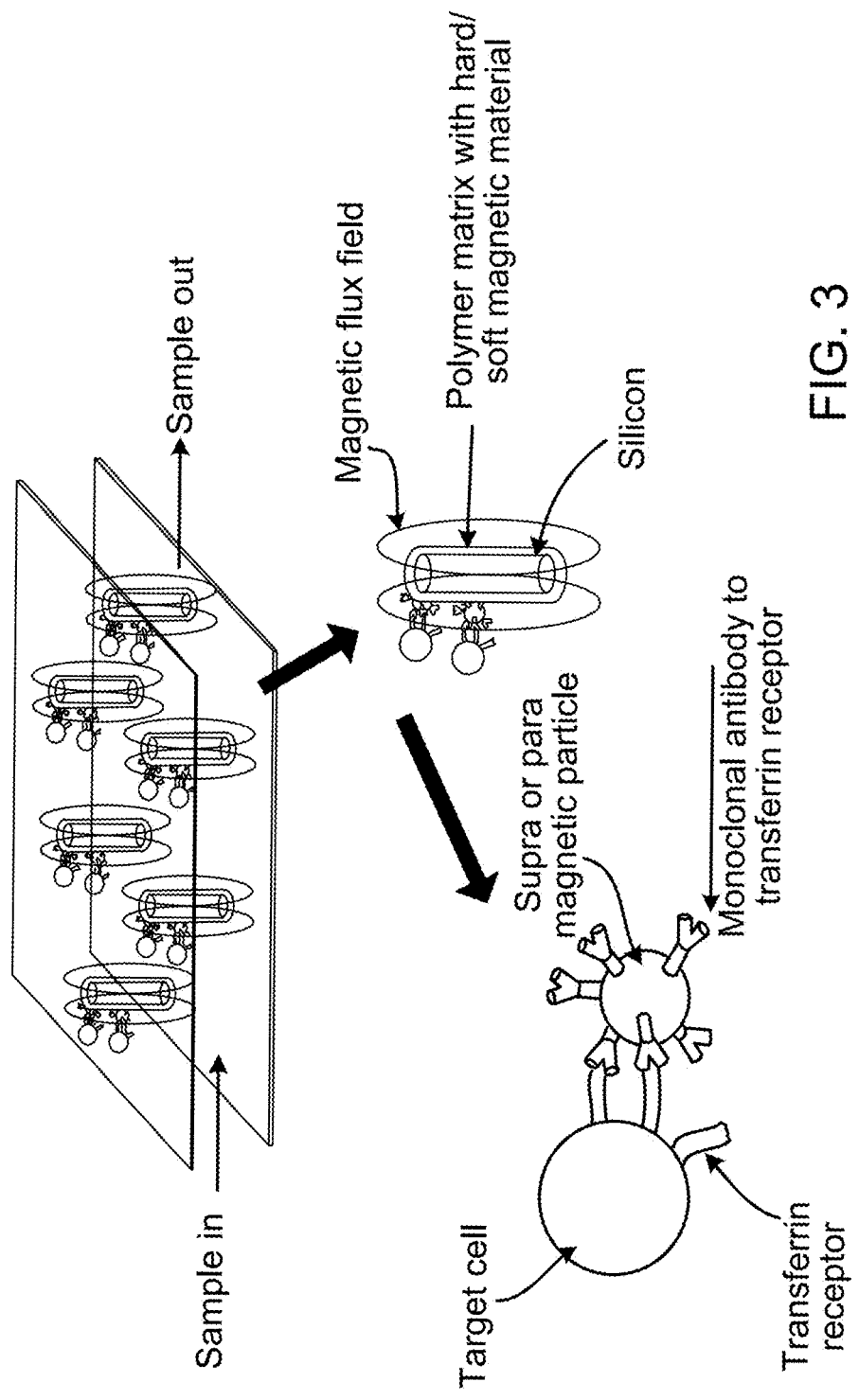
FIG. 3 illustrate one embodiment of a magnetic separation module.

FIG. 3 illustrates an embodiment of a device configured for capture and isolation of cells expressing the transferrin receptor from a complex mixture. Monoclonal antibodies to CD71 receptor are readily available off-the-shelf and can be covalently coupled to magnetic materials, such as, but not limited to any ferroparticles including but not limited to ferrous doped polystyrene and ferroparticles or ferro-colloids (e.g., from Miltenyi and Dynal). The anti CD71 bound to magnetic particles is flowed into the device. The antibody coated particles are drawn to the obstacles (e.g., posts), floor, and walls and are retained by the strength of the magnetic field interaction between the particles and the magnetic field. The particles between the obstacles and those loosely retained with the sphere of influence of the local magnetic fields away from the obstacles are removed by a rinse.

Figure 4:
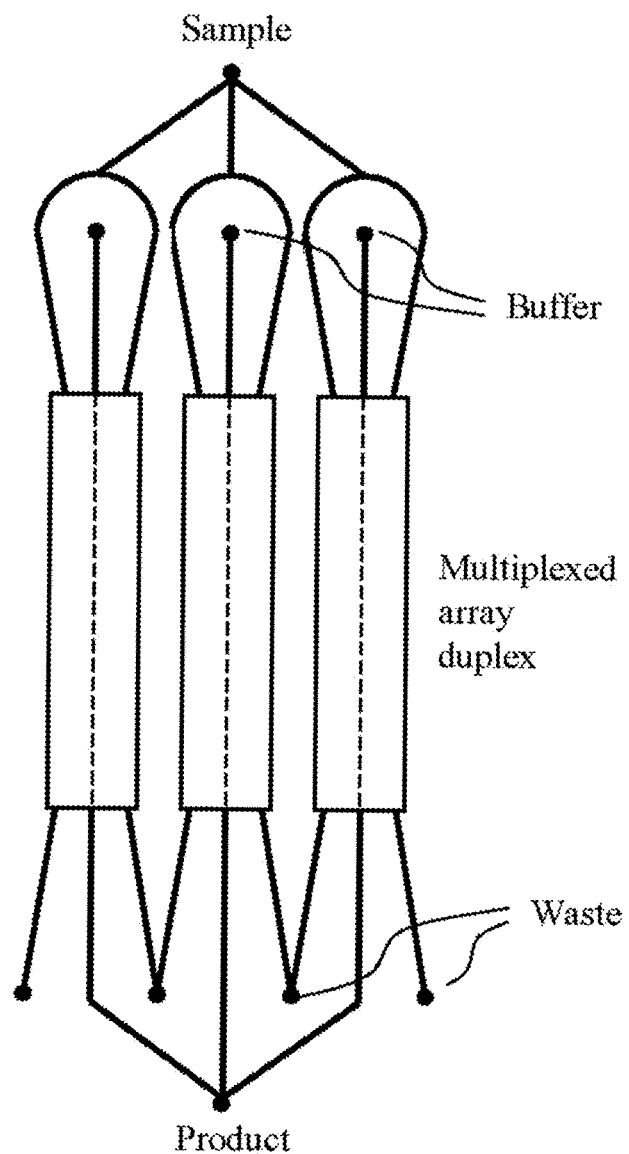
FIG. 4 illustrates one example of a multiplex enrichment module of the present invention.

In some cases, a fluid sample such as a blood sample is first flowed through one or more size-base separation module. Such modules may be fluidly connected in series and/or in parallel. FIG. 4 illustrates one embodiment of three size-based enrichment modules that are fluidly coupled in parallel. The waste (e.g., cells having hydrodynamic size less than 4 microns) are directed into a first outlet and the product (e.g., cells having hydrodynamic size greater than 4 microns) are directed to a second outlet. The product is subsequently enriched using the inherent magentic property of hemoglobin. The product is modified (e.g., by addition of one or more reagents) such that the hemoglobin in the red blood cells becomes paramagentic. Subsequently, the product is flowed through one or more magentic fields. The cells that are trapped by the magentic field are subsequently analyzed using the one or more methods herein.

One or more of the enrichment modules herein (e.g., size-based separation module(s) and capture module(s)) may be fluidly coupled in series or in parallel with one another. For example a first outlet from a separation module can be fluidly coupled to a capture module. In some embodiments, the separation module and capture module are integrated such that a plurality of obstacles acts both to deflect certain analytes according to size and direct them in a path different than the direction of analyte(s) of interest, and also as a capture module to capture, retain, or bind certain analytes based on size, affinity, magnetism or other physical property.

In any of the embodiments herein, the enrichment steps performed have a specificity and/or sensitivity greater than 50, 60, 70, 80, 90, 95, 96, 97, 98, 99, 99.1, 99.2, 99.3, 99.4, 99.5, 99.6, 99.7, 99.8, 99.9 or 99.95% The retention rate of the enrichment module(s) herein is such that ≥50, 60, 70, 80, 90, 91, 92, 93, 94, 95, 96, 97, 98, 99, or 99.9% of the analytes or cells of interest (e.g., nucleated cells or nucleated red blood cells or nucleated from red blood cells) are retained. Simultaneously, the enrichment modules are configured to remove ≥50, 60, 70, 80, 85, 90, 91, 92, 93, 94, 95, 96, 97, 98, 99, or 99.9% of all unwanted analytes (e.g., red blood-platelet enriched cells) from a sample.

For example, in some embodiments the analytes of interest are retained in an enriched solution that is less than 50, 40, 30, 20, 10, 9.0, 8.0, 7.0, 6.0, 5.0, 4.5, 4.0, 3.5, 3.0, 2.5, 2.0, 1.5, 1.0, or 0.5 fold diluted from the original sample. In some embodiments, any or all of the enrichment steps increase the concentration of the analyte of interest (fetal cell), for example, by transferring them from the fluid sample to an enriched fluid sample (sometimes in a new fluid medium, such as a buffer).

III. Sample Analysis

In some embodiments, the methods herein are used for detecting the presence or conditions of rare cells that are in a mixed sample (optionally even after enrichment) at a concentration of up to 90%, 80%, 70%, 60%, 50%, 40%, 30%, 20%, 10%, 5% or 1% of all cells in the mixed sample, or at a concentration of less than 1:2, 1:4, 1:10, 1:50, 1:100, 1:200, 1:500, 1:1000, 1.2000, 1:5000, 1:10,000, 1:20,000, 1:50,000, 1:100,000, 1:200,000, 1:1,000,000, 1:2,000,000, 1:5,000,000, 1:10,000,000, 1:20,000,000, 1:50,000,000 or 1:100,000,000 of all cells in the sample, or at a concentration of less than $1 \times 10^{-3}$, $1 \times 10^{-4}$, $1 \times 10^{-5}$, $1 \times 10^{-6}$, or $1 \times 10^{-7}$ cells/μL of a fluid sample. In some embodiments, the mixed sample has a total of up to 2, 3, 4, 5, 6, 7, 8, 9, 10, 15, 20, 30, 40, 50, or 100 rare cells.

The rare cells can be, for example, fetal cells derived from a maternal sample (e.g., blood sample), or epithelial, endothelial, CTC's or other cells derived from an animal to be diagnosed.

Figure 31:
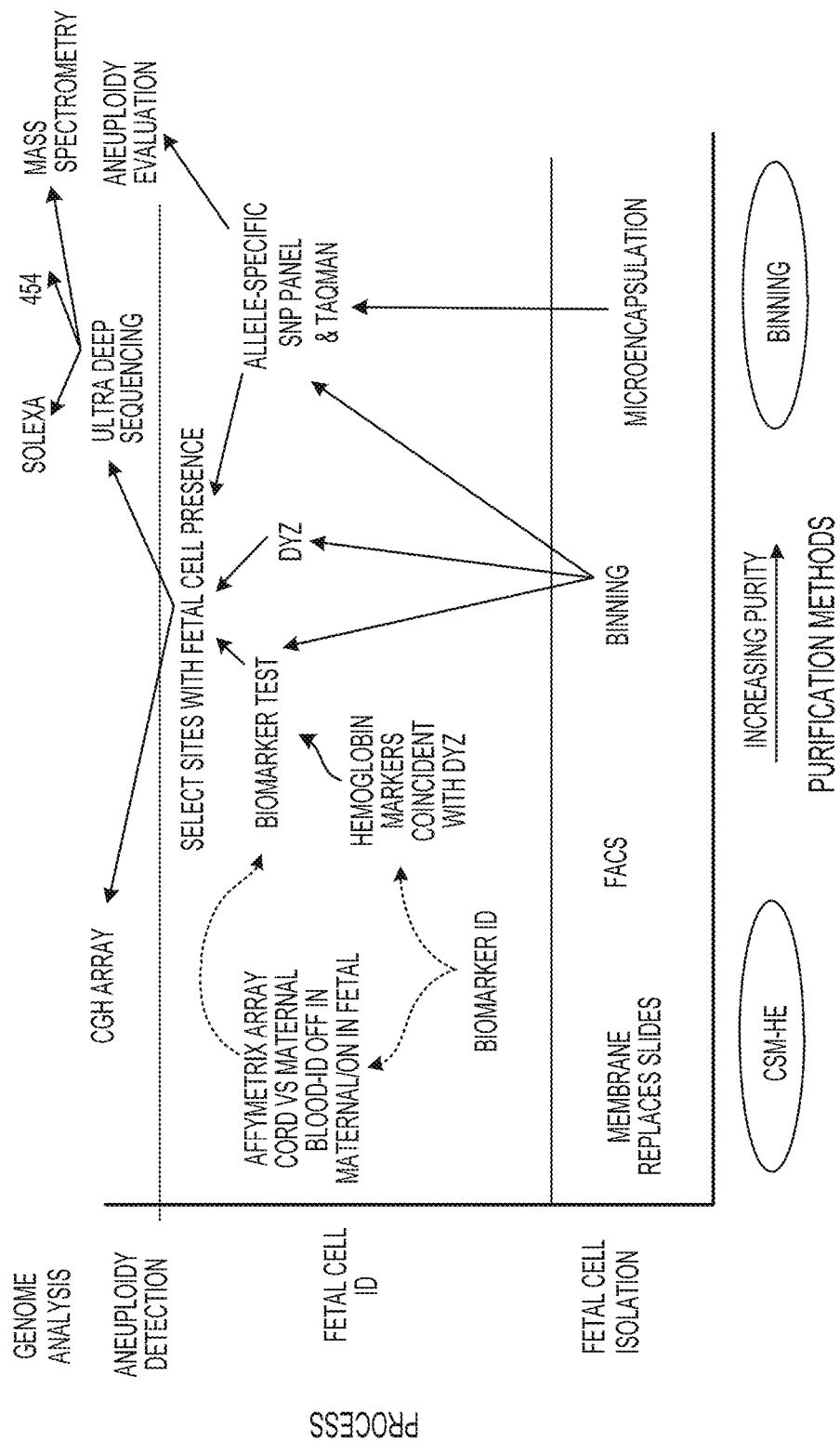
FIG. 31 illustrates methods of fetal diagnostic assays. Fetal cells are isolated by CSM-HE enrichment of target cells from blood. The designation of the fetal cells may be confirmed using techniques comprising FISH staining (using slides or membranes and optionally an automated detector), FACS, and/or binning. Binning may comprise distribution of enriched cells across wells in a plate (such as a 96 or 384 well plate), microencapsulation of cells in droplets that are separated in an emulsion, or by introduction of cells into microarrays of nanofluidic bins. Fetal cells are then identified using methods that may comprise the use of biomarkers (such as fetal (gamma) hemoglobin), allele-specific SNP panels that could detect fetal genome DNA, detection of differentially expressed maternal and fetal transcripts (such as Affymetrix chips), or primers and probes directed to fetal specific loci (such as the multi-repeat DYZ locus on the Y-chromosome). Binning sites that contain fetal cells are then be analyzed for aneuploidy and/or other genetic defects using a technique such as CGH array detection, ultra deep sequencing (such as Solexa, 454, or mass spectrometry), STR analysis, or SNP detection.
Figure 32:
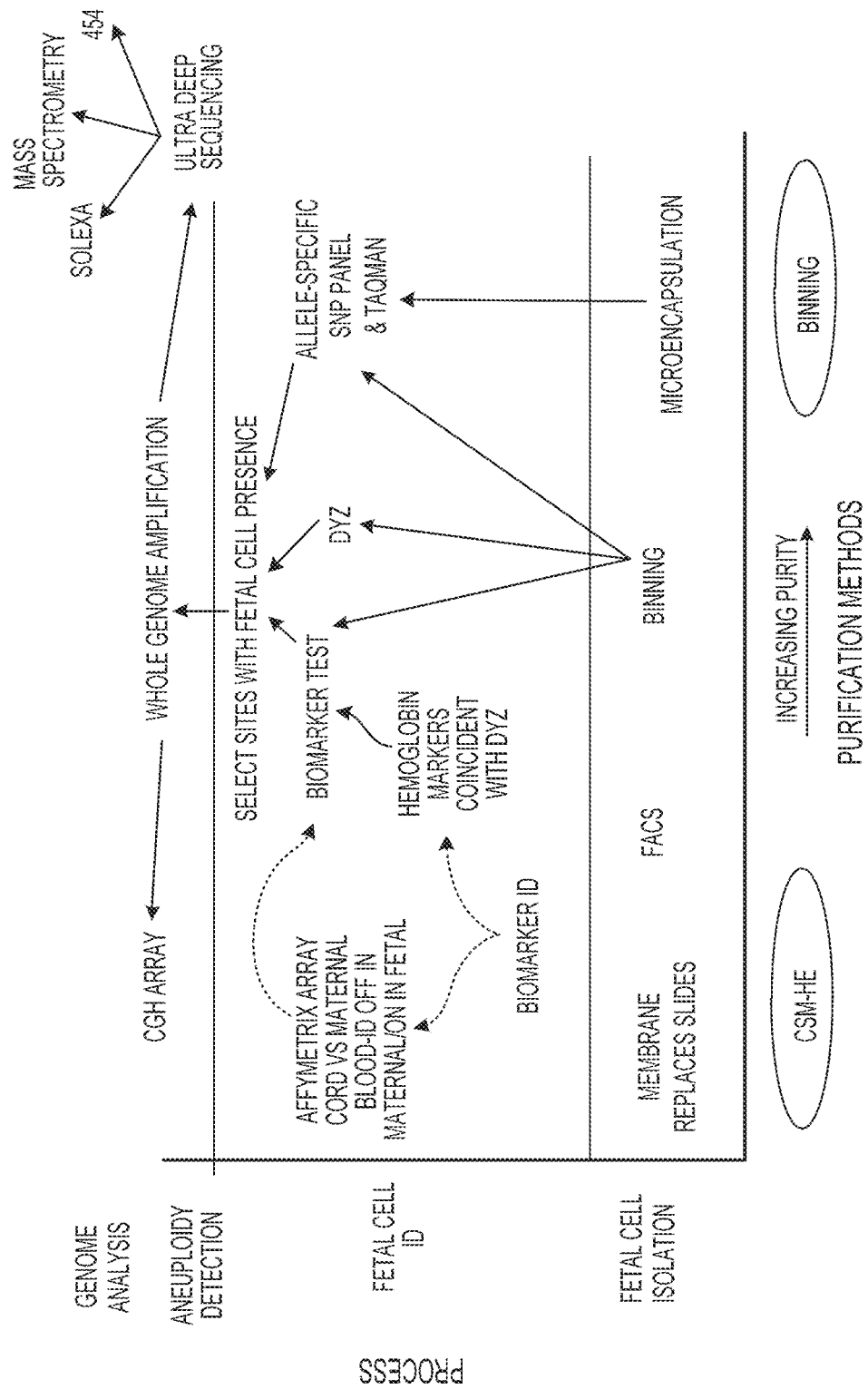
FIG. 32 illustrates methods of fetal diagnostic assays, further comprising the step of whole genome amplification prior to analysis of aneuploidy and/or other genetic defects.

Enriched target cells (e.g., fnRBC) can be "binned" prior to analysis of the enriched cells (FIGS. 31 and 32). Binning is any process which results in the reduction of complexity and/or total cell number of the enriched cell output. Binning may be performed by any method known in the art or described herein. One method of binning the enriched cells is by serial dilution. Such dilution may be carried out using any appropriate platform (e.g., PCR wells, microtiter plates). Other methods include nanofluidic systems which separate samples into droplets (e.g., BioTrove, Raindance, Fluidigm). Such nanofluidic systems may result in the presence of a single cell present in a nanodroplet.

Binning may be preceded by positive selection for target cells including, but not limited to affinity binding (e.g. using anti-CD71 antibodies). Alternately, negative selection of non-target cells may precede binning. For example, output from the size-based separation module may be passed through a magnetic hemoglobin enrichment module (MHEM) which selectively removes WBCs from the enriched sample.

For example, the possible cellular content of output from enriched maternal blood which has been passed through a size-based separation module (with or without further enrichment by passing the enriched sample through a MHEM) may consist of: 1) approximately 20 fnRBC; 2) 1,500 mnRBC; 3) 4,000-40,000 WBC; 4) $15 \times 10^6$ RBC. If this sample is separated into 100 bins (PCR wells or other acceptable binning platform), each bin would be expected to contain: 1) 80 negative bins and 20 bins positive for one fnRBC; 2) 150 nmRBC; 3) 400-4,000 WBC; 4) $15 \times 10^4$ RBC. If separated into 10,000 bins, each bin would be expected to contain: 1) 9,980 negative bins and 20 bins positive for one fnRBC; 2) 8,500 negative bins and 1,500 bins positive for one mnRBC; 3)<1-4 WBC; 4) $15 \times 10^2$ RBC. One of skill in the art will recognize that the number of bins may be increased depending on experimental design and/or the platform used for binning. The reduced complexity of the binned cell populations may facilitate further genetic and cellular analysis of the target cells.

Analysis may be performed on individual bins to confirm the presence of target cells (e.g. fnRBC) in the individual bin. Such analysis may consist of any method known in the art, including, but not limited to, FISH, PCR, STR detection, SNP analysis, biomarker detection, and sequence analysis (FIGS. 31 and 32).

IV. Fetal Biomarkers

In some embodiments fetal biomarkers may be used to detect and/or isolate fetal cells, after enrichment or after detection of fetal abnormality or lack thereof. For example, this may be performed by distinguishing between fetal and maternal nRBCs based on relative expression of a gene (e.g., DYSI, DYZ, CD-71, ε- and ζ-globin) that is differentially expressed during fetal development. In preferred embodiments, biomarker genes are differentially expressed in the first and/or second trimester. "Differentially expressed," as applied to nucleotide sequences or polypeptide sequences in a cell or cell nuclei, refers to differences in over/under-expression of that sequence when compared to the level of expression of the same sequence in another sample, a control or a reference sample. In some embodiments, expression differences can be temporal and/or cell-specific. For example, for cell-specific expression of biomarkers, differential expression of one or more biomarkers in the cell(s) of interest can be higher or lower relative to background cell populations. Detection of such difference in expression of the biomarker may indicate the presence of a rare cell (e.g., fnRBC) versus other cells in a mixed sample (e.g., background cell populations). In other embodiments, a ratio of two or more such biomarkers that are differentially expressed can be measured and used to detect rare cells.

In one embodiment, fetal biomarkers comprise differentially expressed hemoglobins. Erythroblasts (nRBCs) are very abundant in the early fetal circulation, virtually absent in normal adult blood and by having a short finite lifespan, there is no risk of obtaining fnRBC which may persist from a previous pregnancy. Furthermore, unlike trophoblast cells, fetal erythroblasts are not prone to mosaic characteristics.

Yolk sac erythroblasts synthesize ε-, ζ-, γ- and α-globins, these combine to form the embryonic hemoglobins. Between six and eight weeks, the primary site of erythropoiesis shifts from the yolk sac to the liver, the three embryonic hemoglobins are replaced by fetal hemoglobin (HbF) as the predominant oxygen transport system, and ε- and ζ-globin production gives way to γ-, α- and β-globin production within definitive erythrocytes (Peschle et al., 1985). HbF remains the principal hemoglobin until birth, when the second globin switch occurs and β-globin production accelerates.

Hemoglobin (Hb) is a heterodimer composed of two identical a globin chains and two copies of a second globin. Due to differential gene expression during fetal development, the composition of the second chain changes from e globin during early embryonic development (1 to 4 weeks of gestation) to γ globin during fetal development (6 to 8 weeks of gestation) to β globin in neonates and adults as illustrated in (Table 1).

TABLE 1

Relative expression of ε, γ and β in maternal and fetal RBCs.

|  |  | ε | γ | B |
|---|---|---|---|---|
| 1st trimester | Fetal | ++ | ++ | − |
|  | Maternal | − | +/− | ++ |
| 2nd trimester | Fetal | − | ++ | +/− |
|  | Maternal | − | +/− | ++ |

In the late-first trimester, the earliest time that fetal cells may be sampled by CVS, fnRBCs contain, in addition to α globin, primarily ε and γ globin. In the early to mid second trimester, when amniocentesis is typically performed, fnRBCs contain primarily γ globin with some adult β globin. Maternal cells contain almost exclusively α and β globin, with traces of γ detectable in some samples. Therefore, by measuring the relative expression of the ε, γ and β genes in RBCs purified from maternal blood samples, the presence of fetal cells in the sample can be determined. Furthermore, positive controls can be utilized to assess failure of the FISH analysis itself.

In various embodiments, fetal cells are distinguished from maternal cells based on the differential expression of hemoglobins β, γ or ε. Expression levels or RNA levels can be determined in the cytoplasm or in the nucleus of cells. Thus in some embodiments, the methods herein involve determining levels of messenger RNA (mRNA), ribosomal RNA (rRNA), or nuclear RNA (nRNA).

In some embodiments, identification of fnRBCs can be achieved by measuring the levels of at least two hemoglobins in the cytoplasm or nucleus of a cell. In various embodiments, identification and assay is from 1, 2, 3, 4, 5, 6, 7, 8, 9, 10, 15 or 20 fetal nuclei. Furthermore, total nuclei arrayed on one or more slides can number from about 100, 200, 300, 400, 500, 700, 800, 5000, 10,000, 100,000, 1,000,000, 2,000,000 to about 3,000,000. In some embodiments, a ratio for γ/β or ε/β is used to determine the presence of fetal cells, where a number less than one indicates that a fnRBC(s) is not present. In some embodiments, the relative expression of γ/β or ε/β provides a fnRBC index ("FNI"), as measured by γ or ε relative to β. In some embodiments, a FNI for γ/β greater than 5, 10, 15, 20, 25, 30, 35, 40, 45, 90, 180, 360, 720, 975, 1020, 1024, 1250 to about 1250, indicate that a fnRBC(s) is present. In yet other embodiments, a FNI for γ/β of less than about 1 indicates that a fnRBC(s) is not present. Preferably, the above FNI is determined from a sample obtained during a first trimester. However, similar ratios can be used during second trimester and third trimester.

In some embodiments, the expression levels are determined by measuring nuclear RNA transcripts including, nascent or unprocessed transcripts. In another embodiment, expression levels are determined by measuring mRNA, including ribosomal RNA. There are many methods known in the art for imaging (e.g., measuring) nucleic acids or RNA including, but not limited to, using expression arrays from Affymetrix, Inc. or Illumina, Inc.

RT-PCR primers can be designed by targeting the globin variable regions, selecting the amplicon size, and adjusting the primers annealing temperature to achieve equal PCR amplification efficiency. Thus TaqMan probes can be designed for each of the amplicons with well-separated fluorescent dyes, Alexa Fluor®-355 for ε, Alexa Fluor®-488 for γ, and Alexa Fluor-555 for β. The specificity of these primers can be first verified using ε, γ, and β cDNA as templates. The primer sets that give the best specificity can be selected for further assay development. As an alternative, the primers can be selected from two exons spanning an intron sequence to amplify only the mRNA to eliminate the genomic DNA contamination.

The primers selected can be tested first in a duplex format to verify their specificity, limit of detection, and amplification efficiency using target cDNA templates. The best combinations of primers can be further tested in a triplex format for its amplification efficiency, detection dynamic range, and limit of detection.

Various commercially available reagents are available for RT-PCR, such as One-step RT-PCR reagents, including Qiagen One-Step RT-PCR Kit and Applied Biosytems TaqMan One-Step RT-PCR Master Mix Reagents kit. Such reagents can be used to establish the expression ratio of ε, γ, and β using purified RNA from enriched samples. Forward primers can be labeled for each of the targets, using Alexa fluor-355 for ε, Alexa fluor-488 for γ, and Alexa fluor-555 for β. Enriched cells can be deposited by cytospinning onto glass slides. Additionally, cytospinning the enriched cells can be performed after in situ RT-PCR. Thereafter, the presence of the fluorescent-labeled amplicons can be visualized by fluorescence microscopy. The reverse transcription time and PCR cycles can be optimized to maximize the amplicon signal:background ratio to have maximal separation of fetal over maternal signature. Preferably, signal:background ratio is greater than 5, 10, 50 or 100 and the overall cell loss during the process is less than 50, 10 or 5%.

V. Fetal Cell Analysis

Fetal conditions that can be determined based on the methods and systems herein include the presence of a fetus and/or a condition of the fetus such as fetal aneuploidy e.g., trisomy 13, trisomy 18, trisomy 21 (Down Syndrome), Klinefelter Syndrome (XXY) and other irregular number of sex or autosomal chromosomes, including monosomy of one or more chromosomes (X chromosome monosomy, also known as Turner's syndrome), trisomy of one or more chromosomes (13, 18, 21, and X), tetrasomy and pentasomy of one or more chromosomes (which in humans is most commonly observed in the sex chromosomes, e.g. XXXX, XXYY, XXXY, XYYY, XXXXX, XXXXY, XXXYY, XYYYY and XXYYY), monoploidy, triploidy (three of every chromosome, e.g. 69 chromosomes in humans), tetraploidy (four of every chromosome, e.g. 92 chromosomes in humans), pentaploidy and multiploidy. Other fetal conditions that can be detected using the methods herein include segmental aneuploidy, such as 1p36 duplication, dup(17)(p11.2p11.2) syndrome, Down syndrome, Pre-eclampsia, Pre-term labor, Edometriosis, Pelizaeus-Merzbacher disease, dup(22)(q11.2q11.2) syndrome, Cat eye syndrome. In some embodiment, the fetal abnormality to be detected is due to one or more deletions in sex or autosomal chromosomes, including Cri-du-chat syndrome, Wolf-Hirschhorn syndrome, Williams-Beuren syndrome, Charcot-Marie-Tooth disease, Hereditary neuropathy with liability to pressure palsies, Smith-Magenis syndrome, Neurofibromatosis, Alagille syndrome, Velocardiofacial syndrome, DiGeorge syndrome, steroid sulfatase deficiency, Kallmann syndrome, Microphthalmia with linear skin defects, Adrenal hypoplasia, Glycerol kinase deficiency, Pelizaeus-Merzbacher disease, testis-determining factor on Y, Azospermia (factor a), Azospermia (factor b), Azospermia (factor c) and 1p36 deletion. In some cases, the fetal abnormality is an abnormal decrease in chromosomal number, such as XO syndrome.

Conditions in a patient that can be detected using the systems and methods herein include, infection (e.g., bacterial, viral, or fungal infection), neoplastic or cancer conditions (e.g., acute lymphoblastic leukemia, acute or chronic lymphocyctic or granulocytic tumor, acute myeloid leukemia, acute promyelocytic leukemia, adenocarcinoma, adenoma, adrenal cancer, basal cell carcinoma, bone cancer, brain cancer, breast cancer, bronchi cancer, cervical dysplasia, chronic myelogenous leukemia, colon cancer, epidermoid carcinoma, Ewing's sarcoma, gallbladder cancer, gallstone tumor, giant cell tumor, glioblastoma multiforma, hairy-cell tumor, head cancer, hyperplasia, hyperplastic comeal nerve tumor, in situ carcinoma, intestinal ganglioneuroma, islet cell tumor, Kaposi's sarcoma, kidney cancer, larynx cancer, leiomyomater tumor, liver cancer, lung cancer, lymphomas, malignant carcinoid, malignant hypercalcemia, malignant melanomas, marfanoid habitus tumor, medullary carcinoma, metastatic skin carcinoma, mucosa) neuromas, mycosis fungoide, myelodysplastic syndrome, myeloma, neck cancer, neural tissue cancer, neuroblastoma, osteogenic sarcoma, osteosarcoma, ovarian tumor, pancreas cancer, parathyroid cancer, pheochromocytoma, polycythemia vera, primary brain tumor, prostate cancer, rectum cancer, renal cell tumor, retinoblastoma, rhabdomyosarcoma, seminoma, skin cancer, small-cell lung tumor, soft tissue sarcoma, squamous cell carcinoma, stomach cancer, thyroid cancer, topical skin lesion, veticulum cell sarcoma, or Wilm's tumor), inflammation, etc.

In some cases, sample analyses involves performing one or more genetic analyses or detection steps on nucleic acids from the enriched product (e.g., enriched cells or nuclei). Nucleic acids from enriched cells or enriched nuclei that can be analyzed by the methods herein include: double-stranded DNA, single-stranded DNA, single-stranded DNA hairpins, DNA/RNA hybrids, RNA (e.g. mRNA) and RNA hairpins. Examples of genetic analyses that can be performed on enriched cells or nucleic acids include, e.g., SNP detection, STR detection, and RNA expression analysis.

In some embodiments, less than 1 µg, 500 ng, 200 ng, 100 ng, 50 ng, 40 n 30 ng, 20 ng, 10 ng, 5 ng, 1 ng, 500 pg 200 pg 100 pg 50 pg, 40 pg, 30 pg, 20 pg, 10 pg, 5 pg, or 1 pg of nucleic acids are obtained from the enriched sample for further genetic analysis. In some cases, about 1-5 µg, 5-10 pg, or 10-100 µg of nucleic acids are obtained from the enriched sample for further genetic analysis.

When analyzing, for example, a sample such as a blood sample from a patient to diagnose a condition such as cancer, the genetic analyses can be performed on one or more genes encoding or regulating a polypeptide listed in FIG. 5. In some cases, a diagnosis is made by comparing results from such genetic analyses with results from similar analyses from a reference sample (one without fetal cells or CTC's, as the case may be). For example, a maternal blood sample enriched for fetal cells can be analyzed to determine the presence of fetal cells and/or a condition in such cells by comparing the ratio of maternal to paternal genomic DNA (or alleles) in control and test samples.

In some embodiments, target nucleic acids from a test sample are amplified and optionally results are compared with amplification of similar target nucleic acids from a non-rare cell population (reference sample). Amplification of target nucleic acids can be performed by any means known in the art. In some cases, target nucleic acids are amplified by polymerase chain reaction (PCR). Examples of PCR techniques that can be used include, but are not limited to, quantitative PCR, quantitative fluorescent PCR (QF-PCR), multiplex fluorescent PCR (MF-PCR), real time PCR (RT-PCR), single cell PCR, restriction fragment length polymorphism PCR (PCR-RFLP), PCR-RFLP/RT-PCR-RFLP, hot start PCR, nested PCR, in situ polonony PCR, in situ rolling circle amplification (RCA), bridge PCR, picotiter PCR and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that can be used herein include those described in U.S. Pat. Nos. 5,242,794; 5,494,810; 4,988, 617; and 6,582,938.

In any of the embodiments, amplification of target nucleic acids may occur on a bead. In any of the embodiments herein, target nucleic acids may be obtained from a single cell.

In any of the embodiments herein, the nucleic acid(s) of interest can be pre-amplified prior to the amplification step (e.g., PCR). In some cases, a nucleic acid sample may be pre-amplified to increase the overall abundance of genetic material to be analyzed (e.g., DNA). Pre-amplification can therefore include whole genome amplification such as multiple displacement amplification (MDA) or amplifications with outer primers in a nested PCR approach.

In some embodiments amplified nucleic acid(s) are quantified. Methods for quantifying nucleic acids are known in the art and include, but are not limited to, gas chromatography, supercritical fluid chromatography, liquid chromatography (including partition chromatography, adsorption chromatography, ion exchange chromatography, size-exclusion chromatography, thin-layer chromatography, and affinity chromatography), electrophoresis (including capillary electrophoresis, capillary zone electrophoresis, capillary isoelectric focusing, capillary electrochromatography, micellar electrokinetic capillary chromatography, isotachophoresis, transient isotachophoresis and capillary gel electrophoresis), comparative genomic hybridization (CGH), microarrays, bead arrays, and high-throughput genotyping such as with the use of molecular inversion probe (MIP).

Quantification of amplified target nucleic acid can be used to determine gene/or allele copy number, gene or exon-level expression; methylation-state analysis, or detect a novel transcript in order to diagnose or condition, i.e. fetal abnormality or cancer.

In some embodiments, analysis involves detecting one or more mutations or SNPs in DNA from e.g., enriched rare cells or enriched rare DNA. Such detection can be performed using, for example, DNA microarrays. Examples of DNA microarrays include those commercially available from Afilymetrix, Inc. (Santa Clara, Calif.), including the GeneChip™ Mapping Arrays including Mapping 100K Set, Mapping 10K 2.0 Array, Mapping 10K Array, Mapping 500K Array Set, and GeneChip™ Human Mitochondrial Resequencing Array 2.0. The Mapping 10K array, Mapping 100K array set, and Mapping 500K array set analyze more than 10,000, 100,000 and 500,000 different human SNPs, respectively. SNP detection and analysis using GeneChip™ Mapping Arrays is described in part in Kennedy, G. C., et al., Nature Biotechnology 21, 1233-1237, 2003; Liu, W. M., Bioinformatics 19, 2397-2403, 2003; Matsuzaki, H., Genome Research 3, 414-25, 2004; and Matsuzaki, H., Nature Methods, 1, 109-111, 2004 as well as in U.S. Pat. Nos. 5,445,934; 5,744,305; 6,261,776; 6,291,183; 5,799, 637; 5,945,334; 6,346,413; 6,399,365; and 6,610,482, and EP 619 321; 373 203. In some embodiments, a microarray is used to detect at least 5, 10, 20, 50, 100, 200, 500, 1,000, 2,000, 5,000 10,000, 20,000, 50,000, 100,000, 200,000, or 500,000 different nucleic acid target(s) (e.g., SNPs, mutations or STRs) in a sample.

Methods for analyzing chromosomal copy number using mapping arrays are disclosed, for example, in Bignell et al., Genome Res. 14:287-95 (2004), Lieberfarb, et al., Cancer Res. 63:4781-4785 (2003), Zhao et al., Cancer Res. 64:3060-71 (2004), Nannya et al., Cancer Res. 65:6071-6079 (2005) and Ishikawa et al., Biochem. and Biophys. Res. Comm., 333:1309-1314 (2005). Computer implemented methods for estimation of copy number based on hybridization intensity are disclosed in U.S. Publication Application Nos. 20040157243; 20050064476; and 20050130217.

In preferred aspects, mapping analysis using fixed content arrays, for example, 10K, 100K or 500K arrays, preferably identify one or a few regions that show linkage or association with the phenotype of interest. Those linked regions may then be more closely analyzed to identify and genotype polymorphisms within the identified region or regions, for example, by designing a panel of MIPs targeting polymorphisms or mutations in the identified region. The targeted regions may be amplified by hybridization of a target specific primer and extension of the primer by a highly processive strand displacing polymerase, such as phi29 and then analyzed, for example, by genotyping.

Figure 6:
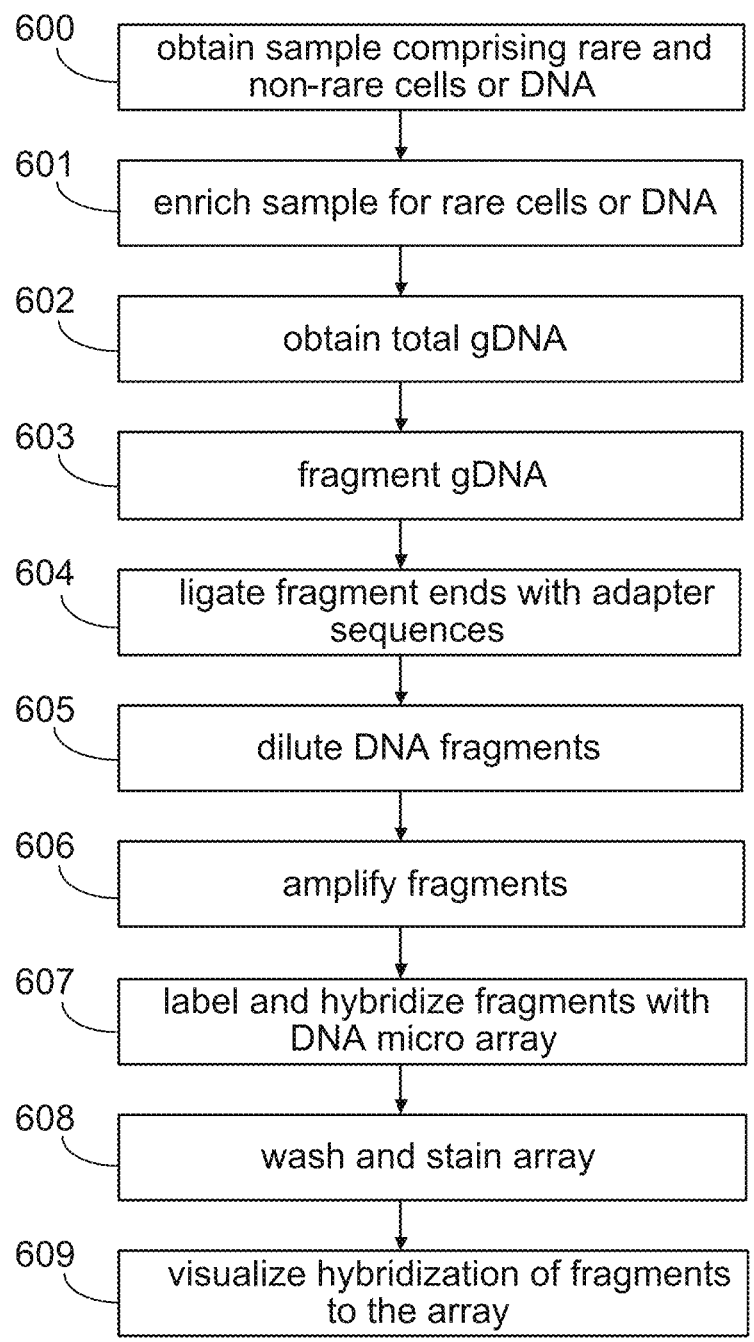
FIG. 6 illustrates one embodiment for genotyping rare cell(s) or rare DNA using, e.g., Affymetrix DNA microarrays.

A quick overview for the process of using a SNP detection microarray (such as the Mapping 100K Set) is illustrated in FIG. 6. First, in step 600 a sample comprising one or more rare cells (e.g., fetal or CTC) and non-rare cells (e.g., RBC's) is obtained from an animal such as a human. In step 601, rare cells or rare DNA (e.g., rare nuclei) are enriched using one or more methods disclosed herein or known in the art. Preferably, rare cells are enriched by flowing the sample through an array of obstacles that selectively directs particles or cells of different hydrodynamic sizes into different outlets. In some cases, gDNA is obtained from both rare and non-rare cells enriched by the methods herein.

In step 602, genomic DNA is obtained from the rare cell(s) or nuclei and optionally one or more non-rare cells remaining in the enriched mixture. In step 603, the genomic DNA obtained from the enriched sample is digested with a restriction enzyme, such as XbaI or Hind III. Other DNA microarrays may be designed for use with other restriction enzymes, e.g., Sty I or NspI. In step 604 all fragments resulting from the digestion are ligated on both ends with an adapter sequence that recognizes the overhangs from the restriction digest. In step 605, the DNA fragments are diluted. Subsequently, in step 606 fragments having the adapter sequence at both ends are amplified using a generic primer that recognizes the adapter sequence. The PCR conditions used for amplification preferentially amplify fragments that have a unique length, e.g., between 250 and 2,000 base pairs in length. In steps 607, amplified DNA sequences are fragmented, labeled and hybridized with the DNA microarray (e.g., 100K Set Array or other array). Hybridization is followed by a step 608 of washing and staining.

In step 609 results are visualized using a scanner that enables the viewing of intensity of data collected and a software "calls" the bases present at each of the SNP positions analyzed. Computer implemented methods for determining genotype using data from mapping arrays are disclosed, for example, in Liu, et al., Bioinformatics 19:2397-2403, 2003; and Di et al., Bioinformatics 21:1958-63, 2005. Computer implemented methods for linkage analysis using mapping array data are disclosed, for example, in Ruschendorf and Nurnberg, Bioinformatics 21:2123-5, 2005; and Leykin et al., BMC Genet. 6:7, 2005; and in U.S. Pat. No. 5,733,729.

In some cases, genotyping microarrays that are used to detect SNPs can be used in combination with molecular inversion probes (MIPs) as described in Hardenbol et al., Genome Res. 15(2):269-275, 2005, Hardenbol, P. et al. Nature Biotechnology 21(6), 673-8, 2003; Faham M, et al. Hum Mol Genet. August 1; 10(16):1657-64,2001; Maneesh Jain, Ph.D., et all. Genetic Engineering News V24: No. 18, 2004; and Fakhrai-Rad H, et al. Genome Res. July; 14(7): 1404-12, 2004; and in U.S. Pat. No. 6,858,412. Universal tag arrays and reagent kits for performing such locus specific genotyping using panels of custom MIPs are available from Affymetrix and ParAllele. MIP technology involves the use enzymological reactions that can score up to 10,000; 20,000, 50,000; 100,000; 200,000; 500,000; 1,000,000; 2,000,000 or 5,000,000 SNPs (target nucleic acids) in a single assay. The enzymological reactions are insensitive to cross-reactivity among multiple probe molecules and there is no need for pre-amplification prior to hybridization of the probe with the genomic DNA. In any of the embodiments, the target nucleic acid(s) or SNPs are obtained from a single cell.

Thus, the present invention contemplates obtaining a sample enriched for fetal cells, epithelial cells or CTC's and analyzing such enriched sample using the MIP technology or oligonucleotide probes that are precircle probes i.e., probes that form a substantially complete circle when they hybridize to a SNP. The precircle probes comprise a first targeting domain that hybridizes upstream to a SNP position, a second targeting domain that hybridizes downstream of a SNP position, at least a first universal priming site, and a cleavage site. Once the probes are allowed to contact genomic DNA regions of interest (comprising SNPs to be assayed), a hybridization complex forms with a precircle probe and a gap at a SNP position region. Subsequently, ligase is used to "fill in" the gap or complete the circle. The enzymatic "gap fill" process occurs in an allele-specific manner. The nucleotide added to the probe to fill the gap is complementary to the nucleotide base at the SNP position. Once the probe is circular, it may be separated from cross-reacted or unreacted probes by a simple exonuclease reaction. The circular probe is then cleaved at the cleavage site such that it becomes linear again. The cleavage site can be any site in the probe other than the SNP site. Linearization of the circular probe results in the placement of universal primer region at one end of the probe. The universal primer region can be coupled to a tag region. The tag can be detected using amplification techniques known in the art. The SNP analyzed can subsequently be detected by amplifying the cleaved (linearized) probe to detect the presence of the target sequence in said sample or the presence of the tag.

Another method contemplated by the present invention to detect SNPs involves the use of bead arrays (e.g., such as one commercially available by Illumina, Inc.) as described in U.S. Pat. Nos. 7,040,959; 7,035,740; 7,033,754; 7,025,935; 6,998,274; 6,942,968; 6,913,884; 6,890,764; 6,890,741; 6,858,394; 6,846,460; 6,812,005; 6,770,441; 6,663,832; 6,620,584; 6,544,732; 6,429,027; 6,396,995; 6,355,431 and US Publication Application Nos. 20060019258; 20050266432; 20050244870; 20050216207; 20050181394; 20050164246; 20040224353; 20040185482; 20030198573; 20030175773; 20030003490; 20020187515; and 20020177141; as well as Shen, R., et al. Mutation Research 573 70-82 (2005).

Figure 7:
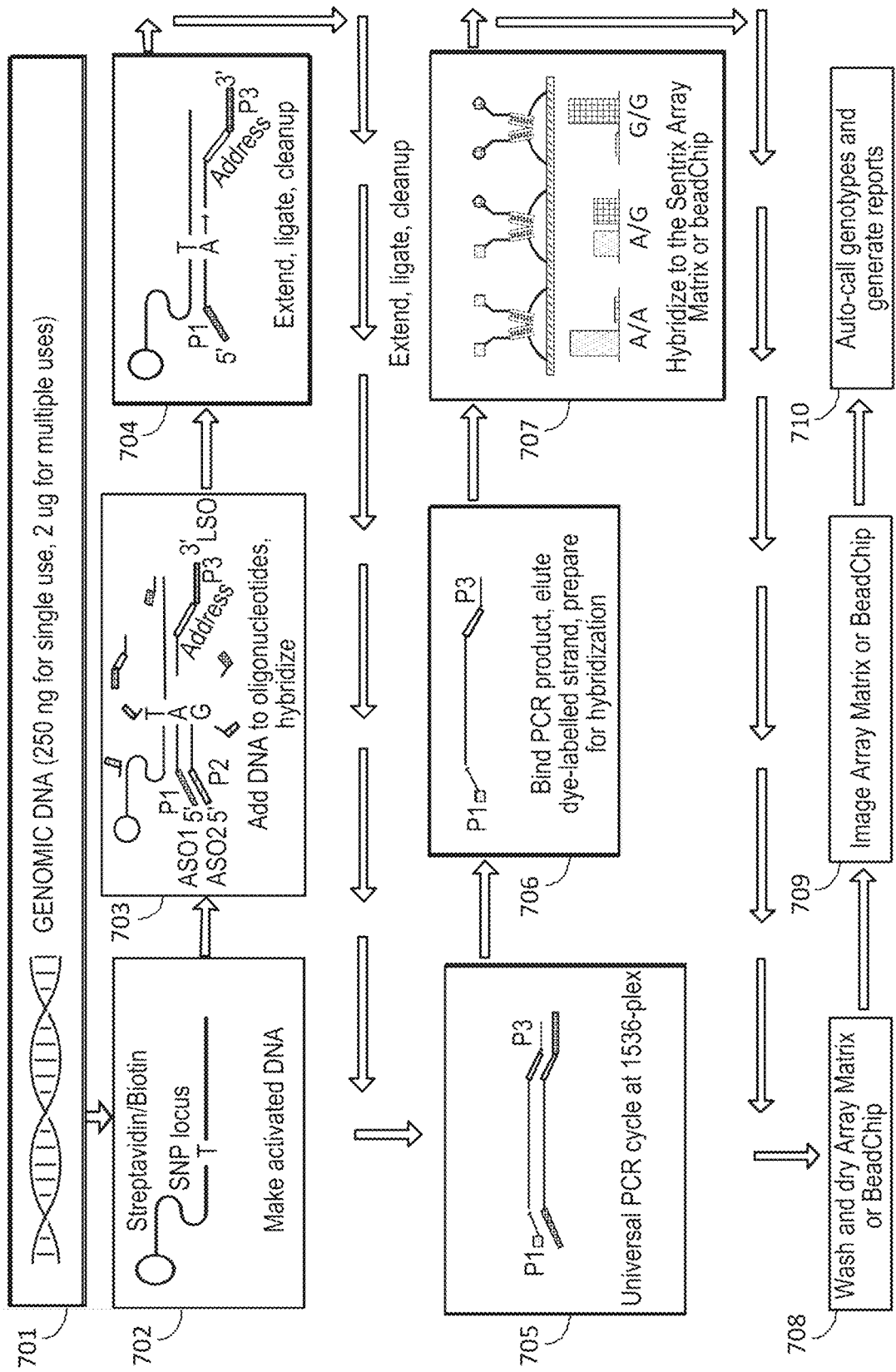
FIG. 7 illustrates one embodiment for genotyping rare cell(s) or rare DNA using, e.g., Illumina bead arrays.

FIG. 7 illustrates an overview of one embodiment of detecting mutations or SNPs using bead arrays. In this embodiment, a sample comprising one or more rare cells (e.g., fetal or CTC) and non-rare cells (e.g., RBC's) is obtained from an animal such as a human. Rare cells or rare DNA (e.g., rare nuclei) are enriched using one or more methods disclosed herein or known in the art. Preferably, rare cells are enriched by flowing the sample through an array of obstacles that selectively directs particles or cells of different hydrodynamic sizes into different outlets.

In step 701, genomic DNA is obtained from the rare cell(s) or nuclei and, optionally, from the one or more non-rare cells remaining in the enriched mixture. The assays in this embodiment require very little genomic DNA starting material, e.g., between 250 ng-2 µg. Depending on the multiplex level, the activation step may require only 160 pg of DNA per SNP genotype call. In step 702, the genomic DNA is activated such that it may bind paramagnetic particles. In step 703 assay oligonucleotides, hybridization buffer, and paramagnetic particles are combined with the activated DNA and allowed to hybridize (hybridization step). In some cases, three oligonucleotides are added for each SNP to be detected. Two of the three oligos are specific for each of the two alleles at a SNP position and are referred to as Allele-Specific Oligos (ASOs). A third oligo hybridizes several bases downstream from the SNP site and is referred to as the Locus-Specific Oligo (LSO). All three oligos contain regions of genomic complementarity (C1, C2, and C3) and universal PCR primer sites (P1, P2 and P3). The LSO also contains a unique address sequence (Address) that targets a particular bead type. (Up to 1,536 SNPs may be assayed in this manner using GoldenGate™ Assay available by Illumina, Inc. (San Diego, Calif.).) During the primer hybridization process, the assay oligonucleotides hybridize to the genomic DNA sample bound to paramagnetic particles. Because hybridization occurs prior to any amplification steps, no amplification bias is introduced into the assay.

In step 704, following the hybridization step, several wash steps are performed reducing noise by removing excess and mis-hybridized oligonucleotides. Extension of the appropriate ASO and ligation of the extended product to the LSO joins information about the genotype present at the SNP site to the address sequence on the LSO. In step 705, the joined, full-length products provide a template for performing PCR reactions using universal PCR primers P1, P2, and P3. Universal primers P1 and P2 are labeled with two different labels (e.g., Cy3 and Cy5). Other labels that can be used include, chromophores, fluorescent moieties, enzymes, antigens, heavy metal, magnetic probes, dyes, phosphorescent groups, radioactive materials, chemiluminescent moieties, scattering or fluorescent nanoparticles, Raman signal generating moieties, or electrochemical detection moieties.

In step 706, the single-stranded, labeled DNAs are eluted and prepared for hybridization. In step 707, the single-stranded, labeled DNAs are hybridized to their complement bead type through their unique address sequence. Hybridization of the GoldenGate Assay™ products onto the Array Matrix™ of Beadchip™ allows for separation of the assay products in solution, onto a solid surface for individual SNP genotype readout.

In step 708, the array is washed and dried. In step 709, a reader such as the BeadArray Reader™ is used to analyze signals from the label. For example, when the labels are dye labels such as Cy3 and Cy5, the reader can analyze the fluorescence signal on the Sentrix Array Matrix or Bead-Chip.

In step 710, a computer program comprising a computer readable medium having a computer executable logic is used to automate genotyping clusters and callings.

In any of the embodiments herein, preferably, more than 1000, 5,000, 10,000, 50,000, 100,000, 500,000, or 1,000,000 SNPs are assayed in parallel.

In some embodiments, analysis involves detecting levels of expression of one or more genes or exons in e.g., enriched rare cells or enriched rare mRNA. Such detection can be performed using, for example, expression microarrays. Thus, the present invention contemplates a method comprising the steps of: enriching rare cells from a sample as described herein, isolating nucleic acids from the rare cells, contacting a microarray under conditions such that the nucleic acids specifically hybridize to the genetic probes on the microarray, and determining the binding specificity (and amount of binding) of the nucleic acid from the enriched sample to the probes. The results from these steps can be used to obtain a binding pattern that would reflect the nucleic acid abundance and establish a gene expression profile. In some embodiments, the gene expression or copy number results from the enriched cell population is compared with gene expression or copy number of a non-rare cell population to diagnose a disease or a condition.

Examples of expression microarrays include those commercially available from Affymetrix, Inc. (Santa Clara, Calif.), such as the exon arrays (e.g., Human Exon ST Array); tiling arrays (e.g., Chromosome 21/22 1.0 Array Set, ENCODE01 1.0 Array, or Human Genome Arrays+); and 3' eukaryotic gene expression arrays (e.g., Human Genome Array+, etc.). Examples of human genome arrays include HuGene FL Genome Array, Human Cancer GI 10 ARray, Human Exon 1.0 ST, Human Genome Focus Array, Human Genome U133 Plus 2.0, Human Genome U133 Set, Human Genome U133A 2.0, Human Promoter U95 SetX, Human Tiling 1.0R Array Set, Human Tiling 2.0R Array Set, and Human X3P Array.

Expression detection and analysis using microarrays is described in part in Valk, P. J. et al. New England Journal of Medicine 350(16), 1617-28, 2004; Modlich, O. et al. Clinical Cancer Research 10(10), 3410-21, 2004; Onken, Michael D. et al. Cancer Res. 64(20), 7205-7209, 2004; Gardian, et al. J. Biol. Chem. 280(1), 556-563, 2005; Becker, M. et al. Mol. Cancer Ther. 4(1), 151-170, 2005; and Flechner, S M et al. Am J Transplant 4(9), 1475-89, 2004; as well as in U.S. Pat. Nos. 5,445,934; 5,700,637; 5,744,305; 5,945,334; 6,054,270; 6,140,044; 6,261,776; 6,291,183; 6,346,413; 6,399,365; 6,420,169; 6,551,817; 6,610,482; 6,733,977; and EP 619 321; 323 203.

Figure 8:
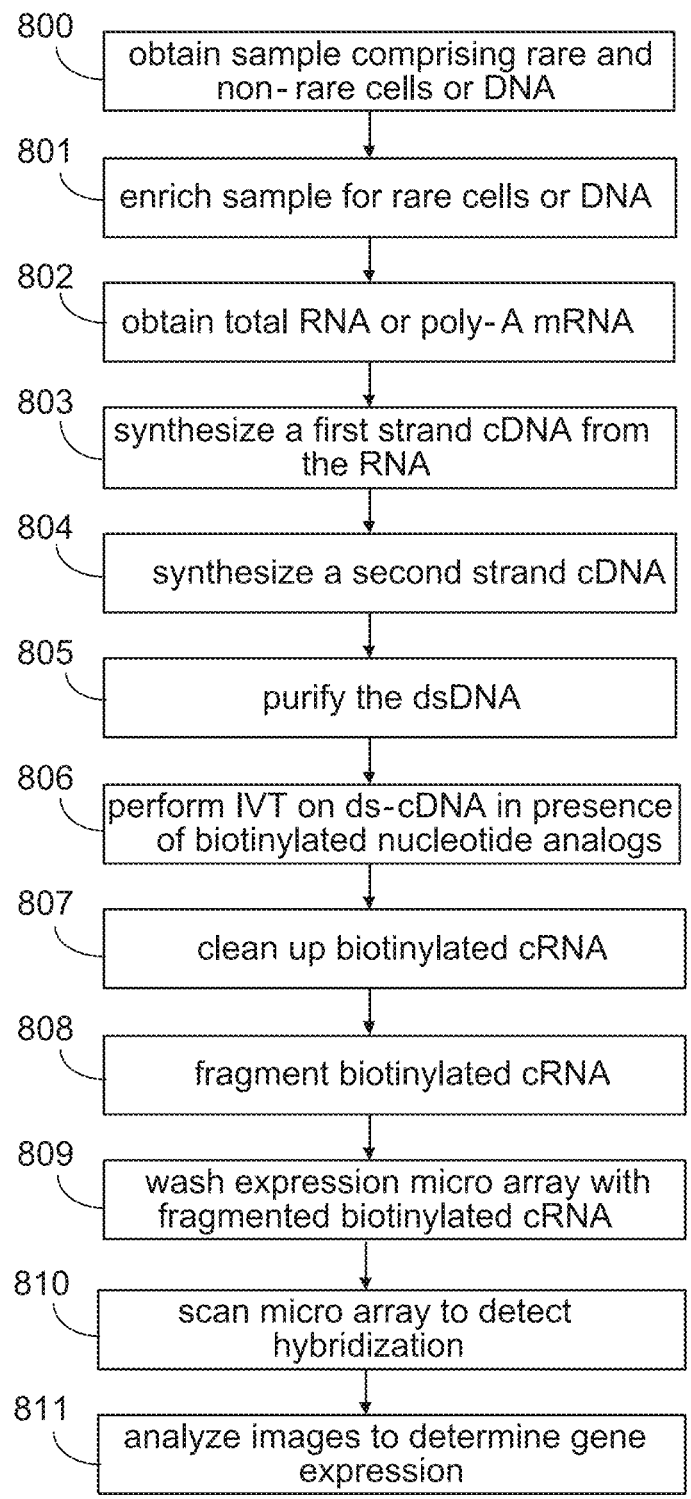
FIG. 8 illustrates one embodiment for determining gene expression of rare cell(s) or rare DNA using, e.g., Affymetrix expression chips.

An overview of a protocol that can be used to detect RNA expression (e.g., using Human Genome U133A Set) is illustrated in FIG. 8. In step 800 a sample comprising one or more rare cells (e.g., fetal, epithelial or CTC) and non-rare cells (e.g., RBC's) is obtained from an animal, such as a human. In step 801, rare cells or rare DNA (e.g., rare nuclei) are enriched using one or more methods disclosed herein or known in the art. Preferably, rare cells are enriched by flowing the sample through an array of obstacles that selectively directs particles or cells of different hydrodynamic sizes into different outlets such that rare cells and cells larger than rare cells are directed into a first outlet and one or more cells or particles smaller than the rare cells are directed into a second outlet.

In step 802 total RNA or poly-A mRNA is obtained from enriched cell(s) (e.g., fetal, epithelial or CTC's) using purification techniques known in the art. Generally, about 1 µg-2 µg of total RNA is sufficient. In step 803, a first-strand complementary DNA (cDNA) is synthesized using reverse transcriptase and a single T7-oligo(dT) primer. In step 804, a second-strand cDNA is synthesized using DNA ligase, DNA polymerase, and RNase enzyme. In step 805, the double stranded cDNA (ds-cDNA) is purified. In step 806, the ds-cDNA serves as a template for in vitro transcription reaction. The in vitro transcription reaction is carried out in the presence of T7 RNA polymerase and a biotinylated nucleotide analog/ribonucleotide mix. This generates roughly ten times as many complementary RNA (cRNA) transcripts.

In step 807, biotinylated cRNAs are cleaned up, and subsequently in step 808, they are fragmented randomly. Finally, in step 809 the expression microarray (e.g., Human Genome U133 Set) is washed with the fragmented, biotin-labeled cRNAs and subsequently stained with streptavidin phycoerythrin (SAPE). And in step 810, after final washing, the microarray is scanned to detect hybridization of cRNA to probe pairs.

In step 811 a computer program product comprising a computer executable logic analyzes images generated from the scanner to determine gene expression. Such methods are disclosed in part in U.S. Pat. No. 6,505,125.

Another method contemplated by the present invention to detect and quantify gene expression involves the use of bead as is commercially available by Illumina, Inc. (San Diego) and as described in U.S. Pat. Nos. 7,035,740; 7,033,754; 7,025,935, 6,998,274; 6,942,968; 6,913,884; 6,890,764; 6,890,741; 6,858,394; 6,812,005; 6,770,441; 6,620,584; 6,544,732; 6,429,027; 6,396,995; 6,355,431 and US Publication Application Nos. 20060019258; 20050266432; 20050244870; 20050216207; 20050181394; 20050164246; 20040224353; 20040185482; 20030198573; 20030175773; 20030003490; 20020187515; and 20020177141; and in B. E. Stranger, et al., Public Library of Science-Genetics, 1 (6), December 2005; Jingli Cai, et al., Stem Cells, published online Nov. 17, 2005; C. M. Schwartz, et al., Stem Cells and Development, 14, 517-534, 2005; Barnes, M., J. et al., Nucleic Acids Research, 33 (18), 5914-5923, October 2005; and Bibikova M, et al. Clinical Chemistry, Volume 50, No. 12, 2384-2386, December 2004.

Figure 9:
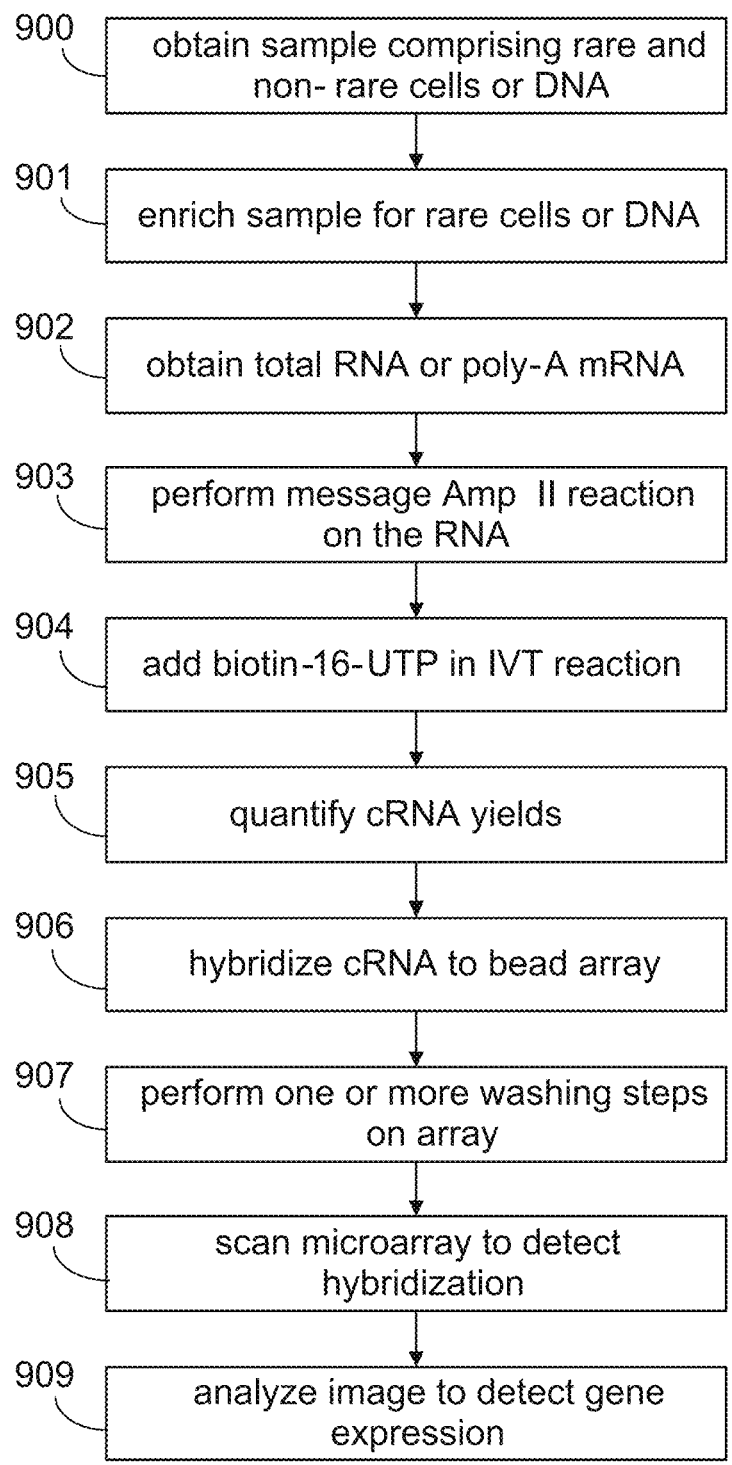
FIG. 9 illustrates one embodiment for determining gene expression of rare cell(s) or rare DNA using, e.g., Illumina bead arrays.

FIG. 9 illustrates an overview of one embodiment of detecting mutations or SNPs using bead arrays. In step 900 a sample comprising one or more rare cells (e.g., fetal, epithelial or CTC) and non-rare cells (e.g., RBC's) is obtained from an animal, such as a human. In step 901, rare cells or rare DNA (e.g., rare nuclei) are enriched using one or more methods disclosed herein or known in the art. Preferably, rare cells are enriched by flowing the sample through an array of obstacles that selectively directs particles or cells of different hydrodynamic sizes into different outlets such that rare cells and cells larger than rare cells are directed into a first outlet and one or more cells or particles smaller than the rare cells are directed into a second outlet.

In step 902, total RNA is extracted from enriched cells (e.g., fetal cells, CTC, or epithelial cells). In step 903, two one-quarter scale Message Amp II reactions (Ambion, Austin, Tex.) are performed for each RNA extraction using 200 ng of total RNA. MessageAmp is a procedure based on antisense RNA (aRNA) amplification, and involves a series of enzymatic reactions resulting in linear amplification of exceedingly small amounts of RNA for use in array analysis. Unlike exponential RNA amplification methods, such as NASBA and RT-PCR, aRNA amplification maintains representation of the starting mRNA population. The procedure begins with total or poly(A) RNA that is reverse transcribed using a primer containing both oligo(dT) and a T7 RNA polymerase promoter sequence. After first-strand synthesis, the reaction is treated with RNase H to cleave the mRNA into small fragments. These small RNA fragments serve as primers during a second-strand synthesis reaction that produces a double-stranded cDNA template for transcription. Contaminating rRNA, mRNA fragments and primers are removed and the cDNA template is then used in a large scale in vitro transcription reaction to produce linearly amplified aRNA. The aRNA can be labeled with biotin rNTPS or amino allyl-UTP during transcription.

In step 904, biotin-16-UTP (Perkin Elmer, Wellesley, Calif.) is added such that half of the UTP is used in the in vitro transcription reaction. In step 905, cRNA yields are quantified using RiboGreen (Invitrogen, Carlsbad, Calif.). In step 906, 1 µg of cRNA is hybridized to a bead array (e.g., Illumina Bead Array). In step 907, one or more washing steps is performed on the array. In step 908, after final washing, the microarray is scanned to detect hybridization of cRNA. In step 908, a computer program product comprising an executable program analyzes images generated from the scanner to determine gene expression.

Additional description for preparing RNA for bead arrays is described in Kacharmina J E, et al., Methods Enzymol 303: 3-18, 1999; Pabon C, et al., Biotechniques 31(4): 874-9, 2001; Van Gelder R N, et al., Proc Natl Acad Sci USA 87: 1663-7 (1990); and Murray, S S. BMC Genetics 6(Suppl I):S85 (2005).

Preferably, more than 1000, 5,000, 10,000, 50,000, 100,000, 500,000, or 1,000,000 transcripts are assayed in parallel In any of the embodiments herein, genotyping (e.g., SNP detection) and/or expression analysis (e.g., RNA transcript quantification) of genetic content from enriched rare cells or enriched rare cell nuclei can be accomplished by sequencing. Sequencing can be accomplished through classic Sanger sequencing methods which are well known in the art. Sequence can also be accomplished using high-throughput systems some of which allow detection of a sequenced nucleotide immediately after or upon its incorporation into a growing strand, i.e., detection of sequence in real time or substantially real time. In some cases, high throughput sequencing generates at least 1,000, at least 5,000, at least 10,000, at least 20,000, at least 30,000, at least 40,000, at least 50,000, at least 100,000 or at least 500,000 sequence reads per hour, with each read being at least 50, at least 60, at least 70, at least 80, at least 90, at least 100, at least 120 or at least 150 bases per read. Sequencing can be preformed using genomic DNA or cDNA derived from RNA transcripts as a template.

In some embodiments, high-throughput sequencing involves the use of technology available by Helicos BioSciences Corporation (Cambridge, Mass.) such as the Single Molecule Sequencing by Synthesis (SMSS) method. SMSS is unique because it allows for sequencing the entire human genome in up to 24 hours. This fast sequencing method also allows for detection of a SNP/nucleotide in a sequence in substantially real time or real time. Finally, SMSS is powerful because, like the MIP technology, it does not require a preamplification step prior to hybridization. In fact, SMSS does not require any amplification. SMSS is described in part in US Publication Application Nos. 20060024711; 20060024678; 20060012793; 20060012784; and 20050100932.

Figure 10:
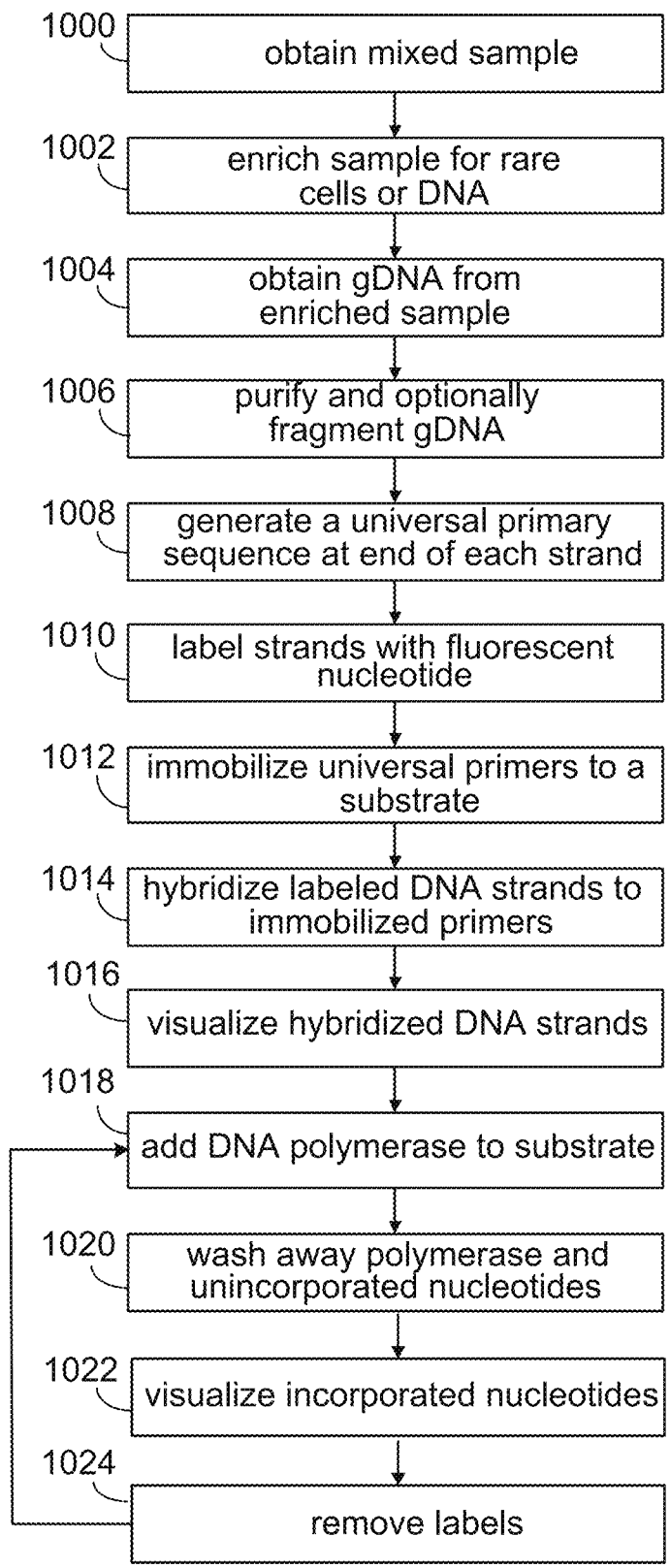
FIG. 10 illustrates one embodiment for high-throughput sequencing of rare cell(s) or rare DNA using, e.g., single molecule sequence by synthesis methods (e.g., Helicos BioSciences Corporation).

An overview the use of SMSS for analysis of enriched cells/nucleic acids (e.g., fetal cells, epithelial cells, CTC's) is outlined in FIG. 10.

First, in step 1000 a sample comprising one or more rare cells (e.g., fetal or CTC) and one or more non-rare cells (e.g., RBC's) is obtained from an animal, such as a human. In step 1002, rare cells or rare DNA (e.g., rare nuclei) are enriched using one or more methods disclosed herein or known in the art. Preferably, rare cells are enriched by flowing the sample through an array of obstacles that selectively directs particles or cells of different hydrodynamic sizes into different outlets. In step 1004, genomic DNA is obtained from the rare cell(s) or nuclei and optionally one or more non-rare cells remaining in the enriched mixture.

In step 1006 the genomic DNA is purified and optionally fragmented. In step 1008, a universal priming sequence is generated at the end of each strand. In step 1010, the strands are labeled with a fluorescent nucleotide. These strands will serve as templates in the sequencing reactions.

In step 1012 universal primers are immobilized on a substrate (e.g., glass surface) inside a flow cell.

In step 1014, the labeled DNA strands are hybridized to the immobilized primers on the substrate.

In step 1016, the hybridized DNA strands are visualized by illuminating the surface of the substrate with a laser and imaging the labeled DNA with a digital TV camera connected to a microscope. In this step, the position of all hybridization duplexes on the surface is recorded.

In step 1018, DNA polymerase is flowed into the flow cell. The polymerase catalyzes the addition of the labeled nucleotides to the correct primers.

In step 1020, the polymerase and unincorporated nucleotides are washed away in one or more washing procedures.

In step 1022, the incorporated nucleotides are visualized by illuminating the surface with a laser and imaging the incorporated nucleotides with a camera. In this step, recordation is made of the positions of the incorporated nucleotides.

In step 1024, the fluorescent labels on each nucleotide are removed.

Steps 1018-1024 are repeated with the next nucleotide such that the steps are repeated for A, G, T, and C. This sequence of events is repeated until the desired read length is achieved.

SMSS can be used, e.g., to sequence DNA from enriched CTC's to identify genetic mutations (e.g., SNPs) in DNA, or to profile gene expression of mRNA transcrips of such cells or other cells (fetal cells). SMSS can also be used to identify genes in CTC's that are methylated ("turned off") and develop cancer diagnostics based on such methylation. Finally, enriched cells/DNA can be analyzed using SMSS to detect minute levels of DNA from pathogens such as viruses, bacteria or fungi. Such DNA analysis can further be used for serotyping to detect, e.g., drug resistance or susceptibility to disease. Furthermore, enriched stem cells can be analyzed using SMSS to determine if various expression profiles and differentiation pathways are turned "on" or "off". This allows for a determination to be made of the enriched stem cells are prior to or post differentiation.

In some embodiments, high-throughput sequencing involves the use of technology available by 454 Lifesciences, Inc. (Branford, Conn.) such as the PicoTiterPlate device which includes a fiber optic plate that transmits chemilluminescent signal generated by the sequencing reaction to be recorded by a CCD camera in the instrument. This use of fiber optics allows for the detection of a minimum of 20 million base pairs in 4.5 hours.

Methods for using bead amplification followed by fiber optics detection are described in Marguiles, M., et al. "Genome sequencing in microfabricated high-density pricolitre reactors", Nature, doi:10.1038/nature03959; and well as Attorney Docket No. 32047-719.201 in US Publication Application Nos. 20020012930; 20030068629; 20030100102; 20030148344; 20040248161; 20050079510, 20050124022; and 20060078909.

Figure 11:
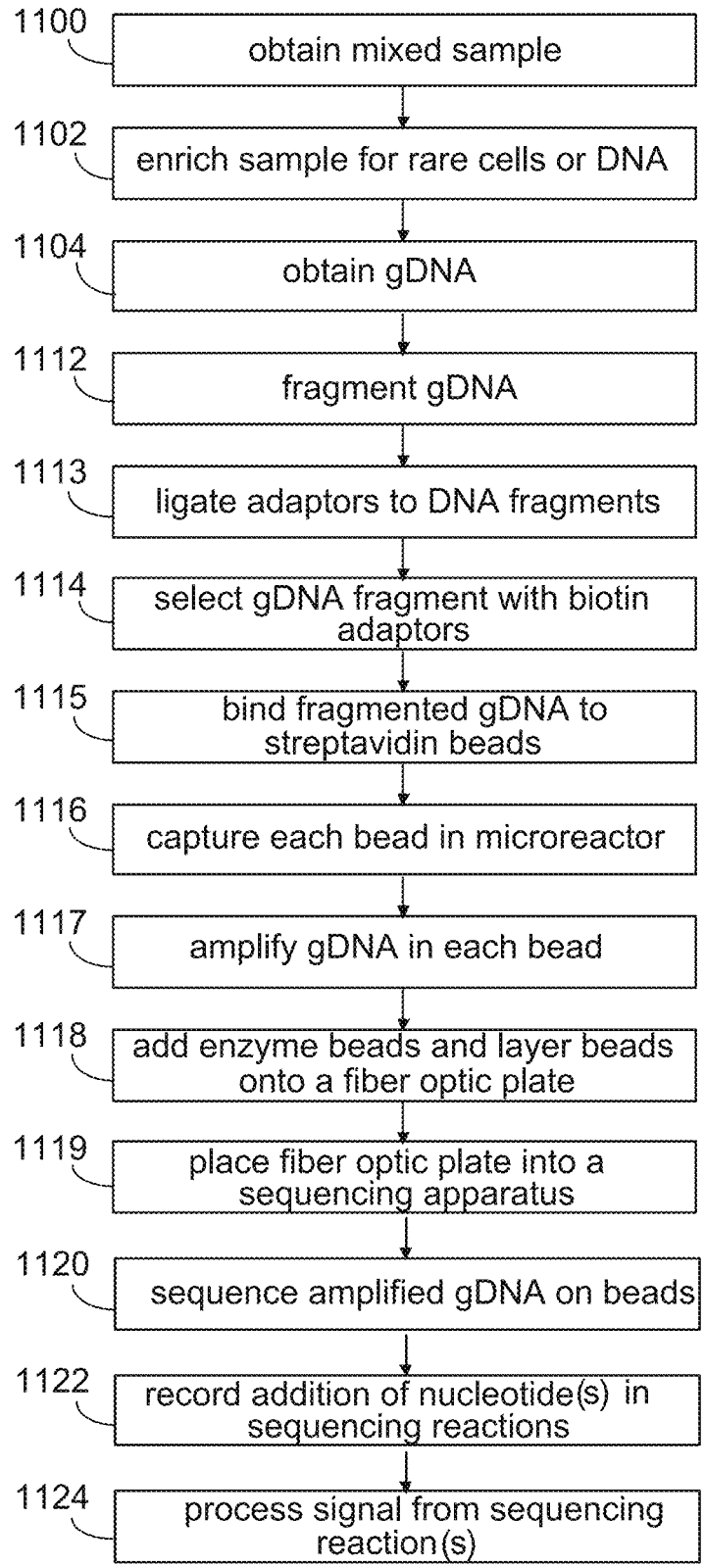
FIG. 11 illustrates one embodiment for high-throughput sequencing of rare cell(s) or rare DNA using, e.g., amplification of nucleic acid molecules on a bead (e.g., 454 Lifesciences).

An overview of this embodiment is illustrated in FIG. 11.

First, in step 1100 a sample comprising one or more rare cells (e.g., fetal, epithelial or CTC) and one or more non-rare cells (e.g., RBC's) is obtained from an animal, such as a human. In step 1102, rare cells or rare DNA (e.g., rare nuclei) are enriched using one or more methods disclosed herein or known in the art. Preferably, rare cells are enriched by flowing the sample through an array of obstacles that selectively directs particles or cells of different hydrodynamic sizes into different outlets. In step 1104, genomic DNA is obtained from the rare cell(s) or nuclei and optionally one or more non-rare cells remaining in the enriched mixture.

In step 1112, the enriched genomic DNA is fragmented to generate a library of hundreds of DNA fragments for sequencing runs. Genomic DNA (gDNA) is fractionated into smaller fragments (300-500 base pairs) that are subsequently polished (blunted). In step 1113, short adaptors (e.g., A and B) are ligated onto the ends of the fragments. These adaptors provide priming sequences for both amplification and sequencing of the sample-library fragments. One of the adaptors (e.g., Adaptor B) contains a 5'-biotin tag or other tag that enables immobilization of the library onto beads (e.g., streptavidin coated beads). In step 1114, only gDNA fragments that include both Adaptor A and B are selected using avidin-blotting purification. The sstDNA library is assessed for its quality and the optimal amount (DNA copies per bead) needed for subsequent amplification is determined by titration. In step 1115, the sstDNA library is annealed and immobilized onto an excess of capture beads (e.g., streptavidin coated beads). The latter occurs under conditions that favor each bead to carry only a single sstDNA molecule. In step 1116, each bead is captured in its own microreactor, such as a well, which may optionally be addressable, or a picolitre-sized well. In step 1117, the bead-bound library is amplified using, e.g., emPCR. This can be accomplished by capturing each bead within a droplet of a PCR-reaction-mixture-in-oil-emulsion. Thus, the bead-bound library can be emulsified with the amplification reagents in a water-in-oil mixture. EmPCR enables the amplification of a DNA fragment immobilized on a bead from a single fragment to 10 million identical copies. This amplification step generates sufficient identical DNA fragments to obtain a strong signal in the subsequent sequencing step. The amplification step results in bead-immobilized, clonally amplified DNA fragments. The amplification on the bead results can result in each bead carrying at least one million, at least 5 million, or at least 10 million copies of the unique target nucleic acid.

The emulsion droplets can then be broken, genomic material on each bead may be denatured, and single-stranded nucleic acids clones can be deposited into wells, such as picolitre-sized wells, for further analysis including, but are not limited to quantifying said amplified nucleic acid, gene and exon-level expression analysis, methylation-state analysis, novel transcript discovery, sequencing, genotyping or resequencing. In step 1118, the sstDNA library beads are added to a DNA bead incubation mix (containing DNA polymerase) and are layered with enzyme beads (containing sulfurylase and luciferase as is described in U.S. Pat. Nos. 6,956,114 and 6,902,921) onto a fiber optic plate such as the PicoTiterPlate device. The fiber optic plate is centrifuged to deposit the beads into wells (~up to 50 or 45 microns in diameter). The layer of enzyme beads ensures that the DNA beads remain positioned in the wells during the sequencing reaction. The bead-deposition process maximizes the number of wells that contain a single amplified library bead (avoiding more than one sstDNA library bead per well).

Preferably, each well contains a single amplified library bead. In step 1119, the loaded fiber optic plate (e.g., Pico-TiterPlate device) is then placed into a sequencing apparatus (e.g., the Genome Sequencer 20 Instrument). Fluidics subsystems flow sequencing reagents (containing buffers and nucleotides) across the wells of the plate. Nucleotides are flowed sequentially in a fixed order across the fiber optic plate during a sequencing run. In step 1120, each of the hundreds of thousands of beads with millions of copies of DNA is sequenced in parallel during the nucleotide flow. If a nucleotide complementary to the template strand is flowed into a well, the polymerase extends the existing DNA strand by adding nucleotide(s) which transmits a chemilluminescent signal. In step 1122, the addition of one (or more) nucleotide(s) results in a reaction that generates a chemilluminescent signal that is recorded by a digital camera or CCD camera in the instrument. The signal strength of the chemilluminescent signal is proportional to the number of nucleotides added. Finally, in step 1124, a computer program product comprising an executable logic processes the chemilluminescent signal produced by the sequencing reaction. Such logic enables whole genome sequencing for de novo or resequencing projects.

In some embodiments, high-throughput sequencing is performed using Clonal Single Molecule Array (Solexa, Inc.) or sequencing-by-synthesis (SBS) utilizing reversible terminator chemistry. These technologies are described in part in U.S. Pat. Nos. 6,969,488; 6,897,023; 6,833,246; 6,787,308; and US Publication Application Nos. 20040106110; 20030064398; 20030022207; and Constans, A., The Scientist 2003, 17(13):36.

Figure 12:
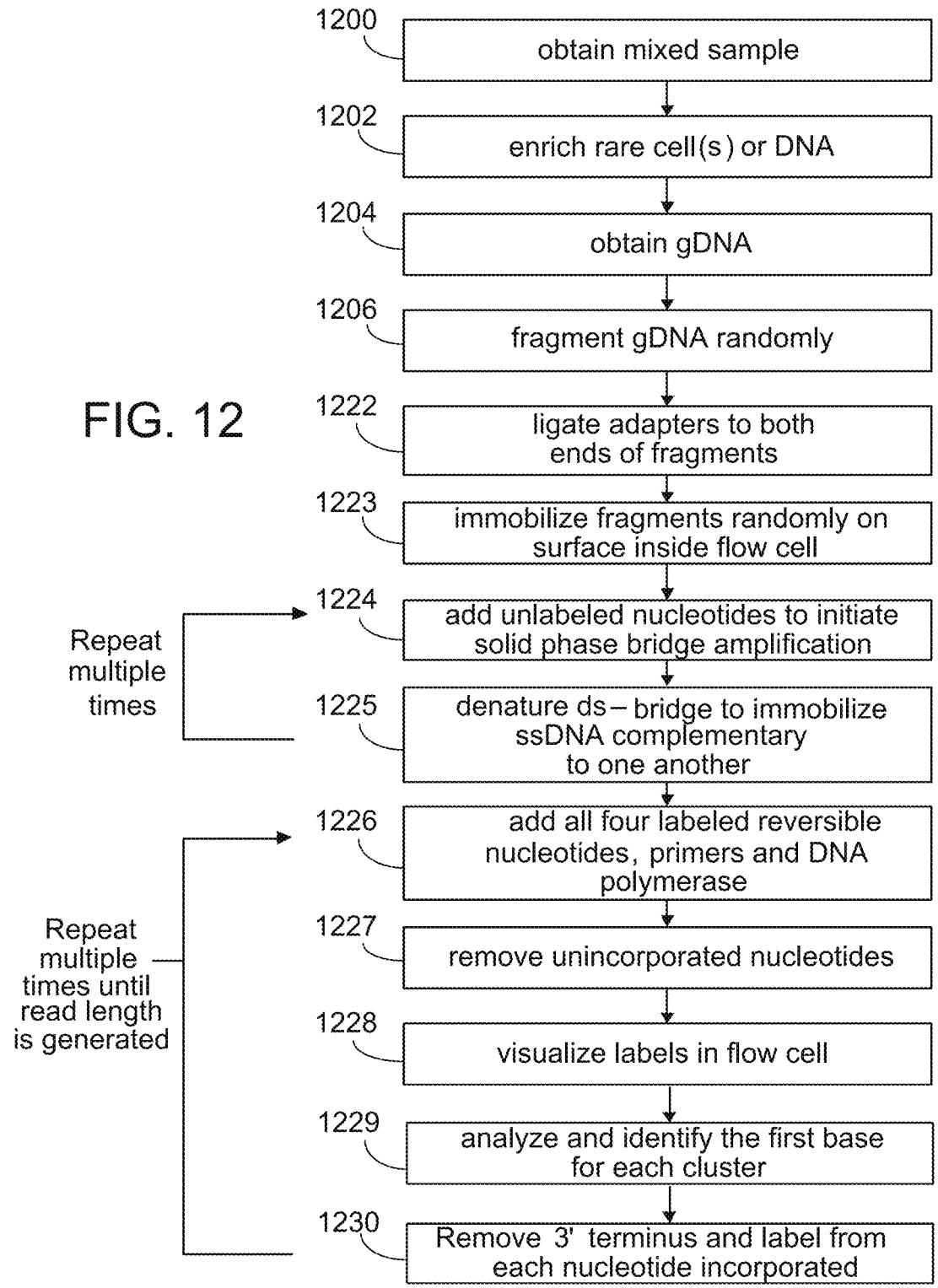
FIG. 12 illustrates one embodiment for high-throughput sequencing of rare cell(s) or rare DNA using, e.g., clonal single molecule arrays technology (e.g., Solexa, Inc.).

FIG. 12 illustrates a first embodiment using the SBS approach described above.

First, in step 1200 a sample comprising one or more rare cells (e.g., fetal or CTC) and one or more non-rare cells (e.g., RBC's) is obtained from an animal, such as a human. In step 1202, rare cells, rare DNA (e.g., rare nuclei), or raremRNA is enriched using one or more methods disclosed herein or known in the art. Preferably, rare cells are enriched by flowing the sample through an array of obstacles that selectively directs particles or cells of different hydrodynamic sizes into different outlets.

In step 1204, enriched genetic material e.g., gDNA is obtained using methods known in the art or disclosed herein. In step 1206, the genetic material e.g., gDNA is randomly fragmented. In step 1222, the randomly fragmented gDNA is ligated with adapters on both ends. In step 1223, the genetic material, e.g., ssDNA are bound randomly to inside surface of a flow cell channels. In step 1224, unlabeled nucleotides and enzymes are added to initiate solid phase bridge amplification. The above step results in genetic material fragments becoming double stranded and bound at either end to the substrate. In step 1225, the double stranded bridge is denatured to create to immobilized single stranded genomic DNA (e.g., ssDNA) sequencing complementary to one another. The above bridge amplification and denaturation steps are repeated multiple times (e.g., at least 10, 50, 100, 500, 1,000, 5,000, 10,000, 50,000, 100,000, 500,000, 1,000,000, 5,000,000 times) such that several million dense clusters of dsDNA (or immobilized ssDNA pairs complementary to one another) are generated in each channel of the flow cell. In step 1226, the first sequencing cycle is initiated by adding all four labeled reversible terminators, primers, and DNA polymerase enzyme to the flow cell. This sequencing-by-synthesis (SBS) method utilizes four fluorescently labeled modified nucleotides that are especially created to posses a reversible termination property, which allow each cycle of the sequencing reaction to occur simultaneously in the presence of all four nucleotides (A, C, T, G). In the presence of all four nucleotides, the polymerase is able to select the correct base to incorporate, with the natural competition between all four alternatives leading to higher accuracy than methods where only one nucleotide is present in the reaction mix at a time which require the enzyme to reject an incorrect nucleotide. In step 1227, all unincorporated labeled terminators are then washed off. In step 1228, laser is applied to the flow cell. Laser excitation captures an image of emitted fluorescence from each cluster on the flow cell. In step 1229, a computer program product comprising a computer executable logic records the identity of the first base for each cluster. In step 1230, before initiated the next sequencing step, the 3' terminus and the fluorescence from each incorporated base are removed.

Subsequently, a second sequencing cycle is initiated, just as the first was by adding all four labeled reversible terminators, primers, and DNA polymerase enzyme to the flow cell. A second sequencing read occurs by applying a laser to the flow cell to capture emitted fluorescence from each cluster on the flow cell which is read and analyzed by a computer program product that comprises a computer executable logic to identify the first base for each cluster. The above sequencing steps are repeated as necessary to sequence the entire gDNA fragment. In some cases, the above steps are repeated at least 5, 10, 50, 100, 500, 1,000, 5,000, to 10,000 times.

In some embodiments, high-throughput sequencing of mRNA or gDNA can take place using AnyDotchips (Genovoxx, Germany), which allows for the monitoring of biological processes (e.g., mRNA expression or allele variability (SNP detection). In particular, the AnyDot.chips allow for 10×-50× enhancement of nucleotide fluorescence signal detection. AnyDot.chips and methods for using them are described in part in International Publication Application Nos. WO 02088382, WO 03020968, WO 03031947, WO 2005044836, PCT/EP 05/05657, PCT/EP 05/05655; and German Patent Application Nos. DE 101 49 786, DE 102 14 395, DE 103 56 837, DE 10 2004 009 704, DE 10 2004 025 696, DE 10 2004 025 746, DE 10 2004 025 694, DE 10 2004 025 695, DE 10 2004 025 744, DE 10 2004 025 745, and DE 10 2005 012 301.

Figure 13:
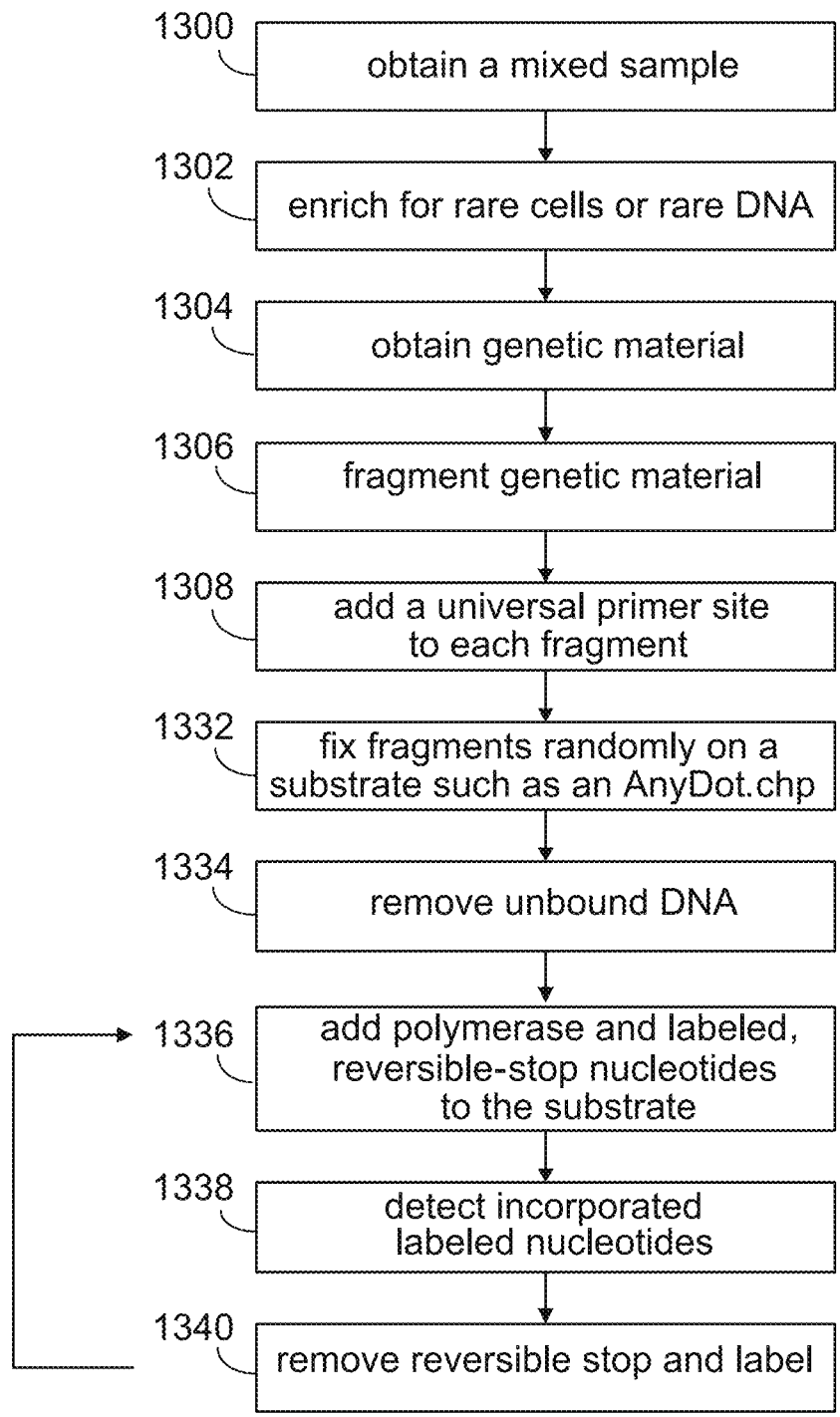
FIG. 13 illustrates one embodiment for high-throughput sequencing of rare cell(s) or rare DNA using, e.g., single base polymerization using enhanced nucleotide fluorescence (e.g., Genovoxx GmbH).
Figure 14A:
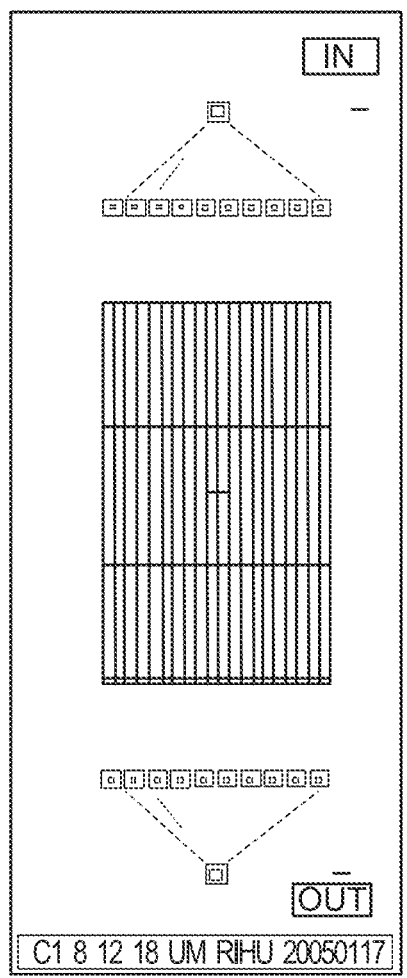
FIGS. 14A-14D illustrate one embodiment of a device used to separate cells according to their size.
Figure 14B:
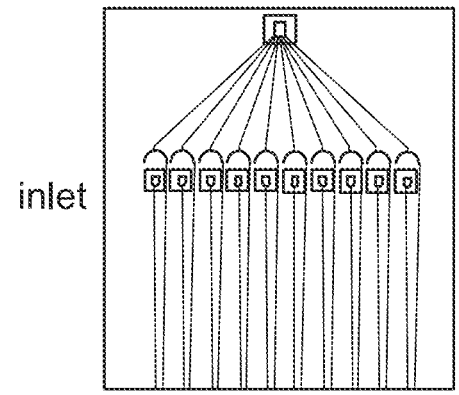
Figure 14C:
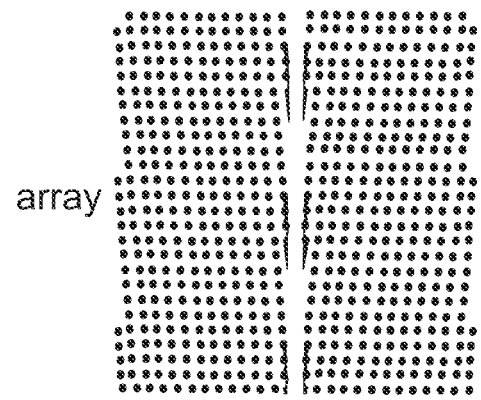
Figure 14D:
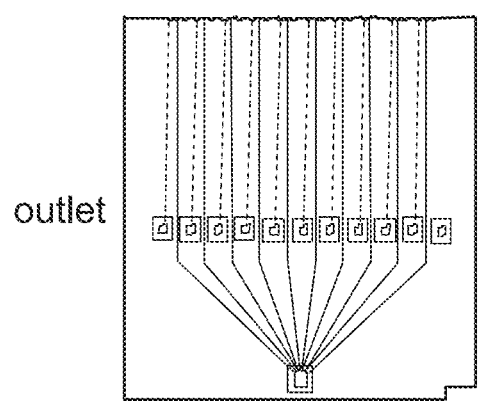
Figure 16A:
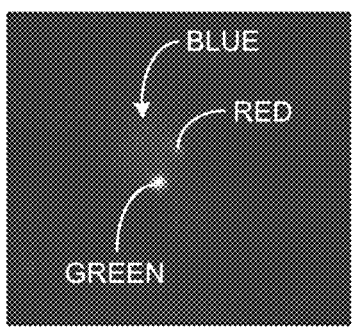
FIGS. 16A-16F illustrate isolation of CD-71 positive population from a nucleated cell fraction.
Figure 16B:
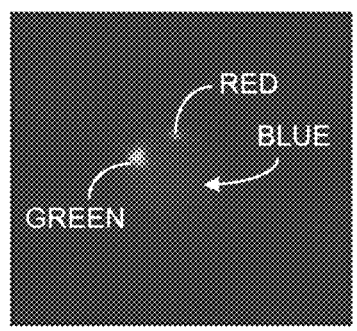
Figure 16C:
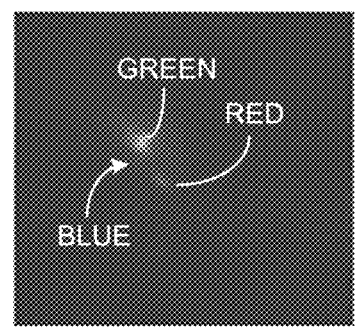
Figure 16D:
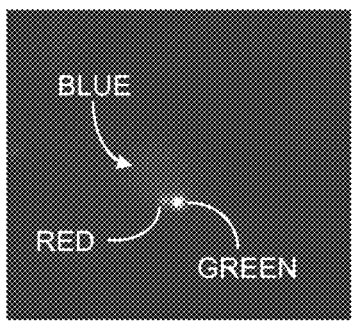
Figure 16E:
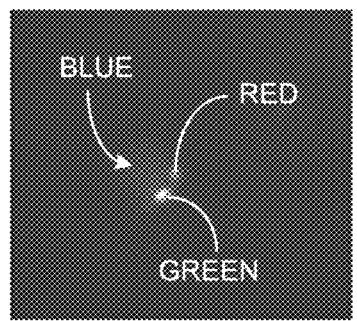
Figure 16F:
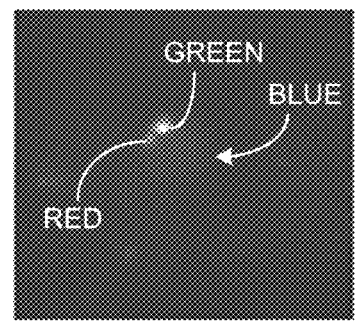

An overview of one embodiment of the present invention is illustrated in FIG. 13.

First, in step 1300 a sample comprising one or more rare cells (e.g., fetal, epithelial or CTC) and one or more non-rare cells (e.g., RBC's) is obtained from an animal, such as a human. In step 1302, rare cells or rare genetic material (e.g., gDNA or RNA) is enriched using one or more methods disclosed herein or known in the art. Preferably, rare cells are enriched by flowing the sample through an array of obstacles that selectively directs particles or cells of different hydrodynamic sizes into different outlets. In step 1304, genetic material is obtained from the enriched sample. In step 1306, the genetic material (e.g., gDNA) is fragmented into millions of individual nucleic acid molecules and in step 1308, a universal primer binding site is added to each fragment (nucleic acid molecule). In step 1332, the fragments are randomly distributed, fixed and primed on a surface of a substrate, such as an AnyDot.chip. Distance between neighboring molecules averages 0.1-10 μm or about 1 μm. A sample is applied by simple liquid exchange within a microfluidic system. Each $mm^2$ contains 1 million single DNA molecules ready for sequencing. In step 1334, unbound DNA fragments are removed from the substrate; and in step 1336, a solution containing polymerase and labeled nucleotide analogs having a reversible terminator that limits extension to a single base, such as AnyBase.nucleotides are applied to the substrate. When incorporated into the primer-DNA hybrid, such nucleotide analogs cause a reversible stop of the primer-extension (terminating property of nucleotides). This step represents a single-base extension. During the stop, incorporated bases, which include a fluorescence label, can be detected on the surface of the substrate.

In step 1338, fluorescent dots are detected by a single-molecule fluorescence detection system (e.g., fluorescent microscope). In some cases, a single fluorescence signal (300 nm in diameter) can be properly tracked over the complete sequencing cycles (see below). After detection of the single-base, in step 1340, the terminating property and fluorescent label of the incorporated nucleotide analogs (e.g., AnyBase.nucleotides) are removed. The nucleotides are now extendable similarly to native nucleotides. Thus, steps 1336-1340 are thus repeated, e.g., at least 2, 10, 20, 100, 200, 1,000, 2,000 times. For generating sequence data that can be compared with a reference database (for instance human mRNA database of the NCBI), length of the sequence snippets has to exceed 15-20 nucleotides. Therefore, steps 1 to 3 are repeated until the majority of all single molecules reaches the required length. This will take, on average, 2 offers of nucleotide incorporations per base.

Other high-throughput sequencing systems include those disclosed in Venter, J., et al. Science 16 Feb. 2001; Adams, M. et al. Science 24 Mar. 2000; and M. J. Levene, et al. Science 299:682-686, January 2003; as well as US Publication Application No. 20030044781 and 2006/0078937. Overall such system involve sequencing a target nucleic acid molecule having a plurality of bases by the temporal addition of bases via a polymerization reaction that is measured on a molecule of nucleic acid, i.e. the activity of a nucleic acid polymerizing enzyme on the template nucleic acid molecule to be sequenced is followed in real time. Sequence can then be deduced by identifying which base is being incorporated into the growing complementary strand of the target nucleic acid by the catalytic activity of the nucleic acid polymerizing enzyme at each step in the sequence of base additions. A polymerase on the target nucleic acid molecule complex is provided in a position suitable to move along the target nucleic acid molecule and extend the oligonucleotide primer at an active site. A plurality of labeled types of nucleotide analogs are provided proximate to the active site, with each distinguishable type of nucleotide analog being complementary to a different nucleotide in the target nucleic acid sequence. The growing nucleic acid strand is extended by using the polymerase to add a nucleotide analog to the nucleic acid strand at the active site, where the nucleotide analog being added is complementary to the nucleotide of the target nucleic acid at the active site. The nucleotide analog added to the oligonucleotide primer as a result of the polymerizing step is identified. The steps of providing labeled nucleotide analogs, polymerizing the growing nucleic acid strand, and identifying the added nucleotide analog are repeated so that the nucleic acid strand is further extended and the sequence of the target nucleic acid is determined.

In some embodiments, cDNAs, which are reverse transcribed from mRNAs obtained from fetal or maternal cells, are analyzed (e.g. SNP analysis or sequencing) by the methods disclosed herein. The type and abundance of the cDNAs can be used to determine whether a cell is a fetal cell (such as by the presence of Y chromosome specific transcripts) or whether the fetal cell has a genetic abnormality (such as aneuploidy, abundance or type of alternative transcripts or problems with DNA methylation or imprinting).

In one embodiment, fetal or maternal cells are enriched using one or more methods disclosed herein. Preferably, fetal cells are enriched by flowing the sample through an array of obstacles that selectively directs particles or cells of different hydrodynamic sizes into different outlets such that fetal cells and cells larger than fetal cells are directed into a first outlet and one or more cells or particles smaller than the rare cells are directed into a second outlet.

Total RNA or poly-A mRNA is then obtained from enriched cell(s) (fetal or maternal cells) using purification techniques known in the art. Generally, about 1 µg-2 µg of total RNA is sufficient. Next, a first-strand complementary DNA (cDNA) is synthesized using reverse transcriptase and a single T7-oligo(dT) primer. Next, a second-strand cDNA is synthesized using DNA ligase, DNA polymerase, and RNase enzyme. Next, the double stranded cDNA (ds-cDNA) is purified.

Analyzing the rare cells to determine the existence of condition or disease may also include detecting mitochondrial DNA, telomerase, or a nuclear matrix protein in the enriched rare cell sample; detecting the presence or absence of perinuclear compartments in a cell of the enriched sample; or performing gene expression analysis, determining nucleic acid copy number, in-cell PCR, or fluorescence in-situ hybridization of the enriched sample.

In some embodiments, PCR-amplified single-strand nucleic acid is hybridized to a primer and incubated with a polymerase, ATP sulfurylase, luciferase, apyrase, and the substrates luciferin and adenosine 5' phosphosulfate. Next, deoxynucleotide triphosphates corresponding to the bases A, C, G, and T (U) are added sequentially. Each base incorporation is accompanied by release of pyrophosphate, converted to ATP by sulfurylase, which drives synthesis of oxyluciferin and the release of visible light. Since pyrophosphate release is equimolar with the number of incorporated bases, the light given off is proportional to the number of nucleotides adding in any one step. The process repeats until the entire sequence is determined. In one embodiment, pyrosequencing analyzes DNA methylations, mutation and SNPs. In another embodiment, pyrosequencing also maps surrounding sequences as an internal quality control. Pyrosequencing analysis methods are known in the art.

In some embodiments, sequence analysis of the rare cell's genetic material may include a four-color sequencing by ligation scheme (degenerate ligation), which involves hybridizing an anchor primer to one of four positions. Then an enzymatic ligation reaction of the anchor primer to a population of degenerate nonamers that are labeled with fluorescent dyes is performed. At any given cycle, the population of nonamers that is used is structure such that the identity of one of its positions is correlated with the identity of the fluorophore attached to that nonamer. To the extent that the ligase discriminates for complementarity at that queried position, the fluorescent signal allows the inference of the identity of the base. After performing the ligation and four-color imaging, the anchor primer:nonamer complexes are stripped and a new cycle begins. Methods to image sequence information after performing ligation are known in the art.

Another embodiment includes kits for performing some or all of the steps of the invention. The kits may include devices and reagents in any combination to perform any or all of the steps. For example, the kits may include the arrays for the size-based separation or enrichment, the device and reagents for magnetic separation and the reagents needed for the genetic analysis.

EXAMPLES

Example 1. Separation of Fetal Cord Blood

FIGS. 14A-14D shows a schematic of the device used to separate nucleated cells from fetal cord blood.

Dimensions:
100 mm×28 mm×1 mm

Array Design:
3 stages, gap size=18, 12 and 8 µm for the first, second and third stage, respectively.

Device Fabrication:
The arrays and channels were fabricated in silicon using standard photolithography and deep silicon reactive etching techniques. The etch depth is 140 µm. Through holes for fluid access are made using KOH wet etching. The silicon substrate was sealed on the etched face to form enclosed fluidic channels using a blood compatible pressure sensitive adhesive (9795, 3M, St Paul, Minn.).

Device Packaging:
The device was mechanically mated to a plastic manifold with external fluidic reservoirs to deliver blood and buffer to the device and extract the generated fractions.

Device Operation:
An external pressure source was used to apply a pressure of 2.0 PSI to the buffer and blood reservoirs to modulate fluidic delivery and extraction from the packaged device.

Experimental Conditions:
Human fetal cord blood was drawn into phosphate buffered saline containing Acid Citrate Dextrose anticoagulants. lmL of blood was processed at 3 mL/hr using the device described above at room temperature and within 48 hrs of draw. Nucleated cells from the blood were separated from enucleated cells (red blood cells and platelets), and plasma delivered into a buffer stream of calcium and magnesium-free Dulbecco's Phosphate Buffered Saline (14190-144, Invitrogen, Carlsbad, Calif.) containing 1% Bovine Serum Albumin (BSA) (A8412-100ML, Sigma-Aldrich, St Louis, Mo.) and 2 mM EDTA (15575-020, Invitrogen, Carlsbad, Calif.).

Measurement Techniques:
Cell smears of the product and waste fractions (FIG. 15A-15B) were prepared and stained with modified Wright-Giemsa (WG16, Sigma Aldrich, St. Louis, Mo.).

Performance:
Fetal nucleated red blood cells were observed in the product fraction (FIG. 15A) and absent from the waste fraction (FIG. 15B).

Example 2. Isolation of Fetal Cells from Maternal Blood

The device and process described in detail in Example 1 were used in combination with immunomagnetic affinity enrichment techniques to demonstrate the feasibility of isolating fetal cells from maternal blood.

Experimental Conditions:
blood from consenting maternal donors carrying male fetuses was collected into $K_2$EDTA vacutainers (366643, Becton Dickinson, Franklin Lakes, N.J.) immediately following elective termination of pregnancy. The undiluted blood was processed using the device described in Example 1 at room temperature and within 9 hrs of draw. Nucleated cells from the blood were separated from enucleated cells (red blood cells and platelets), and plasma delivered into a buffer stream of calcium and magnesium-free Dulbecco's Phosphate Buffered Saline (14190-144, Invitrogen, Carlsbad, Calif.) containing 1% Bovine Serum Albumin (BSA) (A8412-100ML, Sigma-Aldrich, St Louis, Mo.). Subsequently, the nucleated cell fraction was labeled with anti-CD71 microbeads (130-046-201, Miltenyi Biotech Inc., Auburn, Calif.) and enriched using the MiniMACS™ MS column (130-042-201, Miltenyi Biotech inc., Auburn, Calif.) according to the manufacturer's specifications. Finally, the CD71-positive fraction was spotted onto glass slides.

Measurement Techniques:
Spotted slides were stained using fluorescence in situ hybridization (FISH) techniques according to the manufacturer's specifications using Vysis probes (Abbott Laboratories, Downer's Grove, Ill.). Samples were stained from the presence of X and Y chromosomes. In one case, a sample prepared from a known Trisomy 21 pregnancy was also stained for chromosome 21.

Figure 17:
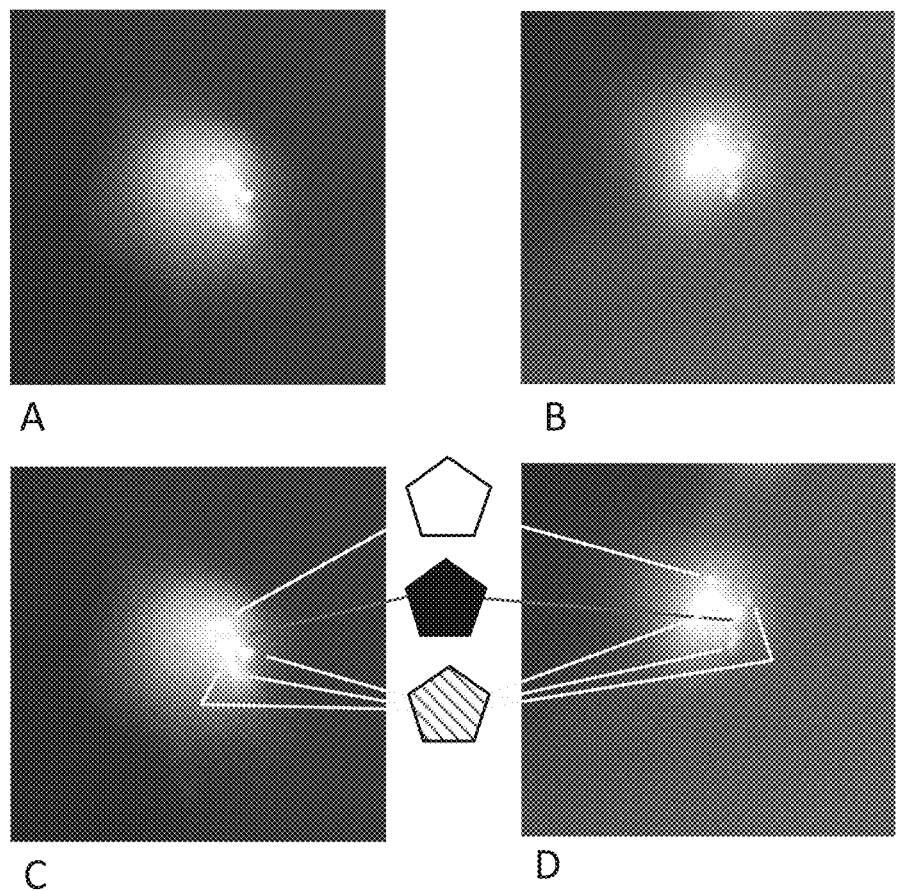
FIG. 17 illustrates trisomy 21 pathology.

Performance:
Isolation of fetal cells was confirmed by the reliable presence of male cells in the CD71-positive population prepared from the nucleated cell fractions (FIG. 16). In the single abnormal case tested, the trisomy 21 pathology was also identified (FIG. 17).

Example 3. Confirmation of the Presence of Male Fetal Cells in Enriched Samples Confirmation of the presence of a male fetal cell in an enriched sample is performed using qPCR with primers specific for DYZ, a marker repeated in high copy number on the Y chromosome. After enrichment of fnRBC by any of the methods described herein, the resulting enriched fnRBC are binned by dividing the sample into 100 PCR wells. Prior to binning, enriched samples may be screened by FISH to determine the presence of any fnRBC containing an aneuploidy of interest. Because of the low number of fnRBC in maternal blood, only a portion of the wells will contain a single fnRBC (the other wells are expected to be negative for fnRBC). The cells are fixed in 2% Paraformaldehyde and stored at 4° C. Cells in each bin are pelleted and resuspended in 5 µl PBS plus 1 µl 20 mg/ml Proteinase K (Sigma # P-2308). Cells are lysed by incubation at 65° C. for 60 minutes followed by inactivation of the Proteinase K by incubation for 15 minutes at 95° C. For each reaction, primer sets (DYZ forward primer TCGAGTGCATTCCATTCCG; DYZ reverse primer ATGGAATGGCATCAAACGGAA; and DYZ Taqman Probe 6FAM-TGGCTGTCCATTCCA-MGBNFQ), TaqMan Universal PCR master mix, No AmpErase and water are added. The samples are run and analysis is performed on an ABI 7300: 2 minutes at 50° C., 10 minutes 95° C. followed by 40 cycles of 95° C. (15 seconds) and 60° C. (1 minute). Following confirmation of the presence of male fetal cells, further analysis of bins containing fnRBC is performed. Positive bins may be pooled prior to further analysis.

Figure 27:
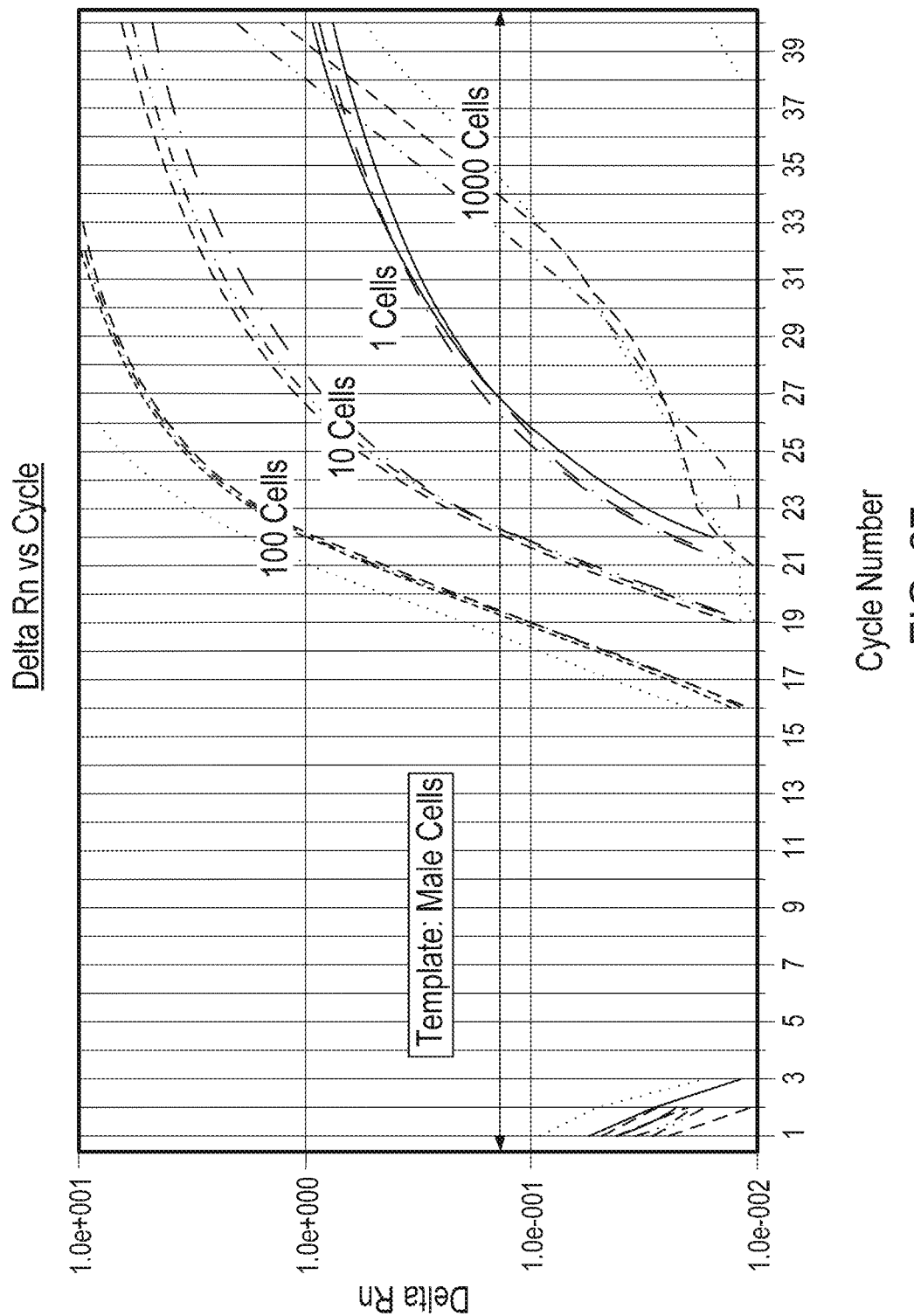
FIG. 27 illustrates the detection of single copies of a fetal cell genome by qPCR.

FIG. 27 shows the results expected from such an experiment. The data in FIG. 27 was collected by the following protocol. Nucleated red blood cells were enriched from cord cell blood of a male fetus by sucrose gradient two Heme Extractions (HE). The cells were fixed in 2% paraformaldehyde and stored at 4° C. Approximately 10×1000 cells were pelleted and resuspended each in 5 µl PBS plus 1 µl 20 mg/ml Proteinase K (Sigma # P-2308). Cells were lysed by incubation at 65° C. for 60 minutes followed by a inactivation of the Proteinase K by 15 minute at 95° C. Cells were combined and serially diluted 10-fold in PBS for 100, 10 and 1 cell per 6 µl final concentration were obtained. Six µl of each dilution was assayed in quadruplicate in 96 well format. For each reaction, primer sets (DYZ forward primer TCGAGTGCATTCCATTCCG; 0.9 uM DYZ reverse primer ATGGAATGGCATCAAACGGAA; and 0.5 uM DYZ TaqMan Probe 6FAM-TGGCTGTCCATTCCA-MGBNFQ), TaqMan Universal PCR master mix, No AmpErase and water were added to a final volume of 25 µl per reaction. Plates were run and analyzed on an ABI 7300: 2 minutes at 50° C., 10 minutes 95° C. followed by 40 cycles of 95° C. (15 seconds) and 60° C. (1 minute). These results show that detection of a single fnRBC in a bin is possible using this method.

Example 4. Confirmation of the Presence of Fetal Cells in Enriched Samples by STR Analysis Maternal blood is processed through a size-based separation module, with or without subsequent MHEM enhancement of fnRBCs. The enhanced sample is then subjected to FISH analysis using probes specific to the aneuploidy of interest (e.g., triploidy 13, triploidy 18, and XYY). Individual positive cells are isolated by "plucking" individual positive cells from the enhanced sample using standard micromanipulation techniques. Using a nested PCR protocol, STR marker sets are amplified and analyzed to confirm that the FISH-positive aneuploid cell(s) are of fetal origin. For this analysis, comparison to the maternal genotype is typical. An example of a potential resulting data set is shown in Table 2. Non-maternal alleles may be proven to be paternal alleles by paternal genotyping or genotyping of known fetal tissue samples. As can be seen, the presence of paternal alleles in the resulting cells, demonstrates that the cell is of fetal origin (cells #1, 2, 9, and 10). Positive cells may be pooled for further analysis to diagnose aneuploidy of the fetus, or may be further analyzed individually.

TABLE 2

STR locus alleles in maternal and fetal cells

| DNA Source | STR locus D14S | STR locus D16S | STR locus D8S | STR locus F13B | STR locus vWA |
|---|---|---|---|---|---|
| Maternal alleles | 14, 17 | 11, 12 | 12, 14 | 9, 9 | 16, 17 |
| Cell #1 alleles |  | 8 |  |  | 19 |
| Cell #2 alleles | 17 |  | 15 |  |  |
| Cell #3 alleles |  |  | 14 |  |  |
| Cell #4 alleles |  |  |  |  |  |
| Cell #5 alleles | 17 | 12 |  | 9 |  |
| Cell #6 alleles |  |  |  |  |  |
| Cell #7 alleles |  |  |  |  | 19 |
| Cell #8 alleles |  |  |  |  |  |
| Cell #9 alleles | 17 |  | 14 | 7, 9 | 17, 19 |
| Cell #10 alleles |  |  | 15 |  |  |

Example 5. Confirmation of the Presence of Fetal Cells in Enriched Samples by SNP Analysis Maternal blood is processed through a size-based separation module, with or without subsequent MHEM enhancement of fnRBCs. The enhanced sample is then subjected to FISH analysis using probes specific to the aneuploidy of interest (e.g., triploidy 13, triploidy 18, and XYY). Samples testing positive with FISH analysis are then binned into 96 microtiter wells, each well containing 15 µl of the enhanced sample. Of the 96 wells, 5-10 are expected to contain a single fnRBC and each well should contain approximately 1000 nucleated maternal cells (both WBC and mnRBC). Cells are pelleted and resuspended in 5 µl PBS plus 1 µl 20 mg/ml Proteinase K (Sigma # P-2308). Cells are lysed by incubation at 65° C. for 60 minutes followed by a inactivation of the Proteinase K by 15 minute at 95° C.

In this example, the maternal genotype (BB) and fetal genotype (AB) for a particular set of SNPs is known. The genotypes A and B encompass all three SNPs and differ from each other at all three SNPs. The following sequence from chromosome 7 contains these three SNPs (rs7795605, rs7795611 and rs7795233 indicated in brackets, respectively)

ATGCAGCAAGGCACAGACTAA[G/A]CAAGGAGA[G/C]GCAAAATTTTC [A/G]TAGGGGAGAGAAATGGGTCATT).

In the first round of PCR, genomic DNA from binned enriched cells is amplified using primers specific to the outer portion of the fetal-specific allele A and which flank the interior SNP (forward primer ATGCAGCAAGGCACA-GACTACG; reverse primer AGAGGG-GAGAGAAATGGGTCATT). In the second round of PCR, amplification using real time SYBR Green PCR is performed with primers specific to the inner portion of allele A and which encompass the interior SNP (forward primer CAAGGCACAGACTAAGCAAGGAGAG; reverse primer GGCAAAATTTTCATAGGGGAGAGAAATGGGTCATT).

Figure 28:
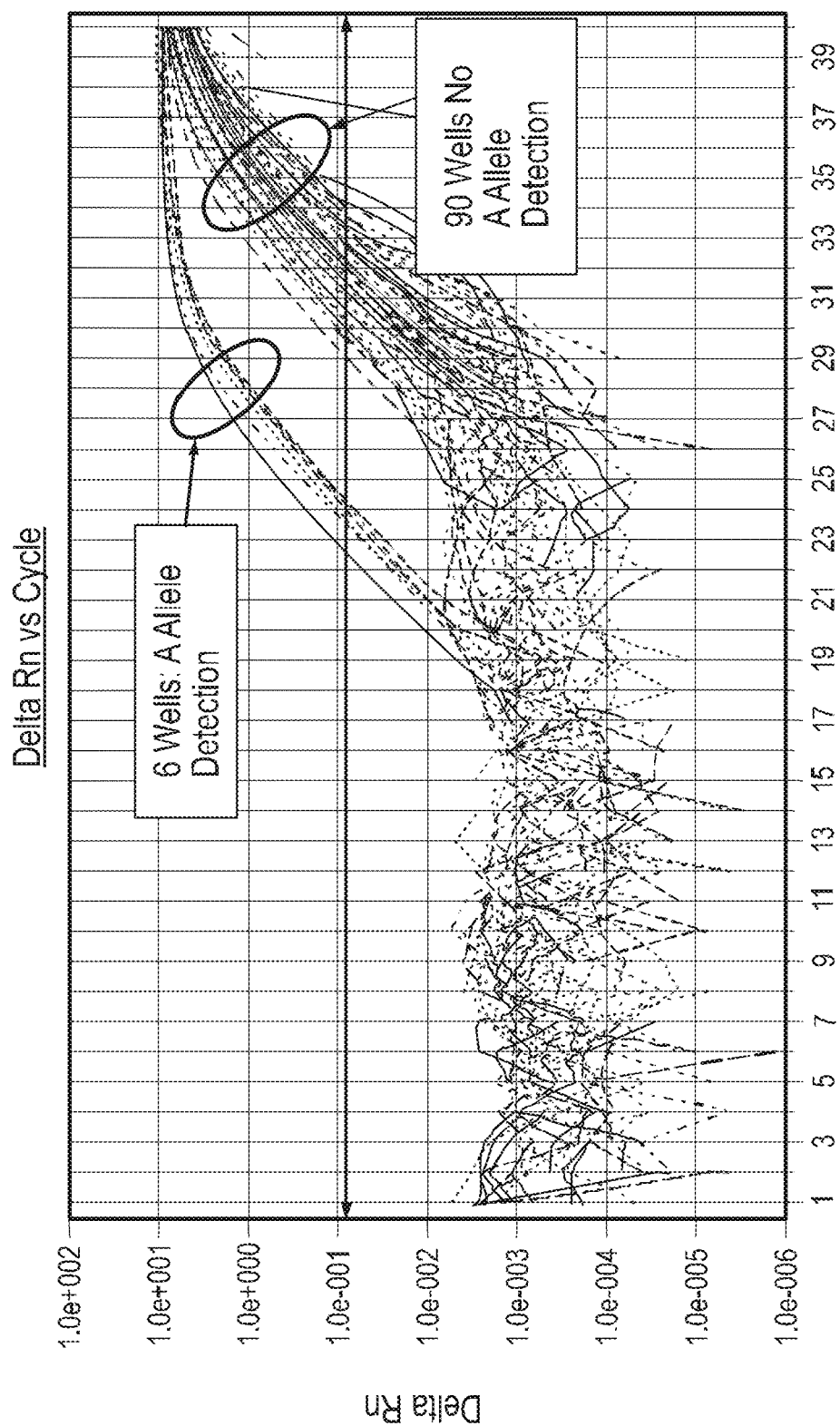
FIG. 28 illustrates detection of single fetal cells in binned samples by SNP analysis.
Figure 29:
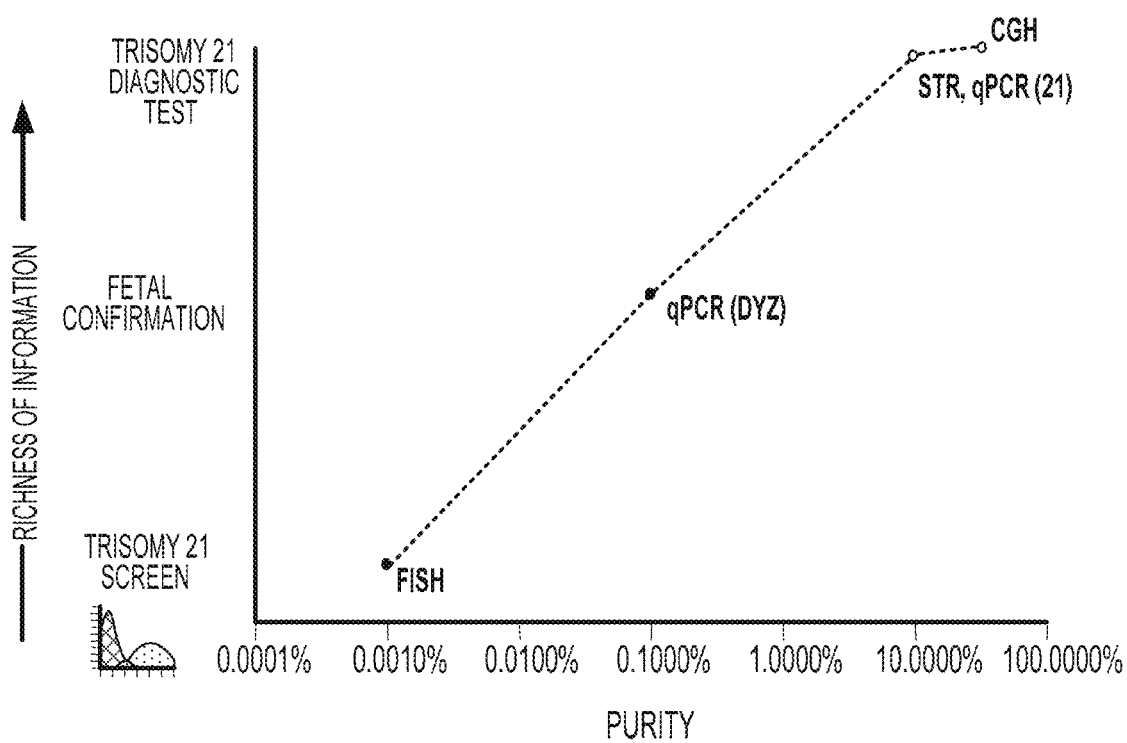
FIG. 29 illustrates a method of trisomy testing. The trisomy 21 screen is based on scoring of target cells obtained from maternal blood. Blood is processed using a cell separation module for hemoglobin enrichment (CSM-HE). Isolated cells are transferred to slides that are first stained and subsequently probed by FISH. Images are acquired, such as from bright field or fluorescent microscopy, and scored. The proportion of trisomic cells of certain classes serves as a classifier for risk of fetal trisomy 21. Fetal genome identification can performed using assays such as: (1) STR markers; (2) qPCR using primers and probes directed to loci, such as the multi-repeat DYZ locus on the Y-chromosome; (3) SNP detection; and (4) CGH (comparative genome hybridization) array detection.
Figure 30:
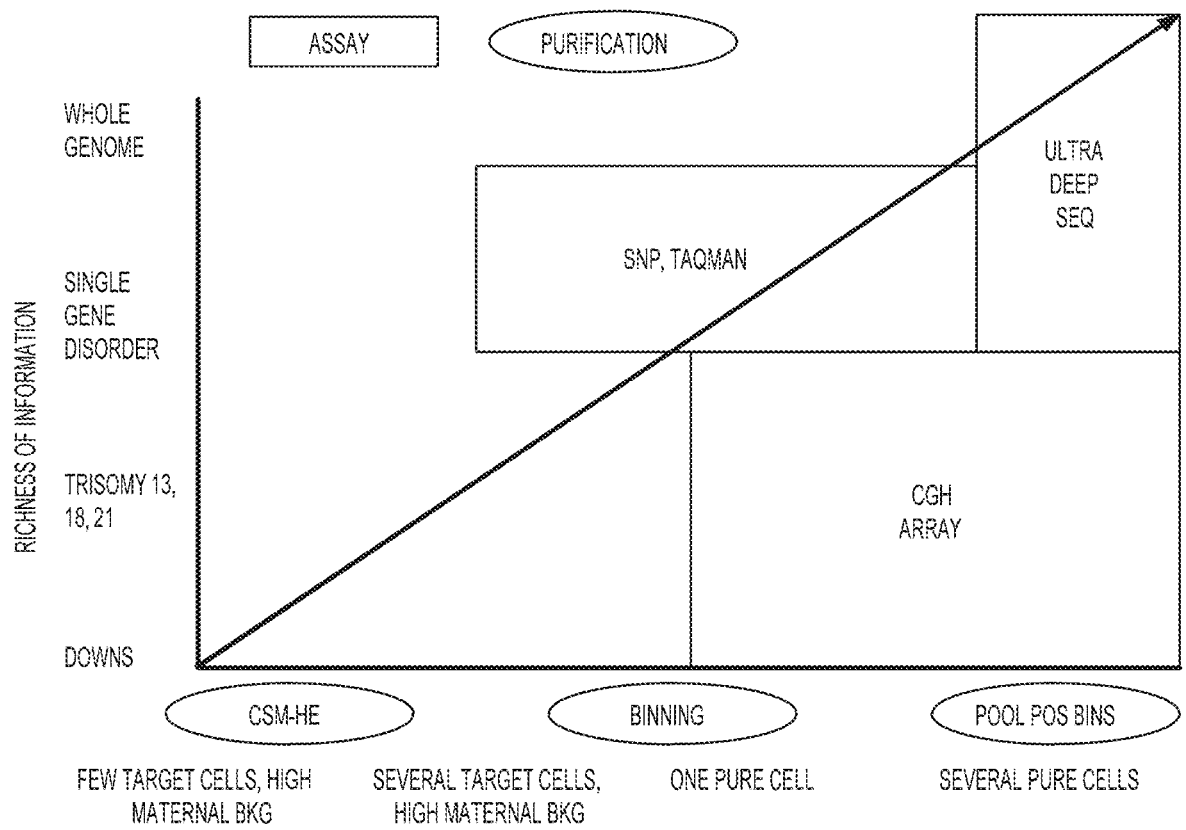
FIG. 30 illustrates assays that can produce information on the presence of aneuploidy and other genetic disorders in target cells. Information on aneuploidy and other genetic disorders in target cells may be acquired using technologies such as: (1) a CGH array established for chromosome counting, which can be used for aneuploidy determination and/or detection of intra-chromosomal deletions; (2) SNP/taqman assays, which can be used for detection of single nucleotide polymorphisms; and (3) ultra-deep sequencing, which can be used to produce partial or complete genome sequences for analysis.

Expected results are shown in FIG. 28. Here, six of the 96 wells test positive for allele A, confirming the presence of cells of fetal origin, because the maternal genotype (BB) is known and cannot be positive for allele A. DNA from positive wells may be pooled for further analysis or analyzed individually.

Example 6. Amplification and Sequencing of STRs for Fetal Diagnosis

Fetal cells or nuclei can be isolated as describe in the enrichment section or as described in example 1 and 2. DNA from the fetal cells or isolated nuclei from fetal cells can be obtained using any methods known in the art. STR loci can be chosen on the suspected trisomic chromosomes (X, 13, 18, or 21) and on other control chromosomes. These would be selected for high heterozygosity (variety of alleles) so that the paternal allele of the fetal cells is more likely to be distinct in length from the maternal alleles, with resulting improved power to detect. Di-, tri-, or tetra-nucleotide repeat loci can be used. The STR loci can then be amplified according the methods described in the amplification section.

For instance, the genomic DNA from the enriched fetal cells and a maternal control sample can be fragmented, and separated into single strands. The single strands of the target nucleic acids would be bound to beads under conditions that favor each single strand molecule of DNA to bind a different bead. Each bead would then be captured within a droplet of a PCR-reaction-mixture-in-oil-emulsion and PCR amplification occurs within each droplet. The amplification on the bead could results in each bead carrying at least one 10 million copies of the unique single stranded target nucleic acid. The emulsion would be broken, the DNA is denatured and the beads carrying single-stranded nucleic acids clones would be deposited into a picolitre-sized well for further analysis.

The beads can then be placed into a highly parallel sequencing by synthesis machine which can generate over 400,000 reads (~100 bp per read) in a single 4 hour run. Sequence by synthesis involves inferring the sequence of the template by synthesizing a strand complementary to the target nucleic acid sequence. The identity of each nucleotide would be detected after the incorporation of a labeled nucleotide or nucleotide analog into a growing strand of a complementary nucleic acid sequence in a polymerase reaction. After the successful incorporation of a label nucleotide, a signal would be measured and then nulled and the incorporation process would be repeated until the sequence of the target nucleic acid is identified. The allele abundances for each of the STRs loci can then be determined. The presence of trisomy would be determined by comparing abundance for each of the STR loci in the fetal cells with the abundance for each of the SRTs loci in a maternal control sample. The enrichment, amplification and sequencing methods described in this example allow for the analysis of rare alleles from fetal cells, even in circumstances where fetal cells are in a mixed sample comprising other maternal cells, and even in circumstances where other maternal cells dominate the mixture.

Example 7. Analysis of STR's Using Quantitative Fluorescence

Genomic DNA from enriched fetal cells and a maternal control sample will be genotyped for specific STR loci in order to assess the presence of chromosomal abnormalities, such as trisomy. Due to the small number of fetal cells typically isolated from maternal blood it is advantageous to perform a pre-amplification step prior to analysis, using a protocol such as improved primer extension pre-amplification (IPEP) PCR. Cell lysis is carried out in 10 ul High Fidelity buffer (50 mM Tris-HCL, 22 mM $(NH_4)_2SO_4$ 2.5 mM $MgCl_2$, pH 8.9) which also contained 4 mg/ml proteinase K and 0.5 vol % Tween 20 (Merck) for 12 hours at 48° C. The enzyme is then inactivated for 15 minutes at 94° C. Lysis is performed in parallel batches in 5 ul, 200 mM KOH, 50 mM dithiothreitol for 10 minutes at 65.degree. The batches are then neutralized with 5 ul 900 mM TrisHCl pH 8.3, 300 mM KCl. Preamplication is then carried out for each sample using completely randomized 15-mer primers (16 uM) and dNTP (100 uM) with 5 units of a mixture of Taq polymerase (Boehringer Mannheim) and Pwo polymerase (Boehringer Mannheim) in a ratio of 10:1 under standard PCR buffer conditions (50 mM Tris-HCL, 22 mM $(NH_4)_2 SO_4$, 2.5 mM $Mg_2$, pH 8.9, also containing 5% by vol. of DMSO) in a total volume of 60 ul with the following 50 thermal cycles: Step Temperature Time (1) 92° C. 1 Min 30 Sec; (2) 92° C. 40 Min (3) 37° C. 2 Min; (4) ramp: 0.10° C./sec to 55° C. (5) 55° C. 4 Min (6) 68° C. 30 Sec (7) go to step 2, 49 times (8) 8° C. 15'Min.

Dye labeled primers are then chosen from Table 3 based on STR loci on chromosomes of interest, such as 13,18, 21 or X. The primers are designed so that one primer of each pair contains a fluorescent dye, such as ROX, HEX, JOE, NED, FAM, TAMARA or LIZ. The primers are placed into multiplex mixes based on expected product size, fluorescent tag compatibility and melting temperature. This allows multiple STR loci to be assayed at once and yet still conserves the amount of initial starting material required. All primers are initially diluted to a working dilution of 10 pM. The primers are then combined in a cocktail that has a final volume of 40 ul. Final primer concentration is determined by reaction optimization. Additional PCR grade water is added if the primer mix is below 40 ul. A reaction mix containing 6 ul of Sigma PCR grade water, 1.25 ul of Perkin Elmer Goldamp PCR buffer, 0.5 ul of dNTPs, 8 ul of the primer cocktail, 0.12 ul of Perkin Elmer Taq Gold Polymerase and 1.25 ul of Mg (25 mM) is mixed for each sample. To this a 1 ul sample containing preamplified DNA from enriched fetal cells or maternal control genomic DNA is added.

The reaction mix is amplified in a DNA thermocyler, (PTC-200; MJ Research) using an amplification cycle optimized for the melting temperature of the primers and the amount of sample DNA.

The amplification product will then analyzed using an automated DNA sequencer system, such as the ABI 310, 377, 3100, 3130, 3700 or 3730, or the Li-Cor 4000, 4100, 4200 or 4300. For example when the amplification products are prepared for analysis on a ABI 377 sequencer, 6 ul of products will be removed and combined with 1.6 ul of loading buffer mix. The master loading buffer mix contains 90 ul deionized formamide combined with 25 ul Perkin Elmer loading dye and 10 ul of a size standard, such as the ROX 350 size standard. Various other standards can be used interchangeably depending on the sizes of the labeled PCR products. The loading buffer and sample are then heat denatured at 95° C. for 3 minutes followed by flash cooling on ice. 2 ul of the product/buffer mix is then electrophoresed on a 12 inch 6% (19:I) polyacrylamide gel on an ABI 377 sequencer.

The results are then analyzed using ABI Genotyper software. The incorporation of a fluorochrome during amplification allows product quantification for each chromosome specific STR, with 2 fluorescent peaks observed in a normal heterozygous individual with an approximate ratio of 1:1. By comparison in trisomic samples, either 3 fluorescent peaks with a ratio of 1:1:1 (trialleleic) or 2 peaks with a ratio of around 2:1(diallelic) are observed. Using this method screening may be carried out for common trisomies and sex chromosome aneuploidy in a single $reaL_4$,DNA,M

TABLE 3

Primer Sets for STRs on Chromsomes 13, 18, 21 and X

| Ch. | STR Marker | Primer 1 | Primer 2 |
|---|---|---|---|
| 13 | D13S317 | 5ACAGAAGTCTGGGATGTGGA (SEQ ID NO 1) | GCCCAAAAAGACAGACAGAA (SEQ ID NO 2) |
|  | D13S1493 | ACCTGTTGTATGGCAGCAGT (SEQ ID NO 3) | AGTTGACTCTITCCCCAACTA (SEQ ID NO 4) |
|  | D13S1807 | TTTGGTAAGAAAAACATCTCCC (SEQ ID NO 5) | GGCTGCAGTTAGCTGTCATT (SEQ ID NO 6) |
|  | D13S256 | CCTGGGCAACAAGAGCAAA (SEQ ID NO 7) | AGCAGAGAGACATAATTGTG (SEQ ID NO 8) |
|  | D13S258- | ACCTGCCAAATTTTACCAGG (SEQ ID NO 9) | GACAGAGAGGGAATAAACC (SEQ ID NO 10) |

TABLE 3-continued

Primer Sets for STRs on Chromsomes 13, 18, 21 and X

| Ch. | STR Marker | Primer 1 | Primer 2 |
|---|---|---|---|
| | D13S285 | ATATATGCACATCCATCCATG (SEQ ID NO 11) | GGCCAAAGATAGATAGCAAGGTA (SEQ ID NO 12) |
| | D13S303 | ACATCGCTCCTTACCCCATC (SEQ ID NO 13) | TGTACCCATTAACCATCCCA (SEQ ID NO 14) |
| | D13S317 | ACAGAAGTCTGGGATGTGGA (SEQ ID NO 15) | GCCCAAAAAGACAGACAGAA (SEQ ID NO 16) |
| | D13S779 | AGAGTGAGATTCTGTCTCAATTAA (SEQ ID NO 17) | GGCCCTGTGTAGAAGCTGTA (SEQ ID NO 18) |
| | D13S787 | ATCAGGATTCCAGGAGGAAA (SEQ ID NO 19) | ACCTGGGAGGCGGAGCTC (SEQ ID NO 20) |
| | D13S793 | GGCATAAAAATAGTACAGCAAGC (SEQ ID NO 21) | ATTTGAACAGAGGCATGTAC (SEQ ID NO 22) |
| | D13S796 | CATGGATGCAGAATTCACAG (SEQ ID NO 23) | TCATCTCCCTGTTTGGTAGC (SEQ ID NO 24) |
| | D13S800 | AGGGATCTTCAGAGAAACAGG (SEQ ID NO 25) | TGACACTATCAGCTCTCTGGC (SEQ ID NO 26) |
| | D13S894 | GGTGCTTGCTGTAAATATAATTG (SEQ ID NO 27) | CACTACAGCAGATTGCACCA (SEQ ID NO 28) |
| 18 | D18S51 | CAAACCCGACTACCAGCAAC (SEQ ID NO 29) | GAGCCATGTTCATGCCACTG (SEQ ID NO 30) |
| | D18S1002 | CAAAGAGTGAATGCTGTACAAACAGC (SEQ ID NO 31) | CAAGATGTGAGTGTGCTTTCAGGAG (SEQ ID NO 32) |
| | D18S1357 | ATCCCACAGGATGCCTATTT (SEQ ID NO 33) | ACGGGAGCTTTTGAGAAGTT (SEQ ID NO 34) |
| | D18S1364 | TCAAATTTTTAAGTCTCACCAGG (SEQ ID NO 35) | GCCTGTAGAAAGCAACAACC (SEQ ID NO 36) |
| | D18S1370 | GGTGACAGAGCAAGACCTTG (SEQ ID NO 37) | GCCTCTTGTCATCCCAAGTA (SEQ ID NO 38) |
| | D18S1371 | CTCTCTTCATCCACCATTGG (SEQ ID NO 39) | GCTGTAAGAGACCTGTGTTG (SEQ ID NO 40) |
| | D18S1376 | TGGAACCACTTCATTCTIGG (SEQ ID NO 41) | ATTTCAGACCAAGATAGGC (SEQ ID NO 42) |
| | D18S1390 | CCTATTTAAGTTTCTGTAAGG (SEQ ID NO 43) | ATGGTGTAGACCCTGTGGAA (SEQ ID NO 44) |
| | D18S499 | CTGCACAACATAGTGAGACCTG (SEQ ID NO 45) | AGATTACCCAGAAATGAGATCAGC (SEQ ID NO 46) |
| | D18S535 | TCATGTGACAAAAGCCACAC (SEQ ID NO 47) | AGACAGAAATATAGATGAGAATGCA (SEQ ID NO 48) |
| | D18S535 | TCATGTGACAAAAGCCACAC (SEQ ID NO 49) | AGACAGAAATATAGATGAGAATGCA (SEQ ID NO 50) |
| | D18S542 | TTTCCAGTGGAAACCAAACT (SEQ ID NO 51) | TCCAGCAACAACAAGAGACA (SEQ ID NO 52) |
| | D18S843 | GTCCTCATCCTGTAAAACGGG (SEQ ID NO 53) | CCACTAACTAGTTTGTGACTTTGG (SEQ ID NO 54) |
| | D18S851 | CTGTCCTCTAGGCTCATTTAGC (SEQ ID NO 55) | TTATGAAGCAGTGATGCCAA (SEQ ID NO 56) |
| | D18S858 | AGCTGGAGAGGGATAGCATT (SEQ ID NO 57) | TGCATTGCATGAAAGTAGGA (SEQ ID NO 58) |
| | D18S877 | GATGATAGAGATGGCACATGA (SEQ ID NO 59) | TCTTCATACATGCTTTATCATGC (SEQ ID NO 60) |
| 21 | D21S11 | GTGAGTCAATTCCCCAAG (SEQ ID NO 61) | GTTGTATTAGTCAATGTTCTCC (SEQ ID NO 62) |
| | D21S1411 | ATGATGAATGCATAGATGGATG (SEQ ID NO 63) | AATGTGTGTCCTECCAGGC (SEQ ID NO 64) |
| | D21S1413 | TTGCAGGGAAACCACAGTT (SEQ ID NO 65) | TCCTTGGAATAAATTCCCGG (SEQ ID NO 66) |
| | D21S1432 | CTTAGAGGGACAGAACTAATAGGC (SEQ ID NO 67) | AGCCTATTGTGGGTTTGTGA (SEQ ID NO 68) |
| | D21S1437 | ATGTACATGTGTCTGGGAAGG (SEQ ID NO 69) | TTCTCTACATATTTACTGCCAACA (SEQ ID NO 70) |
| | D21S1440 | GAGTTTGAAAATAAAGTGTTCTGC (SEQ ID NO 71) | CCCCACCCCTTTTAGTTTTA (SEQ ID NO 72) |
| | D21S1446 | ATGTACGATACGTAATACTTGACAA (SEQ ID NO 73) | GTCCCAAAGGACCTGCTC (SEQ ID NO 74) |
| | D21S2052 | GCACCCCTTTATACTTGGGTG (SEQ ID NO 75) | TAGTACTCTACCATCCATCTATCCC (SEQ ID NO 76) |
| | D21S2055 | AACAGAACCAATAGGCTATCTATC (SEQ ID NO 77) | TACAGTAAATCACTTGGTAGGAGA (SEQ ID NO 78) |
| X | SBMA | TCCGCGAAGTGAAGAAC (SEQ ID NO 79) | CTTGGGGAGAACCATCCTCA (SEQ ID NO 80) |
| | DXS1047 | CCGGCTACAAGTGATGTCTA (SEQ ID NO 81) | CCTAGGTAACATAGTGAGACCTTG (SEQ ID NO 82) |
| | DXS1068 | CCTCTAAAGCATAGGGTCCA (SEQ ID NO 83) | CCCATCTGAGAACACGCTG (SEQ ID NO 84) |
| | DXS1283E | AGTTTAGGAGATTATCAAGCTGG (SEQ ID NO 85) | GTTCCCATAATAGATGTATCCAG (SEQ ID NO 86) |
| | DXS6789 | TTGGTACTTAATAAACCCTCTTTT (SEQ ID NO 87) | CTAGAGGGACAGAACCAATAGG (SEQ ID NO 88) |
| | DXS6795 | TGTCTGCTAATGAATGATTTGG (SEQ ID NO 89) | CCATCCCCTAAACCTCTCAT (SEQ ID NO 90) |
| | DXS6800 | GTGGGACCTTGTGATTGTGT (SEQ ID NO 91) | CTGGCTGACACTTAGGGAAA (SEQ ID NO 92) |
| | DXS6810 | ACAGAAAACCTTTTGGGACC (SEQ ID NO 93) | CCCAGCCCTGAATATTATCA (SEQ ID NO 94) |
| | DXS7127 | TGCACTTAATATCTGGTGATGG (SEQ ID NO 95) | ATTTCTTTCCCTCTGCAACC (SEQ ID NO 96) |
| | DXS7132 | AGCCCATTTTCATAATAAATCC (SEQ ID NO 97) | AATCAGTGCTTTCTGTACTATTGG (SEQ ID NO 98) |
| | DXS8377 | CACTTCATGGCTTACCACAG (SEQ ID NO 99) | GACCTTTGGAAAGCTAGTGT (SEQ ID NO 100) |
| | DXS9893 | TGTCACGTTTACCCTGGAAC (SEQ ID NO 101) | TATTCTTCTATCCAACCAACAGC (SEQ ID NO 102) |
| | DXS9895 | TTGGGTGGGGACACAGAG (SEQ ID NO 103) | CCTGGCTCAAGGAATTACAA (SEQ ID NO 104) |
| | DXS9896 | CCAGCCTGGCTGTTAGAGTA (SEQ ID NO 105) | ATATTCTTATATTCCATATGGCACA (SEQ ID NO 106) |

TABLE 3-continued

Primer Sets for STRs on Chromsomes 13, 18, 21 and X

| Ch. | STR Marker | Primer 1 | Primer 2 |
|---|---|---|---|
| | DXS9902 | TGGAGTCTCTGGGTGAAGAG (SEQ ID NO 107) | CAGGAGTATGGGATCACCAG (SEQ ID NO 108) |
| | DXS998 | CAGCAATTTTTCAAAGGC (SEQ ID NO 109) | AGATCATTCATATAACCTCAAAAGA (SEQ ID NO 110) |

Example 8. Detection of Mutations Related to Fetal Abnormalities

Fetal cells or nuclei can be isolated as describe in the Enrichment section or as described in example 1 and 2. DNA from the fetal cells or isolated nuclei from fetal cells can be obtained using any methods known in the art. The presence of mutations of DNA or RNA from the genes listed in FIG. 4 can then be analyzed. DNA or RNA of any of the genes listed in table 3 can then be amplified according the methods described in the amplification section.

For instance, the genomic DNA from the enriched fetal cells and a maternal control sample can be fragmented, and separated into single strands. The single strands of the target nucleic acids would be bound to beads under conditions that favor each single strand molecule of DNA to bind a different bead. Each bead would then be captured within a droplet of a PCR-reaction-mixture-in-oil-emulsion and PCR amplification occurs within each droplet. The amplification on the bead could results in each bead carrying at least one 10 million copies of the unique single stranded target nucleic acid. The emulsion would be broken, the DNA would be denatured and the beads carrying single-stranded nucleic acids clones would be deposited into a picolitre-sized well for further analysis.

The beads can then be placed into a highly parallel sequencing by synthesis machine which can generate over 400,000 reads (~100 bp per read) in a single 4 hour run. Sequence by synthesis involves inferring the sequence of the template by synthesizing a strand complementary to the target nucleic acid sequence. The identity of each nucleotide would be detected after the incorporation of a labeled nucleotide or nucleotide analog into a growing strand of a complementary nucleic acid sequence in a polymerase reaction. After the successful incorporation of a label nucleotide, a signal would be measured and then nulled and the incorporation process would be repeated until the sequence of the target nucleic acid is identified. The presence of a mutation can then be determined. The enrichment, amplification and sequencing methods described in this example allow for the analysis of rare nucleic acids from fetal cells, even in circumstances where fetal cells are in a mixed sample comprising other maternal cells and even in circumstances where maternal cells dominate the mixture.

Example 9. Quantitative Genotyping Using Molecular Inversion Probes for Trisomy Diagnosis on Fetal Cells Fetal cells or nuclei can be isolated as described in the enrichment section or as described in example 1 and 2. Quantitative genotyping can then be used to detect chromosome copy number changes. The output of the enrichment procedure would be divided into separate wells of a microtiter plate with the number of wells chosen so no more than one cell or genome copy is located per well, and where some wells may have no cell or genome copy at all.

Perform Multiplex PCR and Genotyping Using MIP Technology with Bin Specific Tags:

PCR primer pairs for multiple (40-100) highly polymorphic SNPs can then be added to each well in the microtiter plate. For example, SNPs primers can be designed along chromosomes 13, 18, 21 and X to detect the most frequent aneuploidies, and along control regions of the genome where aneuploidy is not expected. Multiple (~10) SNPs would be designed for each chromosome of interest to allow for non-informative genotypes and to ensure accurate results. PCR primers would be chosen to be multiplexible with other pairs (fairly uniform melting temperature, absence of cross-priming on the human genome, and absence of primer-primer interaction based on sequence analysis). The primers would be designed to generate amplicons 70-100 bp in size to increase the performance of the multiplex PCR. The primers would contain a 22 bp tag on the 5' which is used in the genotyping analysis. A second of round of PCR using nested primers may be performed to ensure optimal performance of the multiplex amplification.

The Molecular Inversion Probe (MIP) technology developed by Affymetrix (Santa Clara, Calif.) can genotype 20,000 SNPs or more in a single reaction. In the typical MIP assay, each SNP would be assigned a 22 bp DNA tag which allows the SNP to be uniquely identified during the highly parallel genotyping assay. In this example, the DNA tags serve two roles: 1) determine the identity of the different SNPs and 2) determine the identity of the well from which the genotype was derived.

The tagged MIP probes would be combined with the amplicons from the initial multiplex single-cell PCR and the genotyping reactions would be performed. The probe/template mix would be divided into 4 tubes each containing a different nucleotide (e.g. G, A, T or C). Following an extension and ligation step, the mixture would be treated with exonuclease to remove all linear molecules and the tags of the surviving circular molecules would be amplified using PCR. The amplified tags form all of the bins would then be pooled and hybridized to a single DNA microarray containing the complementary sequences to each of the 20,000 tags.

Identify Bins with Non-Maternal Alleles (e.g. Fetal Cells):

The first step in the data analysis procedure would be to use the 22 bp tags to sort the 20,000 genotypes into bins which correspond to the individual wells of the original microtiter plates. The second step would be to identify bins contain non-maternal alleles which correspond to wells that contained fetal cells. Determining the number bins with non-maternal alleles relative to the total number of bins would provide an accurate estimate of the number of fnRBCs that were present in the original enriched cell population. When a fetal cell is identified in a given bin, the non-maternal alleles would be detected by 40 independent SNPs which provide an extremely high level of confidence in the result.

Detect Aneuploidy for Chromosomes 13, 18, and 21:

After identifying approximately 10 bins that contain fetal cells, the next step would be to determine the ploidy of chromosomes 13, 18, 21 and X by comparing ratio of maternal to paternal alleles for each of the 10 SNPs on each chromosome. The ratios for the multiple SNPs on each chromosome can be combined (averaged) to increase the confidence of the aneuploidy call for that chromosome. In addition, the information from the approximate 10 independent bins containing fetal cells can also be combined to further increase the confidence of the call.

Example 10. Fetal Diagnosis with CGH

Fetal cells or nuclei can be isolated as described in the enrichment section or as described in example 1 and 2. Comparative genomic hybridization (CGH) can be used to determine copy numbers of genes and chromosomes. DNA extracted from the enriched fetal cells will be hybridized to immobilized reference DNA which can be in the form of bacterial artificial chromosome (BAC) clones, or PCR products, or synthesized DNA oligos representing specific genomic sequence tags. Comparing the strength of hybridization fetal cells and maternal control cells to the immobilized DNA segments gives a copy number ratio between the two samples. To perform CGH effectively starting with small numbers of cells, the DNA from the enriched fetal cells can be amplified according to the methods described in the amplification section.

A ratio-preserving amplification of the DNA would be done to minimize these errors; i.e. this amplification method would be chosen to produce as close as possible the same amplification factor for all target regions of the genome. Appropriate methods would include multiple displacement amplification, the two-stage PCR, and linear amplification methods such as in vitro transcription.

To the extent the amplification errors are random their effect can be reduced by averaging the copy number or copy number ratios determined at different loci over a genomic region in which aneuploidy is suspected. For example, a microarray with 1000 oligo probes per chromosome could provide a chromosome copy number with error bars ~sqrt (1000) times smaller than those from the determination based on a single probe. It is also important to perform the probe averaging over the specific genomic region(s) suspected for aneuploidy. For example, a common known segmental aneuploidy would be tested for by averaging the probe data only over that known chromosome region rather than the entire chromosome. Segmental aneuploidies can be caused by a chromosomal rearrangement, such as a deletion, duplication or translocation event. Random errors could be reduced by a very large factor using DNA microarrays such as Affymetrix arrays that could have a million or more probes per chromosome.

In practice other biases will dominate when the random amplification errors have been averaged down to a certain level, and these biases in the CGH experimental technique must be carefully controlled. For example, when the two biological samples being compared are hybridized to the same array, it is helpful to repeat the experiment with the two different labels reversed and to average the two results—this technique of reducing the dye bias is called a 'fluor reversed pair'. To some extent the use of long 'clone' segments, such as BAC clones, as the immobilized probes provides an analog averaging of these kinds of errors; however, a larger number of shorter oligo probes should be superior because errors associated with the creation of the probe features are better averaged out.

Differences in amplification and hybridization efficiency from sequence region to sequence region may be systematically related to DNA sequence. These differences can be minimized by constraining the choices of probes so that they have similar melting temperatures and avoid sequences that tend to produce secondary structure. Also, although these effects are not truly 'random', they will be averaged out by averaging the results from a large number of array probes. However, these effects may result in a systematic tendency for certain regions or chromosomes to have slightly larger signals than others, after probe averaging, which may mimic aneuploidy. When these particular biases are in common between the two samples being compared, they divide out if the results are normalized so that control genomic regions believed to have the same copy number in both samples yield a unity ratio.

After performing CGH analysis trisomy can be diagnosed by comparing the strength of hybridization fetal cells and maternal control cells to the immobilized DNA segments which would give a copy number ratio between the two samples.

In one method, DNA samples will be obtained from the genomic DNA from enriched fetal cells and a maternal control sample. These samples are digested with the Alu I restriction enzyme (Promega, catalog # R6281) in order to introduce nicks into the genomic DNA (e.g. 10 minutes at 55° C. followed by immediately cooling to ~32° C.). The partially digested sample is then boiled and transferred to ice. This is followed by Terminal Deoxynucleotidyl (TdT) tailing with dTTP at 37° C. for 30 minutes. The sample is boiled again after completion of the tailing reaction, followed by a ligation reaction wherein capture sequences, complementary to the poly T tail and labeled with a fluorescent dye, such as Cy3/green and Cy5/red, are ligated onto the strands. If fetal DNA is labeled with Cy3 then the maternal DNA is labeled with FITC, or vice versa. The ligation reaction is allowed to proceed for 30 minutes at room temperature before it is stopped by the addition of 0.5M EDTA. Labeled DNAs are then purified from the reaction components using a cleanup kit, such as the Zymo DNA Clean and Concentration kit. Purified tagged DNAs are resuspended in a mixture containing 2× hybridization buffer, which contains LNA dT blocker, calf thymus DNA, and nuclease free water. The mixture is vortexed at 14,000 RPM for one minute after the tagged DNA is added, then it is incubated at 95° C.–100° C. for 10 minutes. The tagged DNA hybridization mixture containing both labeled DNAs is then incubated on a glass hybridization slide, which has been prepared with human bacterial artificial chromsomes (BAC), such as the 32K array set. BAC clones covering at least 98% of the human genome are available from BACPAC Resources, Oakland Calif.

The slide is then incubated overnight (~16 hours) in a dark humidified chamber at 52° C. The slide is then washed using multiple post hybridization washed. The BAC microarray is then imaged using an epifluorescence microscope and a CCD camera interfaced to a computer. Analysis of the microarray images is performed using the GenePix Pro 4.0 software (Axon Instruments, Foster City Calif.). For each spot the median pixel intensity minus the median local background for both dyes is used to obtain a test over reference gene copy number ratio. Data normalization is performed per array sub-grid using lowest curve fitting with a smoothing factor of 0.33. To identify imbalances the MATLAB toolbox CGH plotter is applied, using moving mean average over three clones and limits of log 2>o.2. Classification as gain or loss is based on (1) identification as such by the CGH plotter and (2) visual inspection of the log 2 ratios. In general, log 2 ratios >0.5 in at least four adjacent clones will be considered to be deviating. Ratios of 0.5-1.0 will be classified as duplications/hemizygous deletions; whereas, ratios >1 will be classified as amplifications/homozygous deletions. All normalizations and analyses are carried out using analysis software, such as the BioArray Software Environment database. Regions of the genome that are either gained or lost in the fetal cells are indicated by the fluorescence intensity ratio profiles. Thus, in a single hybridization it is possible to screen the vast majority of chromosomal sites that may contain genes that are either deleted or amplified in the fetal cells The sensitivity of CGH in detecting gains and losses of DNA sequences is approximately 0.2-20 Mb. For example, a loss of a 200 kb region should be detectable under optimal hybridization conditions. Prior to CGH hybridization, DNA can be universally amplified using degenerate oligonucleotide-primed PCR (DOP-PCR), which allows the analysis of; for example, rare fetal cell samples. The latter technique requires a PCR pre-amplification step.

Primers used for DOP-PCR have defined sequences at the 5' end and at the 3' end, but have a random hexamer sequence between the two defined ends. The random hexamer sequence displays all possible combinations of the natural nucleotides A, G, C, and T. DOP-PCR primers are annealed at low stringency to the denatured template DNA and hybridize statistically to primer binding sites. The distance between primer binding sites can be controlled by the length of the defined sequence at the 3' end and the stringency of the annealing conditions. The first five cycles of the DOP-PCR thermal cycle consist of low stringency annealing, followed by a slow temperature increase to the elongation temperature, and primer elongation. The next thirty-five cycles use a more stringent (higher) annealing temperature. Under the more stringent conditions the material which was generated in the first five cycles is amplified preferentially, since the complete primer sequence created at the amplicon termini is required for annealing. DOP-PCR amplification ideally results in a smear of DNA fragments that are visible on an agarose gel stained with ethidium bromide. These fragments can be directly labelled by ligating capture sequences, complementary to the primer sequences and labeled with a fluorescent dye, such as Cy3/green and Cy5/red. Alternatively the primers can be labelled with a florescent dye, in a manner that minimizes steric hindrance, prior to the amplification step.

Example 11. Isolation of Epithelial Cells from Blood

Figure 18:
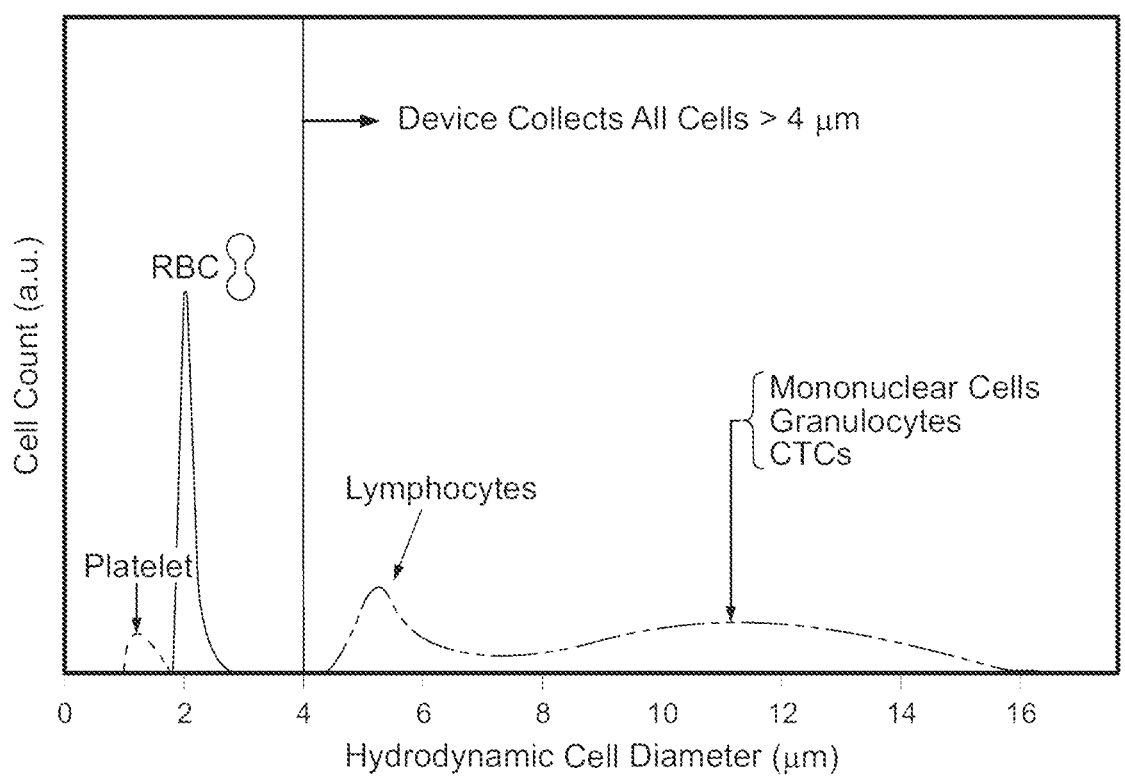
FIG. 18 illustrates performance of cell separation module.
Figure 19:
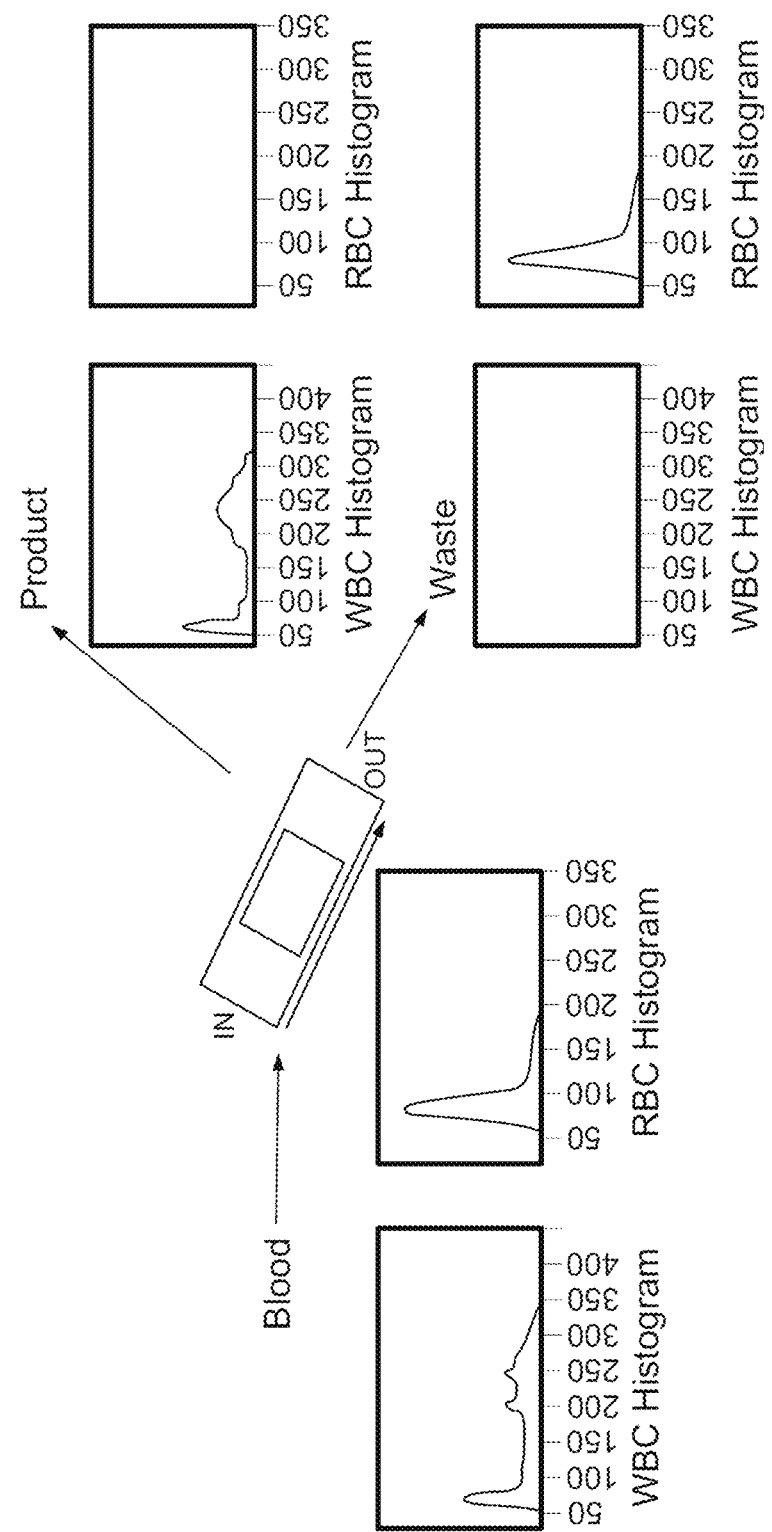
FIG. 19 illustrates histograms representative of cell fractions resulting from cell separation module described herein.
Figure 20:
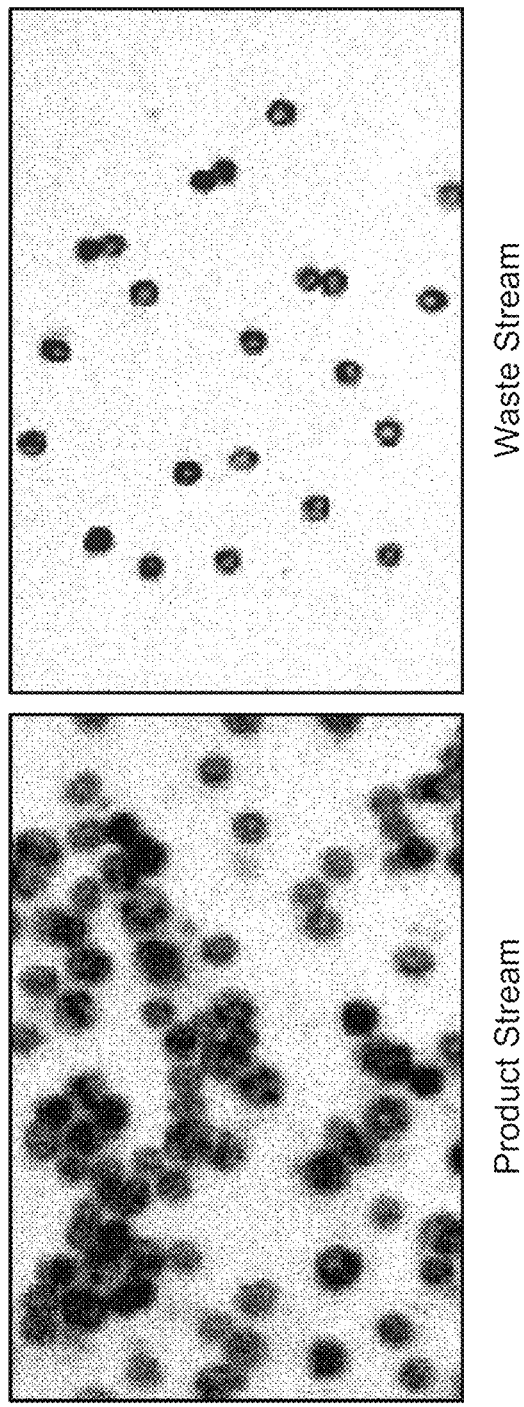
FIG. 20 illustrates cytology of products from cell separation module.

Microfluidic devices of the invention were designed by computer-aided design (CAD) and microfabricated by photolithography. A two-step process was developed in which a blood sample is first debulked to remove the large population of small cells, and then the rare target epithelial cells target cells are recovered by immunoaffinity capture. The devices were defined by photolithography and etched into a silicon substrate based on the CAD-generated design. The cell enrichment module, which is approximately the size of a standard microscope slide, contains 14 parallel sample processing sections and associated sample handling channels that connect to common sample and buffer inlets and product and waste outlets. Each section contains an array of microfabricated obstacles that is optimized to enrich the target cell type by hydrodynamic size via displacement of the larger cells into the product stream. In this example, the microchip was designed to separate red blood cells (RBCs) and platelets from the larger leukocytes and CTCs. Enriched populations of target cells were recovered from whole blood passed through the device. Performance of the cell enrichment microchip was evaluated by separating RBCs and platelets from white blood cells (WBCs) in normal whole blood (FIG. 18). In cancer patients, CTCs are found in the larger WBC fraction. Blood was minimally diluted (30%), and a 6 ml sample was processed at a flow rate of up to 6 ml/hr. The product and waste stream were evaluated in a Coulter Model "$A^C$-T diff" clinical blood analyzer, which automatically distinguishes, sizes, and counts different blood cell populations. The enrichment chip achieved separation of RBCs from WBCs, in which the WBC fraction had >99% retention of nucleated cells, >99% depletion of RBCs, and >97% depletion of platelets. Representative histograms of these cell fractions are shown in FIG. 19. Routine cytology confirmed the high degree of enrichment of the WBC and RBC fractions (FIG. 20).

Next, epithelial cells were recovered by affinity capture in a microfluidic module that is functionalized with immobilized antibody. A capture module with a single chamber containing a regular array of antibody-coated microfabricated obstacles was designed. These obstacles are disposed to maximize cell capture by increasing the capture area approximately four-fold, and by slowing the flow of cells under laminar flow adjacent to the obstacles to increase the contact time between the cells and the immobilized antibody. The capture modules may be operated under conditions of relatively high flow rate but low shear to protect cells against damage. The surface of the capture module was functionalized by sequential treatment with 10% silane, 0.5% gluteraldehyde, and avidin, followed by biotinylated anti-EpCAM. Active sites were blocked with 3% bovine serum albumin in PBS, quenched with dilute Tris HCl, and stabilized with dilute L-histidine. Modules were washed in PBS after each stage and finally dried and stored at room temperature. Capture performance was measured with the human advanced lung cancer cell line NCI-H1650 (ATCC Number CRL-5883). This cell line has a heterozygous 15 bp in-frame deletion in exon 19 of EGFR that renders it susceptible to gefitinib. Cells from confluent cultures were harvested with trypsin, stained with the vital dye Cell Tracker Orange (CMRA reagent, Molecular Probes, Eugene, Oreg.), resuspended in fresh whole blood, and fractionated in the microfluidic chip at various flow rates. In these initial feasibility experiments, cell suspensions were processed directly in the capture modules without prior fractionation in the cell enrichment module to debulk the red blood cells; hence, the sample stream contained normal blood red cells and leukocytes as well as tumor cells. After the cells were processed in the capture module, the device was washed with buffer at a higher flow rate (3 ml/hr) to remove the nonspecifically bound cells. The adhesive top was removed and the adherent cells were fixed on the chip with paraformaldehyde and observed by fluorescence microscopy. Cell recovery was calculated from hemacytometer counts; representative capture results are shown in Table 4. Initial yields in reconstitution studies with unfractionated blood were greater than 60% with less than 5% of non-specific binding.

TABLE 4

| Run number | Avg flow rate | Length of run | No. cells processed | No. cells captured | Yield |
|---|---|---|---|---|---|
| 1 | 3.0 | 1 hr | 150,000 | 38.012 | 25% |
| 2 | 1.5 | 2 hr | 150,000 | 30.000/ml | 60% |
| 3 | 1.08 | 2 hr | 108,000 | 66.661 | 64% |
| 4 | 1.21 | 2 hr | 121,000 | 75.491 | 62% |

Next, NCI-H1650 cells that were spiked into whole blood and recovered by size fractionation and affinity capture as described above were successfully analyzed in situ. In a trial run to distinguish epithelial cells from leukocytes, 0.5 ml of a stock solution of fluorescein-labeled CD45 pan-leukocyte monoclonal antibody were passed into the capture module and incubated at room temperature for 30 minutes. The module was washed with buffer to remove unbound antibody, and the cells were fixed on the chip with 1% paraformaldehyde and observed by fluorescence microscopy. As shown in FIG. 21 the epithelial cells were bound to the obstacles and floor of the capture module. Background staining of the flow passages with CD45 pan-leukocyte antibody is visible, as are several stained leukocytes, apparently because of a low level of non-specific capture.

Example 12. Method for Detection of EGFR Mutations

Figure 22:
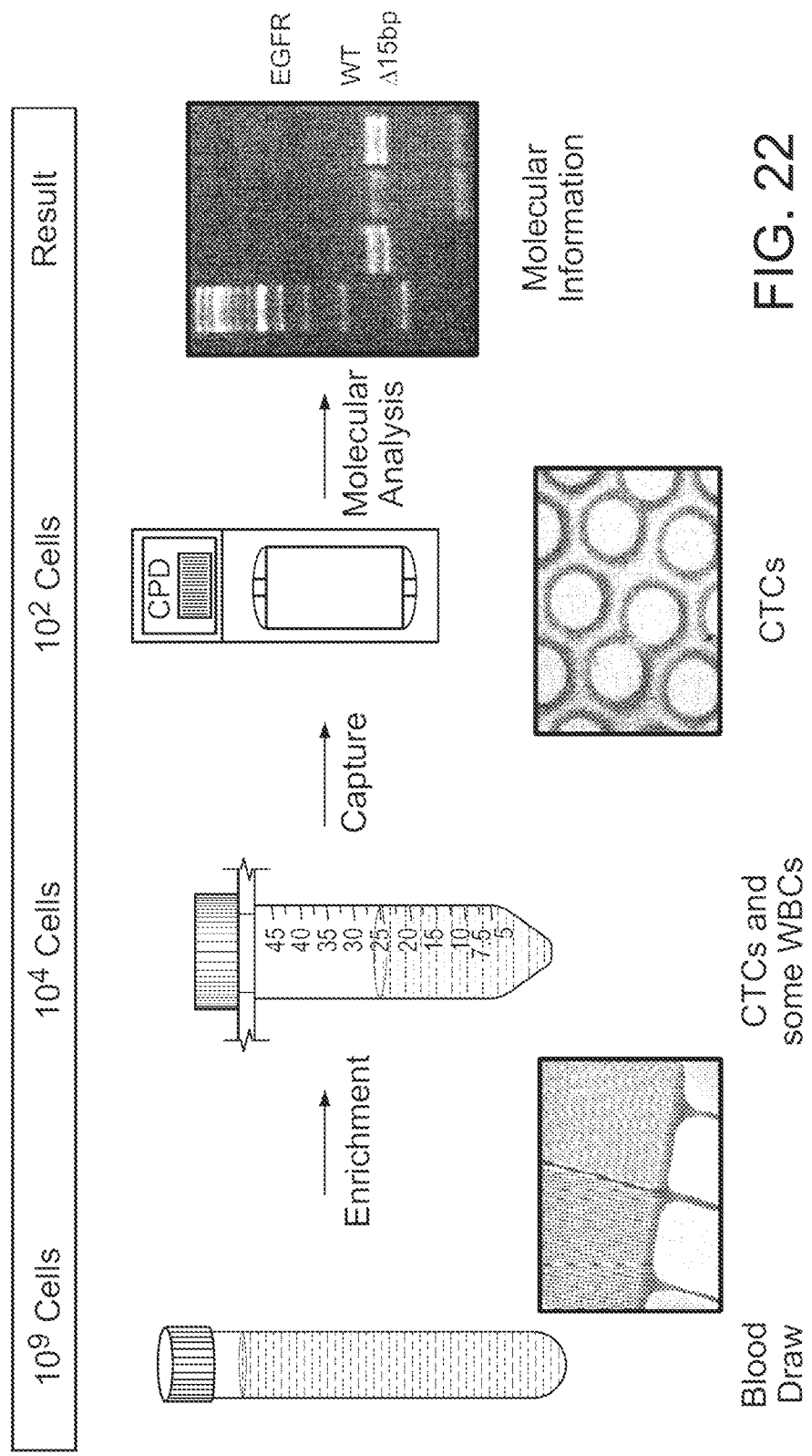
FIG. 22 illustrates a process for analyzing enriched epithelial cells for EGFR mutations.

A blood sample from a cancer patient is processed and analyzed using the devices and methods of the invention, e.g., those of Example 11, resulting in an enriched sample of epithelial cells containing CTCs. This sample is then analyzed to identify potential EGFR mutations. The method permits both identification of known, clinically relevant EGFR mutations as well as discovery of novel mutations. An overview of this process is shown in FIG. 22.

Below is an outline of the strategy for detection and confirmation of EGFR mutations:
1) Sequence CTC EGFR mRNA
 a) Purify CTCs from blood sample;
 b) Purify total RNA from CTCs;
 c) Convert RNA to cDNA using reverse transcriptase;
 d) Use resultant cDNA to perform first and second PCR reactions for generating sequencing templates; and
 e) Purify the nested PCR amplicon and use as a sequencing template to sequence EGFR exons 18-21.
2) Confirm RNA sequence using CTC genomic DNA
 a) Purify CTCs from blood sample;
 b) Purify genomic DNA (gDNA) from CTCs;
 c) Amplify exons 18, 19, 20, and/or 21 via PCR reactions; and
 d) Use the resulting PCR amplicon(s) in real-time quantitative allele-specific PCR reactions in order to confirm the sequence of mutations discovered via RNA sequencing.

Figure 23:
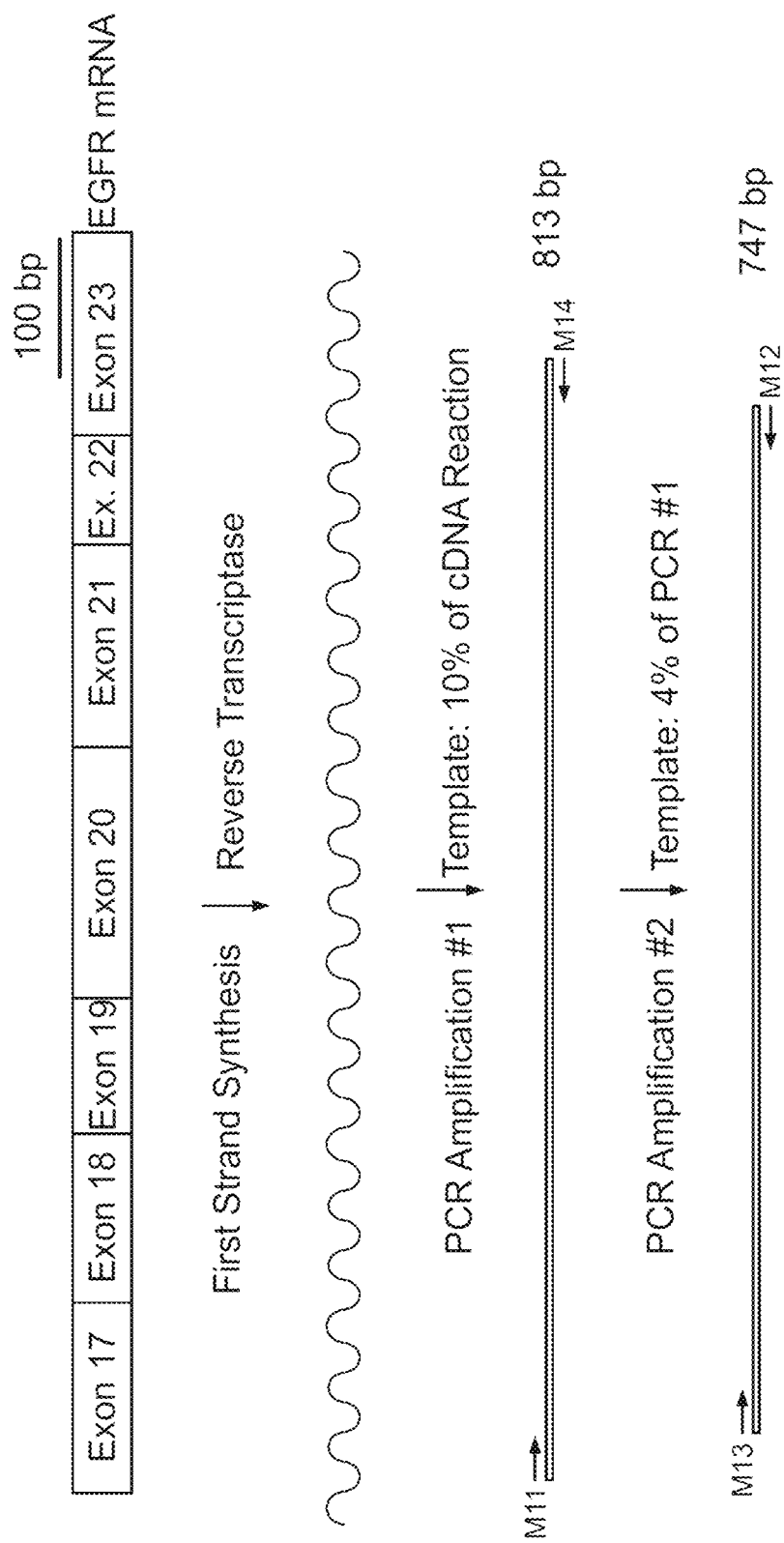
FIG. 23 illustrates a method for generating sequences templates for regions of interest.

Further details for each step outlined above are as follows:
1) Sequence CTC EGFR mRNA
 a) Purify CTCs from blood sample. CTCs are isolated using any of the size-based enrichment and/or affinity purification devices of the invention.
 b) Purify total RNA from CTCs. Total RNA is then purified from isolated CTC populations using, e.g., the Qiagen Micro RNeasy kit, or a similar total RNA purification protocol from another manufacturer, alternatively, standard RNA purification protocols such as guanidium isothiocyanate homogenization followed by phenol/chloroform extraction and ethanol precipitation may be used.

c) Convert RNA to cDNA using reverse transcriptase. cDNA reactions are carried out based on the protocols of the supplier of reverse transcriptase. Typically, the amount of input RNA into the cDNA reactions is in the range of 10 picograms (pg) to 2 micrograms (ptg) total RNA. First-strand DNA synthesis is carried out by hybridizing random 7mer DNA primers, or oligo-dT primers, or gene-specific primers, to RNA templates at 65° C. followed by snap-chilling on ice. cDNA synthesis is initiated by the addition of iScript Reverse Transcriptase (BioRad) or SuperScript Reverse Transcriptase (Invitrogen) or a reverse transcriptase from another commercial vendor along with the appropriate enzyme reaction buffer. For iScript, reverse transcriptase reactions are carried out at 42° C. for 30-45 minutes, followed by enzyme inactivation for 5 minutes at 85° C. cDNA is stored at −20° C. until use or used immediately in PCR reactions. Typically, cDNA reactions are carried out in a final volume of 20 µl, and 10% (2 µl) of the resultant cDNA is used in subsequent PCR reactions.

d) Use resultant cDNA to perform fwst and second PCR reactions for generating sequencing templates. cDN A from the reverse transcriptase reactions is mixed with DNA primers specific for the region of interest (FIG. 23). See Table 5 for sets of primers that may be used for amplification of exons 18-21. In Table 5, primer set M13(+)/M12(−) is internal to primer set M11(+)/M14(−). Thus primers M13(+) and M12(−) may be used in the nested round of amplification, if primers M11(+) and M14(−) were used in the first round of expansion. Similarly, primer set M11(+)/M14(−) is internal to primer set M15(+)/M16(−), and primer set M23(+)/M24(−) is internal to primer set M21(+)/M22(−). Hot Start PCR reactions are performed using Qiagen Hot-Star Taq Polymerase kit, or Applied Biosystems HotStart TaqMan polymerase, or other Hot Start thermostable polymerase, or without a hot start using Promega GoTaq Green Taq Polymerase master mix, TaqMan DNA polymerase, or other thermostable DNA polymerase. Typically, reaction volumes are 50 µl, nucleotide triphosphates are present at a final concentration of 200 µM for each nucleotide, $MgCl_2$ is present at a final concentration of 1-4 mM, and oligo primers are at a final concentration of 0.5 µM. Hot start protocols begin with a 10-15 minute incubation at 95° C., followed by 40 cycles of 94° C. for one minute (denaturation), 52° C. for one minute (annealing), and 72° C. for one minute (extension). A 10 minute terminal extension at 72° C. is performed before samples are stored at 4° C. until they are either used as template in the second (nested) round of PCRs, or purified using QiaQuick Spin Columns (Qiagen) prior to sequencing. If a hot-start protocol is not used, the initial incubation at 95° C. is omitted. If a PCR product is to be used in a second round of PCRs, 2 µl (4%) of the initial PCR product is used as template in the second round reactions, and the identical reagent concentrations and cycling parameters are used.

TABLE 5

Primer Sets for expanding EGFR mRNA around Exons 18-21

| Name | SEQ ID NO | Sequence (5' to 3') | cDNA Coordinates | Amplicon Size |
|---|---|---|---|---|
| NXK-M11(+) | 111 | TTGCTGCTGGTGGTGGC | (+) 1966-1982 | 813 |
| NXK-M14(-) | 112 | CAGGGATTCCGTCATATGGC | (-) 2778-2759 | |
| NXK-M13(+) | 113 | GATCGGCCTCTTCATGCG | (+) 1989-2006 | 747 |
| NXK M12(-) | 114 | GATCCAAAGGTCATCAACTCCC | (-) 2735-2714 | |
| NXK-M15(+) | 115 | GCTGTCCAACGAATGGGC | (+) 1904-1921 | 894 |
| NXK-M16(-) | 116 | GGCGTTCTCCTTTCTCCAGG | (-) 2797-2778 | |
| NXK-M21(+) | 117 | ATGCACTGGGCCAGGTCTT | (+) 1881-1899 | 944 |
| NXK-M22(-) | 118 | CGATGGTACATATGGGTGGCT | (-) 2824-2804 | |
| NXK-M23(+) | 119 | AGGCTGTCCAACGAATGGG | (+) 1902-1920 | 904 |
| NXK-M24(-) | 120 | CTGAGGGAGGCGTTCTCCT | (-) 2805-2787 | | e) Purify the nested PCR amplicon and use as a sequencing template to sequence EGFR exons 18-21. Sequencing is performed by ABI automated fluorescent sequencing machines and fluorescence-labeled DNA sequencing ladders generated via Sanger-style sequencing reactions using fluorescent dideoxynucleotide mixtures. PCR products are purified using Qiagen QuickSpin columns, the Agencourt AMPure PCR Purification System, or PCR product purification kits obtained from other vendors. After PCR products are purified, the nucleotide concentration and purity is determined with a Nanodrop 7000 spectrophotometer, and the PCR product concentration is brought to a concentration of 25 ng/ld. As a quality control measure, only PCR products that have a UV-light absorbance ratio ($A_{260}/A_{280}$) greater than 1.8 are used for sequencing. Sequencing primers are brought to a concentration of 3.2 pmol/μl.

2) Confirm RNA sequence using CTC genomic DNA a) Purify CTCs from blood sample. As above, CTCs are isolated using any of the size-based enrichment and/or affinity purification devices of the invention.

b) Purify genomic DNA (gDNA) from CTCs. Genomic DNA is purified using the Qiagen DNeasy Mini kit, the Invitrogen ChargeSwitch gDNA kit, or another commercial kit, or via the following protocol:

1. Cell pellets are either lysed fresh or stored at −80° C. and are thawed immediately before lysis.
2. Add 500 μl 50 mM Tris pH 7.9/100 mM EDTA/0.5% SDS (TES buffer).
3. Add 12.5 μl Proteinase K (IB15406, 20 mg/ml), generating a final [ProtK]=0.5 mg/ml.
4. Incubate at 55° C. overnight in rotating incubator.
5. Add 20 μl of RNase cocktail (500 U/ml RNase A +20,000 U/ml RNase TI, Ambion #2288) and incubate four hours at 37° C.
6. Extract with Phenol (Kodak, Tris pH 8 equilibrated), shake to mix, spin 5 min. in tabletop centrifuge.
7. Transfer aqueous phase to fresh tube.
8. Extract with Phenol/Chloroform/Isoamyl alcohol (EMD, 25:24:1 ratio, Tris pH 8 equilibrated), shake to mix, spin five minutes in tabletop centrifuge.
9. Add 50 μl 3M NaOAc pH=6.
10. Add 500 μl EtOH.
11. Shake to mix. Strings of precipitated DNA may be visible. If anticipated DNA concentration is very low, add carrier nucleotide (usually yeast tRNA).
12. Spin one minute at max speed in tabletop centrifuge.
13. Remove supernatant.
14. Add 500 μl 70% EtOH, Room Temperature (RT)
15. Shake to mix.
16. Spin one minute at max speed in tabletop centrifuge.
17. Air dry 10-20 minutes before adding TE.
18. Resuspend in 400 μl TE. Incubate at 65° C. for 10 minutes, then leave at RT overnight before quantitation on Nanodrop.

c) Amplify exons 18, 19, 20, and/or 21 via PCR reactions. Hot start nested PCR amplification is carried out as described above in step Id, except that there is no nested round of amplification. The initial PCR step may be stopped during the log phase in order to minimize possible loss of allele-specific information during amplification. The primer sets used for expansion of EGFR exons 18-21 are listed in Table 6 (see also Paez et al., Science 304:1497-1500 (Supplementary Material) (2004)).

TABLE 6

Primer sets for expanding EGFR genomic DNA

| Name | SEQ ID NO | Sequence (5' to 3") | Exon | Amplicon Size |
|---|---|---|---|---|
| NXK-ex18.1(+) | 121 | TCAGAGCCTGTGTTTCTACCAA | 18 | 534 |
| NXK-ex18.2(-) | 122 | TGGTCTCACAGGACCACTGATT | 18 | |
| NXK-ex18.3(+) | 123 | TCCAAATGAGCTGGCAAGTG | 18 | 397 |
| NXK-ex18.4(-) | 124 | TCCCAAACACTCAGTGAAACAAA | 18 | |
| NXK-ex19.1(+) | 125 | AAATAATCAGTGTGATTCGTGGAG | 19 | 495 |
| NXK-ex19.2(-) | 126 | GAGGCCAGTGCTGTCTCTAAGG | 19 | |

TABLE 6-continued

Primer sets for expanding EGFR genomic DNA

Figure 24:
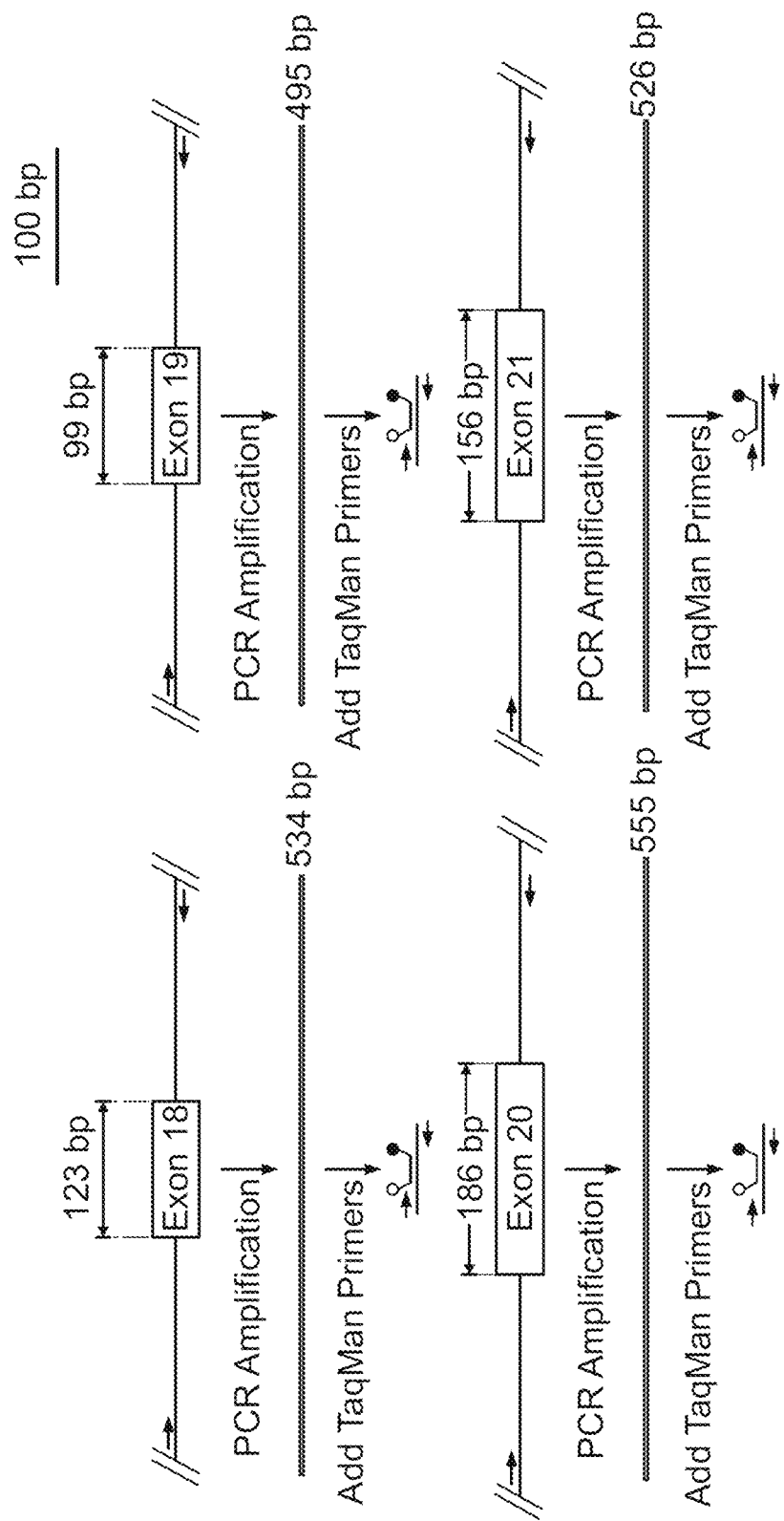
FIG. 24 illustrates exemplary allele specific reactions showing mutations.

| Name | SEQ ID NO | Sequence (5' to 3") | Exon | Amplicon Size |
|---|---|---|---|---|
| NXK-ex19.3(+) | 127 | GTGCATCGCTGGTAACATCC | 19 | 298 |
| NXK-ext9.4(-) | 128 | TGTGGAGATGAGCAGGGTCT | 19 | |
| NXK-ex20.1(+) | 129 | ACTTCACAGCCCTGCGTAAAC | 20 | 555 |
| NXK-ex20.2(-) | 130 | ATGGGACAGGCACTGATTTGT | 20 | |
| NXK-ex20.3(+) | 131 | ATCGCATTCATGCGTCTTCA | 20 | 379 |
| NXK-ex20.4(-) | 132 | ATCCCCATGGCAAACTCTTG | 20 | |
| NXK-ex21.1(+) | 133 | GCAGCGGGTTACATCTTCTTTC | 21 | 526 |
| NXK-ex21.2(-) | 134 | CAGCTCTGGCTCACACTACCAG | 21 | |
| NXK-ex21.3(+) | 135 | GCAGCGGGTTACATCTTCTTTC | 21 | 349 |
| NXK-ex21.4(-) | 136 | CATCCTCCCCTGCATGTGT | 21 | | d) Use the resulting PCR amplicon(s) in real-time quantitative allele-specific PCR reactions in order to confirm the sequence of mutations discovered via RNA sequencing. An aliquot of the PCR amplicons is used as template in a multiplexed allele-specific quantitative PCR reaction using TaqMan PCR 5' Nuclease assays with an Applied Biosystems model 7500 Real Time PCR machine (FIG. 24). This round of PCR amplifies subregions of the initial PCR product specific to each mutation of interest. Given the very high sensitivity of Real Time PCR, it is possible to obtain complete information on the mutation status of the EGFR gene even if as few as 10 CTCs are isolated. Real Time PCR provides quantification of allelic sequences over 8 logs of input DNA concentrations; thus, even heterozygous mutations in impure populations are easily detected using this method.

Probe and primer sets are designed for all known mutations that affect gefitinib responsiveness in NSCLC patients, including over 40 such somatic mutations, including point mutations, deletions, and insertions, that have been reported in the medical literature. For illustrative purposes, examples of primer and probe sets for five of the point mutations are listed in Table 7. In general, oligonucleotides may be designed using the primer optimization software program Primer Express (Applied Biosystems), with hybridization conditions optimized to distinguish the wild type EGFR DNA sequence from mutant alleles. EGFR genomic DNA amplified from lung cancer cell lines that are known to carry EGFR mutations, such as H358 (wild type), H1650 (15-bp deletion, Δ2235-2249), and H1975 (two point mutations, 2369 C→T, 2573 T→G), is used to optimize the allele-specific Real Time PCR reactions. Using the TaqMan 5' Nuclease assay, allele-specific labeled probes specific for wild type sequence or for known EGFR mutations are developed. The oligonucleotides are designed to have melting temperatures that easily distinguish a match from a mismatch, and the Real Time PCR conditions are optimized to distinguish wild type and mutant alleles. All Real Time PCR reactions are carried out in triplicate.

Initially, labeled probes containing wild type sequence are multiplexed in the same reaciion with a single mutant probe. Expressing the results as a ratio of one mutant allele sequence versus wild type sequence may identify samples containing or lacking a given mutation. After conditions are optimized for a given probe set, it is then possible to multiplex probes for all of the mutant alleles within a given exon within the same Real Time PCR assay, increasing the ease of use of this analytical tool in clinical settings.

Figure 25:
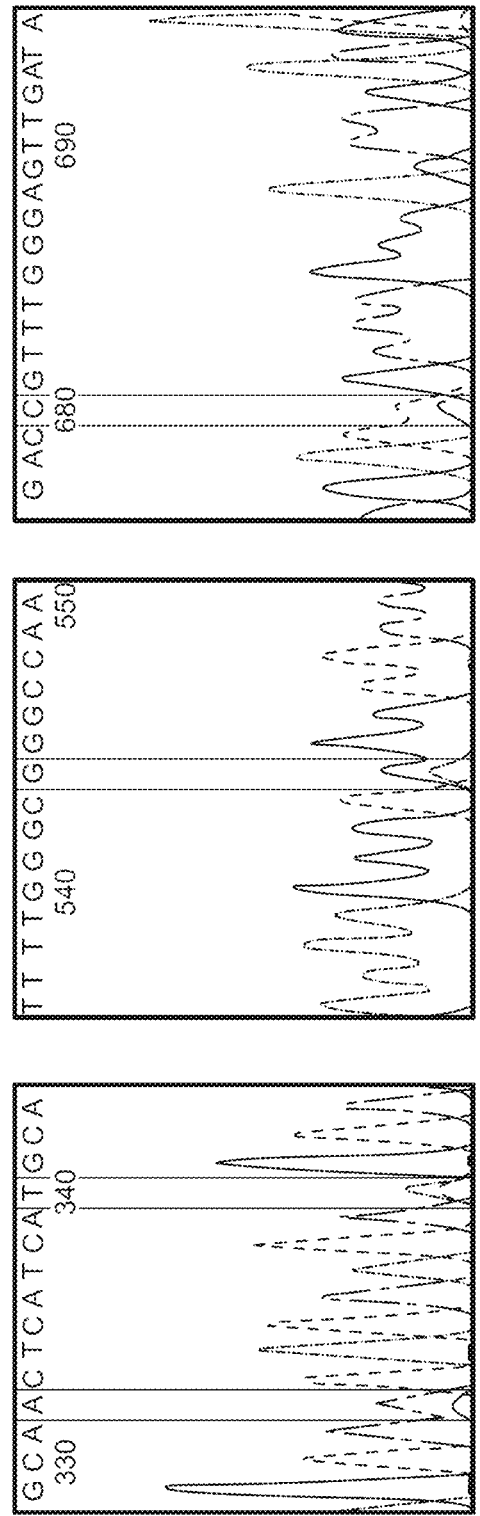
FIG. 25 illustrates exemplary signals from an ABT.

A unique probe is designed for each wild type allele and mutant allele sequence. Wild-type sequences are marked with the fluorescent dye VIC at the 5' end, and mutant sequences with the fluorophore FAM. A fluorescence quencher and Minor Groove Binding moiety are attached to the 3' ends of the probes. ROX is used as a passive reference dye for normalization purposes. A standard curve is generated for wild type sequences and is used for relative quantitation. Precise quantitation of mutant signal is not required, as the input cell population is of unknown, and varying, purity. The assay is set up as described by ABI product literature, and the presence of a mutation is confirmed when the signal from a mutant allele probe rises above the background level of fluorescence (FIG. 25), and this threshold cycle gives the relative frequency of the mutant allele in the input sample.

TABLE 7

Probes and Primers for Allele-Specific qPCR

| Name | SEQ ID NO | Sequence (5' to 3', mutated position in bold) | cDNA Coordinates | Description | Mutation |
|---|---|---|---|---|---|
| NXK-M01 | 137 | CCGCAGCATGTCAAGATCAC | (+)2542-2561 | (+) primer | L858R |
| NXK-M02 | 138 | TCCTTCTGCATGGTATTCTTTCTCT | (-) 2619-2595 | (-) primer | |
| Pwt-L858R | 139 | VIC-TTTGGGCTGGCCAA-MGB | (+) 2566-2579 | WT allele probe | |

TABLE 7-continued

Probes and Primers for Allele-Specific qPCR

| Name | SEQ ID NO | Sequence (5' to 3', mutated position in bold) | cDNA Coordinates | Description | Mutation |
|---|---|---|---|---|---|
| Pmut-L858R | 140 | FAM-TTTTGGGCGGGCCA-MGB | (+2566-2579 | Mutant allele probe | |
| NXK-M03 | 141 | ATGGCCAGCGTGGACAA | (+) 2296-2312 | (+) primer | T790M |
| NXK-M04 | 142 | AGCAGGTACTGGGAGCCAATATT | (-) 2444-2422 | (-) primer | |
| Pwt-T790M | 143 | VIC-ATGAGCTGCGTGATGA-MGB | (-) 2378-2363 | WT allele probe | |
| Pmut-T790M | 144 | FAM-ATGAGCTGCATGATGA-MGB | (-) 2378-2363 | Mutant allele probe | |
| NXK-M05 | 145 | GCCTCTTACACCCAGTGGAGAA | (+) 2070-2091 | (+) primer | G719S, C |
| NXK-M06 | 146 | TTCTGGGATCCAGAGTCCCTTA | (-) 2202-2181 | (-) primer | |
| Pwt-G719SC | 147 | VIC-ACCGGAGCCCAGCA-MGB | (-) 2163-2150 | WT allele probe | |
| Pmut-G719S | 148 | FAM-ACCGGAGCTCAGCA-MGB | (-) 2163-2150 | Mutant allele probe | |
| Pmut-G719C | 149 | FAM-ACCGGAGCAGAGCA-MGB | (-) 2163-2150 | Mutant allele probe | |
| NXK-M09 | 150 | TCGCAAAGGGCATGAACTACT | (+) 2462-2482 | (+) primer | H835L |
| NXK-M10 | 151 | ATCTTGACATGCTGCGGTGTT | (-) 2558-2538 | (-) primer | |
| Pwt-H835L | 152 | VIC-TTGGTGCACCGCGA-MGB | (+) 2498-2511 | WT allele probe | |
| Pmut-H835L | 153 | FAM-TGGTGCTCCGCGAC-MGB | (+) 2498-2511 | Mutant allele probe | |

Example 13: Absence of EGFR Expression in Leukocytes

The protocol of Example 10 would be most useful if EGFR were expressed in target cancer cells but not in background leukocytes. To test whether EGFR mRNA is present in leukocytes, several PCR experiments were performed. Four sets of primers, shown in Table 8, were designed to amplify four corresponding genes:

1) BCKDK (branched-chain a-ketoacid dehydrogenase complex kinase)—a "housekeeping" gene expressed in all types of cells, a positive control for both leukocytes and tumor cells;
2) CD45—specifically expressed in leukocytes, a positive control for leukocytes and a negative control for tumor cells;
3) EpCaM—specifically expressed in epithelial cells, a negative control for leukocytes and a positive control for tumor cells; and
4) EGFR—the target mRNA to be examined.

TABLE 8

| Name | SEQ ID NO | Sequence (5' to 3') | Description | Amplicon Size |
|---|---|---|---|---|
| BCKD_1 | 154 | AGTCAGGACCCATGCACGG | BCKDK (+) primer | 273 |
| BCKD_2 | 155 | ACCCAAGATGCAGCAGTGTG | BCKDK (-) primer | |
| CD_1 | 156 | GATGTCCTCCTTGTTCTACTC | CD45 (+) primer | 263 |
| CD_2 | 157 | TACAGGGAATAATCGAGCATGC | CD45 (-) primer | |
| EpCAM_1 | 158 | GAAGGGAAATAGCAAATGGACA | EpCAM (+) primer | 222 |
| EpCAM_2 | 159 | CGATGGAGTCCAAGTTCTGG | EpCAM (-) primer | |
| EGFR_1 | 160 | AGCACTTACAGCTCTGGCCA | EGFR (+) primer | 371 |
| EGER_2 | 161 | GACTGAACATAACTGTAGGCTG | EGFR (-) primer | |

Figure 26A:
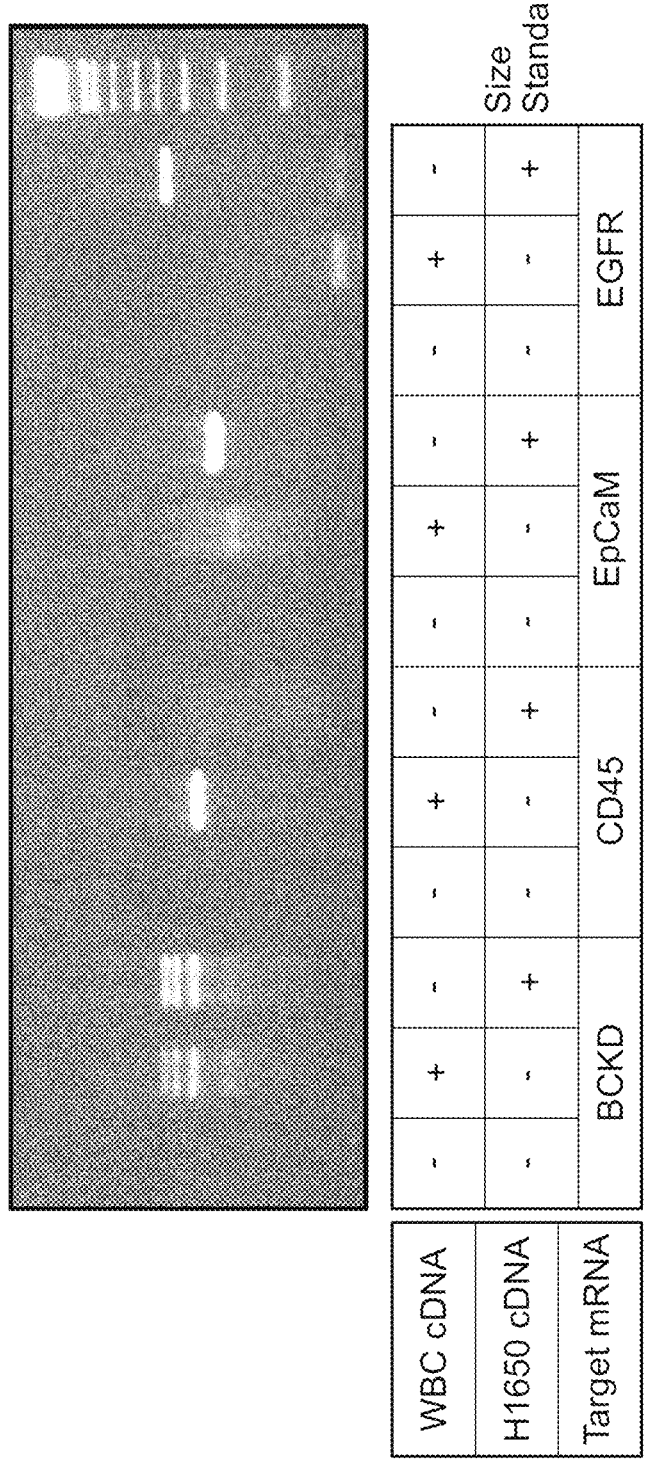
FIG. 26A illustrates BCKDK expressed in leukocytes and H1650 cells.
Figure 26B:
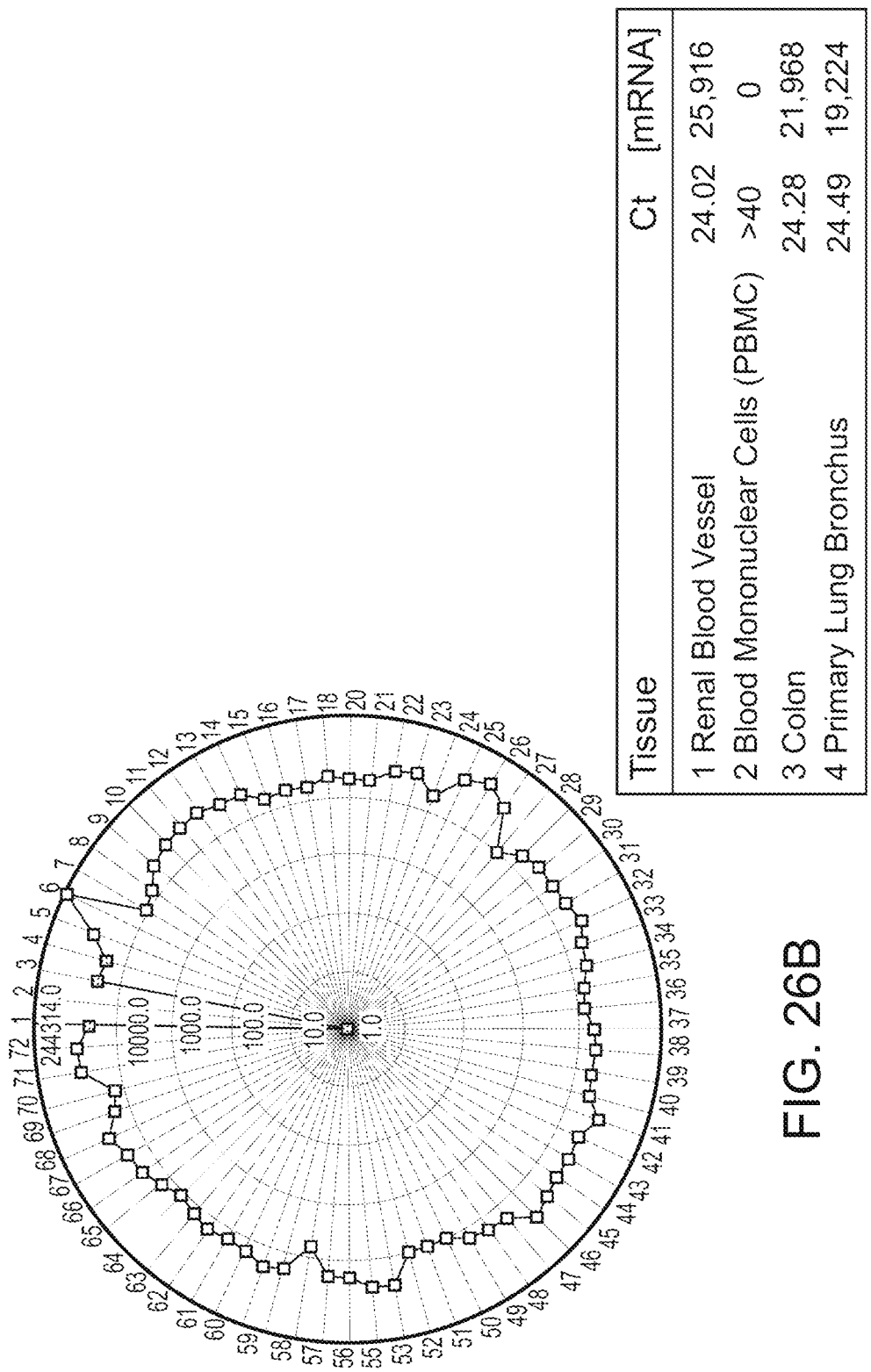
FIG. 26B illustrates EGFR expression profile.

Total RNAs of approximately 9×10$^6$ leukocytes isolated using a cell enrichment device of the invention (cutoff size 4 μm) and 5×10$^6$ H1650 cells were isolated by using RNeasy mini kit (Qiagen). Two micrograms of total RNAs from leukocytes and H1650 cells were reverse transcribed to obtain first strand cDNAs using 100 pmol random hexamer (Roche) and 200 U Superscript II (Invitrogen) in a 20 μl reaction. The subsequent PCR was carried out using 0.5 μl of the first strand cDNA reaction and 10 pmol of forward and reverse primers in total 25 μl of mixture. The PCR was run for 40 cycles of 95° C. for 20 seconds, 56° C. for 20 seconds, and 70° C. for 30 seconds. The amplified products were separated on a 1% agarose gel. As shown in FIG. 26A, BCKDK was found to be expressed in both leukocytes and H1650 cells; CD45 was expressed only in leukocytes; and both EpCAM and EGFR were expressed only in H1650 cells. These results, which are fully consistent with the profile of EGFR expression shown in FIG. 26B, confirmed that EGFR is a particularly useful target for assaying mixtures of cells that include both leukocytes and cancer cells, because only the cancer cells will be expected to produce a signal.

What is claimed is:

1. A method for determining the presence or absence of a fetal aneuploidy using a maternal blood sample, the method comprising:
   a. obtaining a test sample comprising a mixture of fetal and maternal genomic nucleic acids from a maternal blood sample;
   b. selectively amplifying a plurality of target nucleic acids from the test sample and a plurality of control nucleic acids from a plurality of control regions using primers labeled with a unique tag for each target nucleic acid and for each control nucleic acid, thereby generating amplification products, wherein the target nucleic acids are selected from one or more chromosomes to be tested for aneuploidy, and wherein the control regions are selected from regions of the genome where aneuploidy is not expected;
   c. amplifying the amplification products using universal primers;
   d. detecting the amplified target nucleic acids and amplified control nucleic acids;
   e. quantifying the detected, amplified target nucleic acids and the detected, amplified control nucleic acids from the test sample;
   f. analyzing the test sample for presence or absence of a fetal aneuploidy by comparing the quantity of the detected amplified target nucleic acids with the quantity of the detected amplified control nucleic acids; and
   g. generating a report on presence or absence of aneuploidy in the maternal blood sample.

2. The method of claim 1, wherein the target nucleic acids are selected from one or more of chromosomes X, Y, 13, 18, and 21.

3. The method of claim 1, wherein the target nucleic acid sequences are quantified by chromatography, electrophoresis, comparative genomic hybridization (CGH), microarrays, or bead arrays.

4. The method of claim 3, wherein the chromatography is selected from gas chromatography, supercritical fluid chromatography, and liquid chromatography.

5. The method of claim 3, wherein the electrophoresis is selected from capillary electrophoresis, capillary zone electrophoresis, capillary isoelectric focusing, capillary electrochromatography, micellar electrokinetic capillary chromatography, isotachophoresis, transient isotachophoresis, and capillary gel electrophoresis.

6. The method of claim 1, wherein the target nucleic acid sequences are quantified using molecular inversion probes (MIPs).

7. The method of claim 3, wherein the target nucleic acid sequences are quantified using a microarray.

8. The method of claim 7, wherein the microarray is used to detect at least 1,000 different target nucleic acids.

9. The method of claim 1, wherein the chromosomes are tested for any one or more of fetal trisomy 13, trisomy 18, or trisomy 21.

10. The method of claim 1, wherein the target nucleic acids are single nucleotide polymorphisms (SNPs), short tandem repeats (STRs), or RNA transcripts.

11. The method of claim 1, wherein the amplification comprises:
hybridizing one set of oligonucleotides per target nucleic acid, wherein each set comprises two or more oligonucleotide probes that each hybridize to different regions within the target nucleic acid;
ligating the two or more hybridized oligonucleotide probes for each of the target nucleic acids to create amplification templates for each of the target nucleic acids; and
amplifying the amplification templates.

12. The method of claim 11, further comprising attaching biotin to the target nucleic acids to generate biotin-labeled target nucleic acids.

13. The method of claim 12, further comprising attaching the biotin-labeled target nucleic acids to a streptavidin coated solid support.

14. The method of claim 1, wherein quantifying the target nucleic acids further comprises determining a gene or allele copy number or both a gene copy number and an allele copy number.

15. The method of claim 14, further comprising determining fetal trisomy or monosomy based on the gene or allele copy number or the gene copy number and the allele copy number determination.

16. A method of determining the presence or absence of a fetal aneuploidy using a maternal blood sample, the method comprising:
a. obtaining a mixture of fetal and maternal genomic nucleic acids from a maternal blood sample;
b. hybridizing one set of oligonucleotide probes per target nucleic acid, wherein each set comprises two or more oligonucleotide probes that each hybridize to a target region within the target nucleic acid, and ligating the two or more hybridized oligonucleotide probes for each of the target nucleic acids to create amplification templates for each of the target nucleic acids, wherein each amplification template comprises a universal primer region coupled to a unique tag region;
c. amplifying the amplification templates using universal primers, thereby generating amplification products;
d. detecting the amplification products and quantifying the detected amplification products to determine a chromosomal copy number; and
e. generating a report on a presence or absence of aneuploidy in the maternal blood sample based on the chromosomal copy number.

17. The method of claim 16, wherein the genomic nucleic acids are from one or more of chromosomes X, Y, 13, 18, or 21.

18. The method of claim 16, wherein the fetal aneuploidy is a trisomy or a monosomy.

19. The method of claim 18, wherein the trisomy is trisomy 13, trisomy 18, or trisomy 21.

20. The method of claim 16, further comprising enriching the mixture of fetal and maternal genomic nucleic acids for fetal genomic nucleic acids.

21. The method of claim 16, further comprising labeling the fetal and maternal genomic nucleic acids with biotin and immobilizing the biotin-labeled genomic nucleic acids to a solid support prior to step b.

22. The method of claim 21, wherein the solid support comprises a streptavidin coating.

23. The method of claim 21, wherein the solid support is a bead or particle.

24. The method of claim 16, wherein detecting the amplification products and quantifying the detected amplification products is performed on a microarray.

25. The method of claim 24, wherein the microarray is used to detect at least 1,000 different labeled nucleic acids.

26. The method of claim 16, wherein detecting the amplification products and quantifying the detected amplification products is performed using molecular inversion probes (MIPs).

27. The method of claim 16, wherein the amplification comprises one or more of quantitative polymerase chain reaction (Q-PCR), quantitative fluorescent PCR (QF-PCR), multiplex fluorescent PCR (MF-PCR), real time PCR (RT-PCR), single cell PCR, restriction fragment length polymorphism PCR (PCR-RFLP), PCR-RFLP/RT-PCR-RFLP, hot start PCR, nested PCR, in situ polonony PCR, in situ rolling circle amplification (RCA), bridge PCR, picotiter PCR and emulsion PCR, ligase chain reaction (LCR), transcription amplification, self-sustained sequence replication, selective amplification of target polynucleotide sequences, consensus sequence primed PCR (CP-PCR), arbitrarily primed PCR (AP-PCR), degenerate oligonucleotide-primed PCR (DOP-PCR) or nucleic acid based sequence amplification (NABSA).

28. The method of claim 27, wherein the amplification comprises nested PCR.

29. The method of claim 27, wherein the amplification comprises rolling circle amplification (RCA).

30. The method of claim 27, wherein the amplification comprises bridge PCR.

* * * * *

UNITED STATES PATENT AND TRADEMARK OFFICE
CERTIFICATE OF CORRECTION

| | |
|---|---|
| PATENT NO. | : 11,261,492 B2 |
| APPLICATION NO. | : 16/594505 |
| DATED | : March 1, 2022 |
| INVENTOR(S) | : Ravi Kapur et al. |

It is certified that error appears in the above-identified patent and that said Letters Patent is hereby corrected as shown below:

In the Claims

In Column 112, Line 34 (Approx.), Claim 27:
Delete "polonony" and Insert -- polony --

Signed and Sealed this
Nineteenth Day of April, 2022

*Katherine Kelly Vidal*

Katherine Kelly Vidal
*Director of the United States Patent and Trademark Office*

SEQUENCE LISTING

```
<160> NUMBER OF SEQ ID NOS: 172

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
acagaagtct gggatgtgga                                                  20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcccaaaaag acagacagaa                                                  20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
acctgttgta tggcagcagt                                                  20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agttgactct ttccccaact a                                                21

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
```
tttggtaaga aaaacatctc cc                                          22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggctgcagtt agctgtcatt                                             20

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cctgggcaac aagagcaaa                                              19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agcagagaga cataattgtg                                             20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acctgccaaa ttttaccagg                                             20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gacagagaga gggaataaac c                                           21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atatatgcac atccatccat g                                         21

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggccaaagat agatagcaag gta                                       23

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
acatcgctcc ttaccccatc                                           20

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tgtacccatt aaccatcccc a                                         21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
acagaagtct gggatgtgga                                           20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcccaaaaag acagacagaa                                           20

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agagtgagat tctgtctcaa ttaa                                      24

```
<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggccctgtgt agaagctgta                                                    20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atcaggattc caggaggaaa                                                    20

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
acctgggagg cggagctc                                                      18

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggcataaaaa tagtacagca agc                                                23

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
atttgaacag aggcatgtac                                                    20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
catggatgca gaattcacag                                                    20
```

```
<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tcatctccct gtttggtagc                                                 20

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
agggatcttc agagaaacag g                                               21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tgacactatc agctctctgg c                                               21

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggtgcttgct gtaaatataa ttg                                             23

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cactacagca gattgcacca                                                 20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
caaacccgac taccagcaac                                                 20
```

```
<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gagccatgtt catgccactg                                               20

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
caaagagtga atgctgtaca aacagc                                        26

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
caagatgtga gtgtgctttt caggag                                        26

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
atcccacagg atgcctattt                                               20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
acgggagctt ttgagaagtt                                               20

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tcaaattttt aagtctcacc agg                                           23

<210> SEQ ID NO 36
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gcctgtagaa agcaacaacc                                                 20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggtgacagag caagaccttg                                                 20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gcctcttgtc atcccaagta                                                 20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ctctcttcat ccaccattgg                                                 20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gctgtaagag acctgtgttg                                                 20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tggaaccact tcattcttgg                                                 20

<210> SEQ ID NO 42
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
atttcagacc aagataggc                                          19

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cctatttaag tttctgtaag g                                       21

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
atggtgtaga ccctgtggaa                                         20

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ctgcacaaca tagtgagacc tg                                      22

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
agattaccca gaaatgagat cagc                                    24

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tcatgtgaca aaagccacac                                         20

<210> SEQ ID NO 48
<211> LENGTH: 25
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 48
agacagaaat atagatgaga atgca                                           25

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tcatgtgaca aaagccacac                                                 20

<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
agacagaaat atagatgaga atgca                                           25

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tttccagtgg aaaccaaact                                                 20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tccagcaaca acaagagaca                                                 20

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gtcctcatcc tgtaaaacgg g                                               21

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ccactaacta gtttgtgact ttgg                                              24

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ctgtcctcta ggctcattta gc                                                22

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ttatgaagca gtgatgccaa                                                   20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
agctggagag ggatagcatt                                                   20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tgcattgcat gaaagtagga                                                   20

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gatgatagag atggcacatg a                                                 21

<210> SEQ ID NO 60
<211> LENGTH: 23
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 60
tcttcataca tgctttatca tgc                                             23

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gtgagtcaat tccccaag                                                   18

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gttgtattag tcaatgttct cc                                              22

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
atgatgaatg catagatgga tg                                              22

<210> SEQ ID NO 64
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
aatgtgtgtc cttccaggc                                                  19

<210> SEQ ID NO 65
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ttgcagggaa accacagtt                                                  19

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 66
tccttggaat aaattcccgg                                           20

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
cttagaggga cagaactaat aggc                                      24

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
agcctattgt gggtttgtga                                           20

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
atgtacatgt gtctgggaag g                                         21

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ttctctacat atttactgcc aaca                                      24

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gagtttgaaa ataaagtgtt ctgc                                      24

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 72
ccccacccct tttagtttta                                                    20

<210> SEQ ID NO 73
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
atgtacgata cgtaatactt gacaa                                              25

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gtcccaaagg acctgctc                                                      18

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gcaccccttt atacttgggt g                                                  21

<210> SEQ ID NO 76
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
tagtactcta ccatccatct atccc                                              25

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
aacagaacca ataggctatc tatc                                               24

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 78
tacagtaaat cacttggtag gaga    24

<210> SEQ ID NO 79
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
tccgcgaagt gaagaac    17

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
cttggggaga accatcctca    20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ccggctacaa gtgatgtcta    20

<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
cctaggtaac atagtgagac cttg    24

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
cctctaaagc atagggtcca    20

<210> SEQ ID NO 84
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
cccatctgag aacacgctg                                            19

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
agtttaggag attatcaagc tgg                                       23

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
gttcccataa tagatgtatc cag                                       23

<210> SEQ ID NO 87
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ttggtactta ataaaccctc tttt                                      24

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ctagagggac agaaccaata gg                                        22

<210> SEQ ID NO 89
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
tgtctgctaa tgaatgattt gg                                        22

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90 ccatcccta aacctctcat                                                    20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gtgggacctt gtgattgtgt                                                   20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
ctggctgaca cttagggaaa                                                   20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
acagaaaacc ttttgggacc                                                   20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
cccagccctg aatattatca                                                   20

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
tgcacttaat atctggtgat gg                                                22

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
atttctttcc ctctgcaacc                                                   20

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
agcccatttt cataataaat cc                                              22

<210> SEQ ID NO 98
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
aatcagtgct ttctgtacta ttgg                                            24

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
cacttcatgg cttaccacag                                                 20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
gacctttgga aagctagtgt                                                 20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
tgtcacgttt accctggaac                                                 20

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
tattcttcta tccaaccaac agc                                             23

<210> SEQ ID NO 103
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 103
ttgggtgggg acacagag                                                 18

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 104
cctggctcaa ggaattacaa                                               20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 105
ccagcctggc tgttagagta                                               20

<210> SEQ ID NO 106
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 106
atattcttat attccatatg gcaca                                         25

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 107
tggagtctct gggtgaagag                                               20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 108
caggagtatg ggatcaccag                                               20

```
<210> SEQ ID NO 109
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109 cagcaattt tcaaaggc                                                      18

<210> SEQ ID NO 110
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
agatcattca tataacctca aaaga                                             25

<210> SEQ ID NO 111
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
ttgctgctgg tggtggc                                                      17

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
cagggattcc gtcatatggc                                                   20

<210> SEQ ID NO 113
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
gatcggcctc ttcatgcg                                                     18

<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
gatccaaagg tcatcaactc cc                                                22

<210> SEQ ID NO 115
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
gctgtccaac gaatgggc                                                    18

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
ggcgttctcc tttctccagg                                                  20

<210> SEQ ID NO 117
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
atgcactggg ccaggtctt                                                   19

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
cgatggtaca tatgggtggc t                                                21

<210> SEQ ID NO 119
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
aggctgtcca acgaatggg                                                   19

<210> SEQ ID NO 120
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
ctgagggagg cgttctcct                                                   19

<210> SEQ ID NO 121
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
tcagagcctg tgtttctacc aa                                            22

<210> SEQ ID NO 122
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
tggtctcaca ggaccactga tt                                            22

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
tccaaatgag ctggcaagtg                                               20

<210> SEQ ID NO 124
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
tcccaaacac tcagtgaaac aaa                                           23

<210> SEQ ID NO 125
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
aaataatcag tgtgattcgt ggag                                          24

<210> SEQ ID NO 126
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
gaggccagtg ctgtctctaa gg                                            22

<210> SEQ ID NO 127
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 127
gtgcatcgct ggtaacatcc                                              20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
tgtggagatg agcagggtct                                              20

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
acttcacagc cctgcgtaaa c                                            21

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
atgggacagg cactgatttg t                                            21

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
atcgcattca tgcgtcttca                                              20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
atccccatgg caaactcttg                                              20

<210> SEQ ID NO 133
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 133
gcagcgggtt acatcttctt tc                                              22

<210> SEQ ID NO 134
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
cagctctggc tcacactacc ag                                              22

<210> SEQ ID NO 135
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
gcagcgggtt acatcttctt tc                                              22

<210> SEQ ID NO 136
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
catcctcccc tgcatgtgt                                                  19

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
ccgcagcatg tcaagatcac                                                 20

<210> SEQ ID NO 138
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
tccttctgca tggtattctt tctct                                           25

<210> SEQ ID NO 139
<211> LENGTH: 14
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 139
tttgggctgg ccaa                                                           14

<210> SEQ ID NO 140
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 140
ttttgggcgg gcca                                                           14

<210> SEQ ID NO 141
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
atggccagcg tggacaa                                                        17

<210> SEQ ID NO 142
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
agcaggtact gggagccaat att                                                 23

<210> SEQ ID NO 143
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 143
atgagctgcg tgatga                                                         16

<210> SEQ ID NO 144
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 144
atgagctgca tgatga                                                         16

<210> SEQ ID NO 145
<211> LENGTH: 22
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 145
gcctcttaca cccagtggag aa					22

<210> SEQ ID NO 146
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
ttctgggatc cagagtccct ta					22

<210> SEQ ID NO 147
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 147
accggagccc agca						14

<210> SEQ ID NO 148
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 148
accggagctc agca						14

<210> SEQ ID NO 149
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 149
accggagcac agca						14

<210> SEQ ID NO 150
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
tcgcaaaggg catgaactac t					21

<210> SEQ ID NO 151
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
atcttgacat gctgcggtgt t					21

<210> SEQ ID NO 152
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 152
ttggtgcacc gcga					14

<210> SEQ ID NO 153
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 153
tggtgctccg cgac					14

<210> SEQ ID NO 154
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
agtcaggacc catgcacgg					19

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
acccaagatg cagcagtgtg					20

<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
gatgtcctcc ttgttctact c					21

<210> SEQ ID NO 157
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 157
tacagggaat aatcgagcat gc                                              22

<210> SEQ ID NO 158
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
gaagggaaat agcaaatgga ca                                              22

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
cgatggagtc caagttctgg                                                 20

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
agcacttaca gctctggcca                                                 20

<210> SEQ ID NO 161
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
gactgaacat aactgtaggc tg                                              22

<210> SEQ ID NO 162
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
tcgagtgcat tccattccg                                                  19

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
```

```
atggaatggc atcaaacgga a                                              21
```

<210> SEQ ID NO 164
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 164

```
tggctgtcca ttcca                                                     15
```

<210> SEQ ID NO 165
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165

```
atgcagcaag gcacagacta arcaaggaga sgcaaaattt tcrtagggga gagaaatggg    60
tcatt                                                                65
```

<210> SEQ ID NO 166
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166

```
atgcagcaag gcacagacta cg                                             22
```

<210> SEQ ID NO 167
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167

```
agagggaga gaaatgggtc att                                             23
```

<210> SEQ ID NO 168
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168

```
caaggcacag actaagcaag gagag                                          25
```

<210> SEQ ID NO 169
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 169
ggcaaaattt tcatagggga gagaaatggg tcatt                              35

<210> SEQ ID NO 170
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
gcaactcatc atgca                                                    15

<210> SEQ ID NO 171
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
ttttgggcgg gccaa                                                    15

<210> SEQ ID NO 172
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
gaccgtttgg gagttgata                                                19
```